(12) United States Patent
Chang et al.

(10) Patent No.: US 10,254,567 B2
(45) Date of Patent: Apr. 9, 2019

(54) UV-ABSORBING VINYLIC MONOMERS AND USES THEREOF

(71) Applicant: Novartis AG, Basel (CH)

(72) Inventors: Frank Chang, Cumming, GA (US); Ryan DeSousa, Atlanta, GA (US); Troy Vernon Holland, Suwanee, GA (US); John Dallas Pruitt, Suwanee, GA (US); Jared Nelson, Buford, GA (US)

(73) Assignee: Novartis AG, Basel (CH)

( * ) Notice: Subject to any disclaimer, the term of this patent is extended or adjusted under 35 U.S.C. 154(b) by 59 days.

(21) Appl. No.: 15/434,105

(22) Filed: Feb. 16, 2017

(65) Prior Publication Data

US 2017/0242275 A1 Aug. 24, 2017

Related U.S. Application Data

(60) Provisional application No. 62/298,137, filed on Feb. 22, 2016.

(51) Int. Cl.

| | |
|---|---|
| *C07D 249/20* | (2006.01) |
| *G02C 7/10* | (2006.01) |
| *C08F 220/70* | (2006.01) |
| *C08F 230/08* | (2006.01) |
| *G02B 1/04* | (2006.01) |
| *G02C 7/04* | (2006.01) |
| *B29D 11/00* | (2006.01) |
| *C08F 20/36* | (2006.01) |
| *G02B 5/20* | (2006.01) |
| *G02B 5/22* | (2006.01) |
| *C07C 233/38* | (2006.01) |
| *B29K 105/00* | (2006.01) |

(52) U.S. Cl.
CPC ........ *G02C 7/108* (2013.01); *B29D 11/00134* (2013.01); *C07C 233/38* (2013.01); *C07D 249/20* (2013.01); *C08F 20/36* (2013.01); *C08F 220/70* (2013.01); *C08F 230/08* (2013.01); *G02B 1/043* (2013.01); *G02B 5/208* (2013.01); *G02B 5/223* (2013.01); *G02C 7/049* (2013.01); *B29K 2105/0002* (2013.01)

(58) Field of Classification Search
CPC ...... G02C 7/108; G02C 7/049; C07C 233/38; G02B 5/208; G02B 2/223; G02B 1/043; C08F 20/38; C08F 230/08; C08F 220/70; C07D 249/20; B29K 2105/0002; B29D 11/00134

See application file for complete search history.

(56) References Cited

U.S. PATENT DOCUMENTS

| | | |
|---|---|---|
| 4,136,250 A | 1/1979 | Mueller et al. |
| 4,153,641 A | 5/1979 | Deichert et al. |
| 4,182,822 A | 1/1980 | Chang et al. |
| 4,189,546 A | 2/1980 | Deichert et al. |
| 4,254,248 A | 3/1981 | Friends et al. |
| 4,259,467 A | 3/1981 | Keogh et al. |
| 4,260,725 A | 4/1981 | Keogh et al. |
| 4,261,875 A | 4/1981 | Leboeuf |
| 4,276,402 A | 6/1981 | Chromecek et al. |
| 4,327,203 A | 4/1982 | Deichert et al. |
| 4,341,889 A | 7/1982 | Deichert et al. |
| 4,343,927 A | 8/1982 | Chang |
| 4,355,147 A | 10/1982 | Deichert et al. |
| 4,390,676 A | 6/1983 | Loshaek |
| 4,444,711 A | 4/1984 | Schad |
| 4,460,534 A | 7/1984 | Boehm et al. |
| 4,486,577 A | 12/1984 | Mueller et al. |
| 4,528,311 A | 7/1985 | Beard et al. |
| 4,543,398 A | 9/1985 | Angelini et al. |
| 4,605,712 A | 8/1986 | Mueller |
| 4,612,358 A | 9/1986 | Besecke et al. |
| 4,661,575 A | 4/1987 | Tom |
| 4,684,538 A | 8/1987 | Klemarczyk |
| 4,703,097 A | 10/1987 | Wingler et al. |
| 4,716,234 A | 12/1987 | Dunks et al. |
| 4,803,254 A | 2/1989 | Dunks et al. |
| 4,833,218 A | 5/1989 | Lee |
| 4,837,289 A | 6/1989 | Mueller |
| 4,954,586 A | 9/1990 | Toyoshima et al. |

(Continued)

FOREIGN PATENT DOCUMENTS

| | | |
|---|---|---|
| CA | 1318755 C | 6/1993 |
| EP | 0314620 A1 | 5/1989 |

(Continued)

OTHER PUBLICATIONS

Nishio, et al.; "A novel intramolecular photocyclization of N-(2-bromoalkanoyl) derivatives of 2-acylanilines via 1,8-hydrogen abstraction"; Helvetica Chimica Acta; vol. 88; 2005; pp. 996-1003.

Tanito, et al.; "Protective effects of soft acrylic yellow filter against blue light-induced retinal damage in rats"; Experimental Eye Research; vol. 83; 2006; pp. 1493-1504.

Kernt, et al.; Cytoprotective effects of a blue light-filtering intraocular lens on human retinal pigment epithelium by reducing phototoxic effects on vascular endothelial growth factor-a, Bax, and Bcl-2 expression; J. Cataract Refractive Surgery; 2009, vol. 35; pp. 354-362.

Rezai, et al.; "AcrySof natural filter decreases blue light-induced apoptosis in human retinal pigment epithelium"; Graefe's Arch Clin Exp Ophthalmol; 2008; vol. 246; pp. 671-676.

(Continued)

*Primary Examiner* — Sanza L. McClendon
(74) *Attorney, Agent, or Firm* — Jian Zhou

(57) ABSTRACT

Described herein are water-soluble UV-absorbing vinylic monomers and their uses in preparing UV-absorbing contact lenses capable of blocking ultra-violet ("UV") radiation and optionally (but preferably) violet radiation with wavelengths from 380 nm to 440 nm, thereby protecting eyes to some extent from damages caused by UV radiation and potentially from violet radiation. This invention also provides a UV-absorbing contact lens.

5 Claims, 3 Drawing Sheets

(56) References Cited

U.S. PATENT DOCUMENTS

Figure 1:
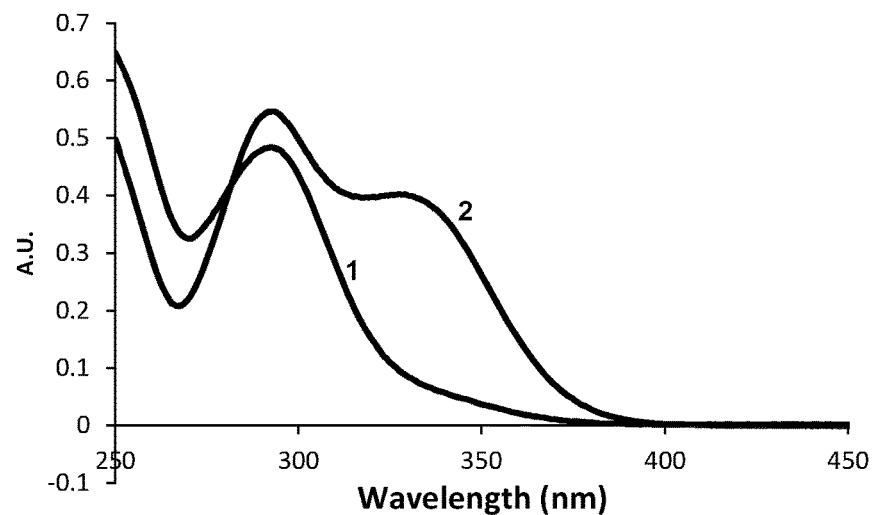

| | | |
|---|---|---|
| 4,954,587 A | 9/1990 | Mueller |
| 4,998,817 A | 3/1991 | Zeltzer |
| 5,010,141 A | 4/1991 | Sharma et al. |
| 5,034,461 A | 7/1991 | Lai et al. |
| 5,039,761 A | 8/1991 | Ono et al. |
| 5,070,170 A | 12/1991 | Robertson |
| 5,079,319 A | 1/1992 | Mueller |
| 5,124,723 A | 6/1992 | Laver et al. |
| 5,190,565 A | 3/1993 | Berenbaum et al. |
| 5,235,358 A | 8/1993 | Mutzhas |
| 5,346,946 A | 9/1994 | Yokoyama et al. |
| 5,358,995 A | 10/1994 | Kunzler et al. |
| 5,387,632 A | 2/1995 | Lai et al. |
| 5,416,132 A | 5/1995 | Yokoyama et al. |
| 5,451,617 A | 9/1995 | Lai et al. |
| 5,470,932 A | 11/1995 | Jinkerson |
| 5,486,579 A | 1/1996 | Lai et al. |
| 5,487,885 A | 1/1996 | Sovak et al. |
| 5,508,317 A | 4/1996 | Mueller |
| 5,543,504 A | 8/1996 | Jinkerson |
| 5,583,163 A | 12/1996 | Mueller |
| 5,592,245 A | 1/1997 | Moore et al. |
| 5,617,154 A | 4/1997 | Hoffman |
| 5,625,427 A | 4/1997 | Araujo et al. |
| 5,637,726 A | 6/1997 | Collins et al. |
| 5,665,840 A | 9/1997 | Pohlmann et al. |
| 5,712,356 A | 1/1998 | Bothe et al. |
| 5,741,924 A | 4/1998 | Sovak et al. |
| 5,760,100 A | 6/1998 | Nicolson et al. |
| 5,789,464 A | 8/1998 | Mueller |
| 5,838,419 A | 11/1998 | Holland |
| 5,843,346 A | 12/1998 | Morrill |
| 5,849,810 A | 12/1998 | Mueller |
| 5,849,841 A | 12/1998 | Muhlebach et al. |
| 5,866,635 A | 2/1999 | Collins et al. |
| 5,894,002 A | 4/1999 | Boneberger et al. |
| 5,925,787 A | 4/1999 | Taylor et al. |
| 5,962,548 A | 10/1999 | Vanderlaan et al. |
| 5,975,695 A | 11/1999 | Baiocchi |
| 5,981,675 A | 11/1999 | Valint et al. |
| 6,039,913 A | 3/2000 | Hirt |
| 6,132,044 A | 10/2000 | Sternbergh |
| 6,165,408 A | 12/2000 | Steinmann |
| 6,221,303 B1 | 4/2001 | Steinmann |
| 6,303,687 B1 | 10/2001 | Mueller |
| 6,305,801 B1 | 10/2001 | Kerns et al. |
| 6,420,290 B1 | 7/2002 | Brocheton et al. |
| 6,432,137 B1 | 8/2002 | Nanushyan |
| 6,472,489 B1 | 10/2002 | Stockinger |
| 6,479,587 B1 | 11/2002 | Stockinger |
| 6,492,478 B1 | 12/2002 | Steinmann |
| 6,627,124 B1 | 9/2003 | Herbrechtsmeier et al. |
| 6,641,261 B2 | 11/2003 | Wang |
| 6,762,264 B2 | 7/2004 | Kuenzler et al. |
| 6,800,225 B1 | 10/2004 | Hagmann et al. |
| 6,811,727 B2 | 11/2004 | Havens et al. |
| 6,955,430 B2 | 10/2005 | Pratt |
| 6,995,192 B2 | 2/2006 | Phelan et al. |
| 7,091,283 B2 | 8/2006 | Mueller et al. |
| 7,238,750 B2 | 7/2007 | Mueller et al. |
| 7,255,435 B2 | 8/2007 | Pratt |
| 7,268,189 B2 | 9/2007 | Mueller et al. |
| 7,276,544 B2 | 10/2007 | Lai et al. |
| 7,278,737 B2 | 10/2007 | Mainster et al. |
| 7,364,291 B2 | 4/2008 | Haywood et al. |
| 7,384,590 B2 | 6/2008 | Kelly et al. |
| 7,387,759 B2 | 6/2008 | Kelly et al. |
| 7,520,605 B2 | 4/2009 | Casper et al. |
| 7,520,608 B2 | 4/2009 | Ishak et al. |
| 7,521,519 B1 | 4/2009 | Hirt et al. |
| 7,524,060 B2 | 4/2009 | Sanchez Ramos |
| 7,556,376 B2 | 7/2009 | Ishak |
| 7,605,190 B2 | 10/2009 | Moszner et al. |
| 7,703,917 B2 | 4/2010 | Sanchez Ramos |
| 7,748,845 B2 | 7/2010 | Casper et al. |
| 7,771,470 B2 | 8/2010 | Mentak |
| 7,803,359 B1 | 9/2010 | Jinkerson et al. |
| 7,825,257 B1 | 11/2010 | Deo et al. |
| 7,842,367 B2 | 11/2010 | Mentak |
| 7,857,848 B2 | 12/2010 | Mentak |
| 7,884,228 B1 | 2/2011 | Laredo |
| 7,915,323 B2 | 3/2011 | Awasthi et al. |
| 7,947,849 B2 | 5/2011 | Laredo |
| 7,977,430 B2 | 7/2011 | Devlin et al. |
| 8,047,650 B2 | 11/2011 | Mainster et al. |
| 8,088,313 B2 | 1/2012 | Hagmann et al. |
| 8,096,656 B2 | 1/2012 | Giraudet |
| 8,113,651 B2 | 2/2012 | Blum et al. |
| 8,153,703 B2 | 4/2012 | Laredo |
| 8,192,021 B2 | 6/2012 | Giraudet |
| 8,207,244 B2 | 6/2012 | Laredo |
| 8,232,326 B2 | 7/2012 | Laredo |
| 8,262,947 B2 | 9/2012 | Laredo |
| 8,262,948 B2 | 9/2012 | Laredo et al. |
| 8,329,775 B2 | 12/2012 | Laredo |
| 8,360,574 B2 | 1/2013 | Ishak et al. |
| 8,403,478 B2 | 3/2013 | Ishak |
| 8,420,711 B2 | 4/2013 | Awasthi et al. |
| 8,475,691 B2 | 7/2013 | Laredo |
| 8,500,274 B2 | 8/2013 | Ishak |
| 8,585,938 B1 | 11/2013 | Jinkerson et al. |
| 8,877,103 B2 | 11/2014 | Alvarez-Carrigan et al. |
| 8,882,267 B2 | 11/2014 | Ishak et al. |
| 9,052,439 B2 * | 6/2015 | Samuel ............... G02B 1/043 |
| 9,187,601 B2 | 11/2015 | Huang et al. |
| 2006/0252844 A1 | 11/2006 | Mentak |
| 2006/0252850 A1 | 11/2006 | Jani et al. |
| 2007/0004852 A1 | 1/2007 | Mentak |
| 2007/0004863 A1 | 1/2007 | Mentak |
| 2007/0092830 A1 | 4/2007 | Lai et al. |
| 2007/0092831 A1 | 4/2007 | Lai et al. |
| 2008/0015315 A1 | 1/2008 | Chang et al. |
| 2008/0143003 A1 | 6/2008 | Phelan |
| 2008/0143958 A1 | 6/2008 | Medina et al. |
| 2008/0231798 A1 | 9/2008 | Zhou et al. |
| 2008/0234457 A1 | 9/2008 | Zhou et al. |
| 2010/0041787 A1 | 2/2010 | Chen |
| 2010/0296049 A1 | 11/2010 | Justynska-Reinmann et al. |
| 2010/0298446 A1 | 11/2010 | Chang et al. |
| 2011/0075096 A1 | 3/2011 | Ishak et al. |
| 2011/0157546 A1 | 6/2011 | Ishak et al. |
| 2012/0023869 A1* | 2/2012 | Samuel ............... G02B 1/043 53/425 |
| 2012/0023896 A1* | 2/2012 | DeDe ............... F23M 11/00 60/39.094 |
| 2012/0075577 A1 | 3/2012 | Ishak et al. |
| 2012/0088843 A1 | 4/2012 | Chang et al. |
| 2012/0088844 A1 | 4/2012 | Kuyu et al. |
| 2012/0244088 A1 | 9/2012 | Saxena et al. |
| 2012/0245249 A1 | 9/2012 | Saxena et al. |
| 2013/0282115 A1 | 10/2013 | Ishak |
| 2014/0004061 A1 | 1/2014 | Levins et al. |
| 2014/0004063 A1 | 1/2014 | Daly |
| 2014/0055736 A1 | 2/2014 | Ishak |
| 2014/0233105 A1 | 8/2014 | Schmeder et al. |
| 2014/0300857 A1 | 10/2014 | Cohen Tannoudji et al. |
| 2015/0098058 A1 | 4/2015 | De Ayguavives et al. |
| 2015/0103310 A1 | 4/2015 | De Ayguavives et al. |
| 2015/0234208 A1 | 8/2015 | De Ayguavives et al. |
| 2015/0309213 A1* | 10/2015 | Chang ............... C07F 7/089 523/107 |
| 2015/0370094 A1 | 12/2015 | Hashimoto et al. |
| 2016/0017218 A1 | 1/2016 | Kojima et al. |
| 2016/0304701 A1 | 10/2016 | Kakinuma et al. |
| 2016/0313575 A1 | 10/2016 | Kakinuma et al. |
| 2016/0357031 A1* | 12/2016 | Holland ............ B29D 11/00038 |
| 2017/0242274 A1* | 8/2017 | Holland ............... C07C 233/33 |

FOREIGN PATENT DOCUMENTS

| | | |
|---|---|---|
| EP | 0274844 B1 | 11/1991 |
| EP | 0632329 A1 | 1/1995 |
| EP | 2523943 B1 | 11/2014 |
| JP | S62230759 | 10/1987 |

(56) References Cited

FOREIGN PATENT DOCUMENTS

| JP | H0688066 A | 3/1994 |
|---|---|---|
| JP | H06207142 A | 7/1994 |
| WO | 8800942 A | 2/1988 |
| WO | 02071106 A1 | 9/2002 |
| WO | 04052837 A2 | 6/2004 |
| WO | 2007/050395 A2 | 5/2007 |
| WO | 2011/130138 A1 | 10/2011 |
| WO | 2013/188825 A1 | 12/2013 |
| WO | 2014/011581 A2 | 1/2014 |
| WO | 2014/018208 A1 | 1/2014 |

OTHER PUBLICATIONS

Algvere, et al.; "Age-related maculopathy and the impact of blue light hazard" Acta Ophthalmologica Scandinavica; 2006; vol. 84; pp. 4-15.

Mainster; "Violet and blue light blocking intraocular lenses: photoprotection versus photoreception"; Br. J. Ophthalmol 2006; vol. 90; pp. 784-792.

Park, et al.; "Improved loading and cleavage methods for solid-phase synthesis using chlorotrityl resins: synthesis and testing of a library of 144 discrete chemicals as potential famesyltransferase inhibitors"; Journal of Combinatorial Chemistry; American Chemical Society; 2004; vol. 6, No. 3; pp. 407-413.

Kosasayama, et al.; Cyclic guanidines. Vl.(1) synthesis of hypoglycemic tricyclic guanidines; Chem. Pharm. Bull; 1979; vol. 27, No. 4; pp. 880-892.

Zhou, et al. "Light filtering in a retinal pigment epithelial cell culture model"; Optometry and Vision Science; American Academy of Optometry; 2011; vol. 88; No. 6; pp. 759-765.

Database WPI; Week 198746, Thomson Scientific, London, GB; AN 1987-324524, XP002769134 and JPS62230759; Nippon Shokubai Kagaku Kogyo, Co. Ltd.; Abstract translation only.

Database CA; Chemical Abstracts Service, Columbus, Ohio, US; Nakagawa, Hiroo et al: "Polyurethane coating compositions with excellent weatherability", XP002769135, retrieved from STN Database accession No. 1995:169562 abstract and JPH06207142; Nippon Catalytic Chem. Ind., Jul. 26, 1994; Machine translation.

McAlees, et al.; "Hydrogenation of substituted phthalic anhydrides over palladium"; J. Chem. Soc., Perkin 1 Trans. (1977), pp. 2030-2036.

Umeda, et al.; "Polymeric phospholipid analogues, 14. The convenient preparation of a vinyl monomer containing a phospholipid analogue"; Makromolecular Chem. Rapid Communications; 1982; vol. 3, No. 7, pp. 457-459.

Waters et al.; "The effect of phenylbenzotriazole derivatives on the photoyellowing of wool"; Textile Research Journal; vol. 48; Issue 5, May 1978; pp. 251-255.

Evans, et al.; "Photoprotection of wool with sulfonated 2-(2'-hydroxyaryl)-2H-benzotriazoles"; Polymer Degradation and Stability; Elsevier Applied Science Publishers Ltd.; 1986; vol. 14; No. 3; pp. 263-284.

Rieker, et al.; "Ultraviolet stabilizers of the 2-(Hydroxyphenyl)benzotrlazole class. Influence of substituents on structure and spectra"; The Journal of Physical Chemistry; American Chemical Society; 1992, vol. 96, No. 25, pp. 10225-10234.

El-Tahlawy, et al.; Cyclodextrin-4 hydroxy benzophenone inclusion complex for UV protective cotton fabric; TJTI; The Textile Institute; 2007; vol. 98; No. 5; pp. 453-462.

Leaver, et al.; Dual role of a hydroxyphenylbenzotriazole UV absorber in the photooxidation of wool; Journal of Polymer Science: Polymer Chemistry Edition; John Wiley & Sons, Inc.; 1979: vol. 17; pp. 1531-1541.

Zayat, et al.; Preventing UV-light damage of light sensitive materials using a highly protective UV-absorbing coating; Chemical Society Reviews; The Royal Society of Chemistry; 2007; vol. 36; pp. 1270-1281.

Ma, et al.; "Synthesis of a novel water-soluble polymeric UV-absorber for cotton"; Chinese Chemical Letters; 22; 2011; pp. 1489-1491.

Farkas, et al.; "Synthesis of new 2-(2'-hydroxyaryl)benzotriazoles and evaluation of their photochemical behavior as potential UV-filters"; Molecules; 2010, vol. 15, pp. 6205-6216.

Database WPI; Week 199417, 1994, Thomson Scientific, London, GB; AN 1994-141126, XP002768707 and JPH0688066; Toray Ind., Inc.; Abstract translation only.

* cited by examiner

UV-ABSORBING VINYLIC MONOMERS AND USES THEREOF

This application claims the benefits under 35 USC § 119 (e) of U.S. provisional application No. 62/298,137 filed 22 Feb. 2016, herein incorporated by reference in its entirety.

This invention is related to water-soluble vinylic monomers capable of absorbing ultra-violet (UV) radiation and optionally high-energy-violet (HEVL) radiation and their uses for producing hydrogel contact lenses capable of blocking ultra-violet ("UV") radiation and optionally (but preferably) violet radiation with wavelengths from 380 nm to 440 nm from a water-based hydrogel lens formulation.

BACKGROUND

Most commercially-available hydrogel contact lenses are produced according to a conventional cast molding technique involving use of disposable plastic molds and a mixture of vinylic monomers and crosslinking agents. There are several disadvantages with the conventional cast-molding technique. For example, a traditional cast-molding manufacturing process often includes lens extraction in which unpolymerized monomers must be removed from the lenses by using an organic solvent. Use of organic solvents can be costly and is not environmentally friendly. In addition, disposable plastic molds inherently have unavoidable dimensional variations, because, during injection-molding of plastic molds, fluctuations in the dimensions of molds can occur as a result of fluctuations in the production process (temperatures, pressures, material properties), and also because the resultant molds may undergo non-uniformly shrinking after the injection molding. These dimensional changes in the mold may lead to fluctuations in the parameters of contact lenses to be produced (peak refractive index, diameter, basic curve, central thickness etc.) and to a low fidelity in duplicating complex lens design.

The above described disadvantages encountered in a conventional cast-molding technique can be overcome by using the so-called Lightstream Technology™ (CIBA Vision), which involves (1) a lens-forming composition being substantially free of monomers and comprising a substantially-purified, water-soluble prepolymer with ethylenically-unsaturated groups, (2) reusable molds produced in high precision, and (3) curing under a spatial limitation of actinic radiation (e.g., UV), as described in U.S. Pat. Nos. 5,508,317, 5,583,163, 5,789,464, 5,849,810, 6,800,225, and 8,088,313. Lenses produced according to the Lightstream Technology™ can have high consistency and high fidelity to the original lens design, because of use of reusable, high precision molds. In addition, contact lenses with high quality can be produced at relatively lower cost due to the short curing time, a high production yield, and free of lens extraction and in an environmentally friendly manner because of use of water as solvent for preparing lens formulations. However, the Lightstream Technology™ has not been applied to make contact lenses capable of absorbing ultra-violet (UV) lights (between 280 nm and 380 nm) and optionally high-energy violet lights (HEVL) (between 380 nm and 440 nm), largely because commercially-available polymerizable UV-absorbing vinylic monomers and those disclosed in U.S. Pat. Nos. 4,612,358, 4,528,311, 4,716,234, 7,803,359, 8,153,703, 8,232,326, and 8,585,938 (herein incorporated by reference in their entireties) are not water-soluble and cannot be used in the production of contact lenses from a water-based lens formulation.

Therefore, there are still needs for a new water-soluble UV-absorbing vinylic monomer or a new water-soluble UV/HEVL-absorbing vinylic monomer for making UV-absorbing or UV/HEVL-absorbing contact lenses from a water-based lens formulation.

SUMMARY

In one aspect, the invention provides an UV-absorbing vinylic monomer comprising a moiety of benzophenone or benzotriazole, one or more hydrophilic moieties for rendering the UV-absorbing vinylic monomer water-soluble, and a (meth)acryloyl group.

In another aspect, the invention provides a method for producing UV-absorbing contact lenses from an aqueous lens formulation comprising at least one water-soluble, UV-absorbing vinylic monomer of the invention.

The invention provides in a further aspect hydrogel contact lenses comprising monomeric units of an UV-absorbing vinylic monomer of the invention.

BRIEF DESCRIPTIONS OF DRAWINGS

FIG. 1 shows the UV-visible absorption spectra of a preferred water-soluble UV-absorbing vinylic monomer of the invention in a protected form (curve 1) and an unprotected form (curve 2).

Figure 2:
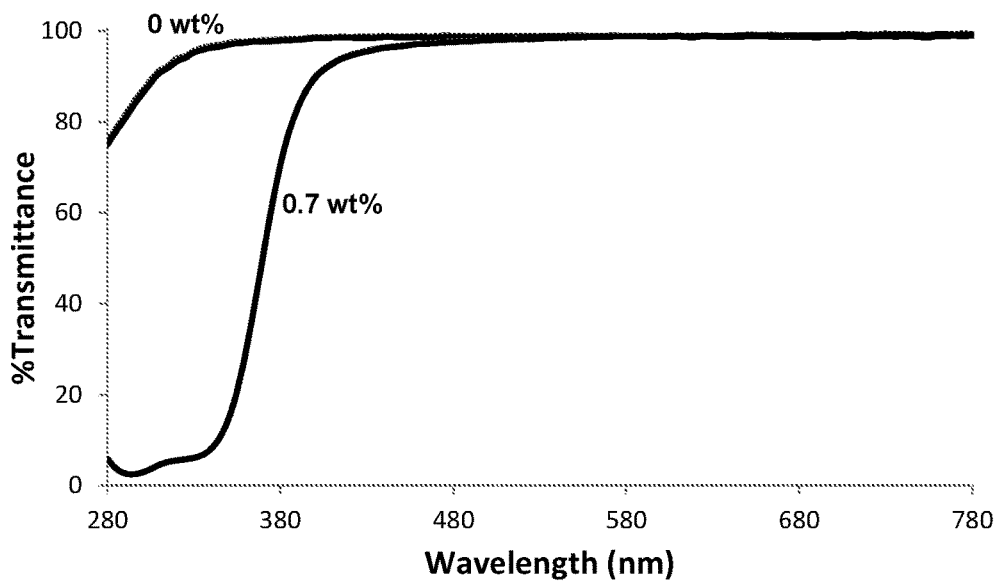

FIG. 2 shows the UV-visible transmission spectra of contact lenses: 0 wt %—control contact lens prepared from a lens formulation having 0 wt % of any UV-absorbing vinylic monomer; and 0.7 wt %—contact lens prepared from a lens formulation comprising about 0.7 wt % of a UV-absorbing vinylic monomer of the invention according to a preferred embodiment.

Figure 3:
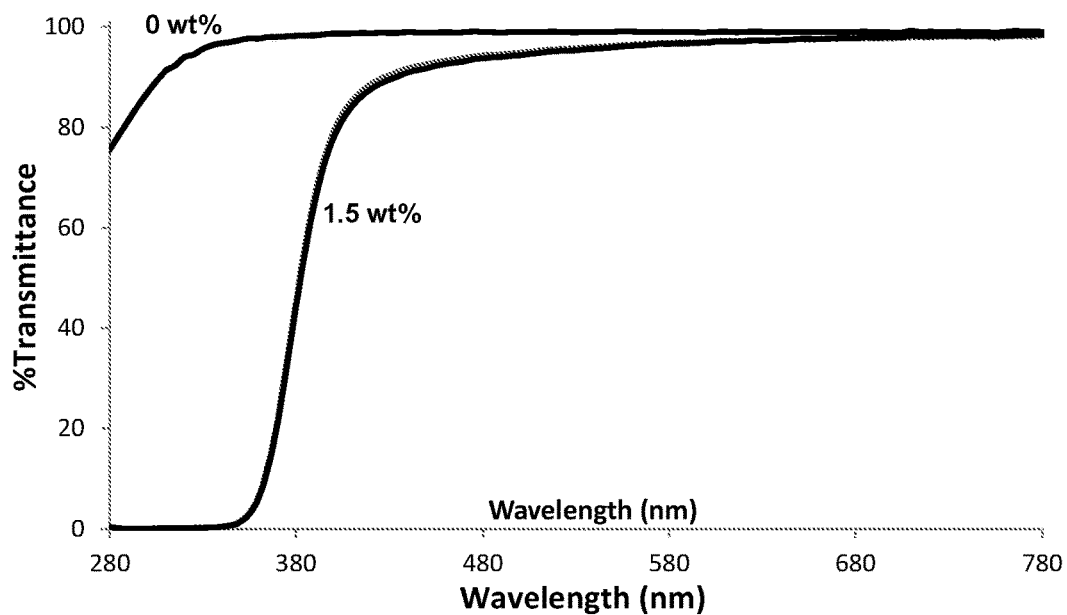

FIG. 3 shows the UV-visible transmission spectra of contact lenses: 0 wt %—control contact lens prepared from a lens formulation having 0 wt % of any UV-absorbing vinylic monomer; and 1.5 wt %—contact lens prepared from a lens formulation comprising about 1.5 wt % of a UV-absorbing vinylic monomer of the invention according to a preferred embodiment.

Figure 4:
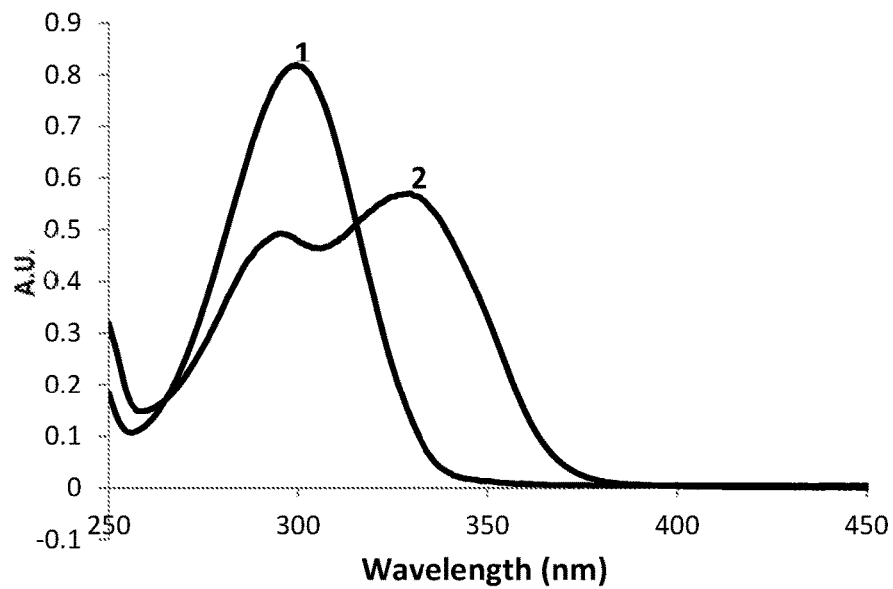

FIG. 4 shows the UV-visible absorption spectra of a preferred water-soluble UV-absorbing vinylic monomer of the invention in a protected form (curve 1) and an unprotected form (curve 2).

Figure 5:
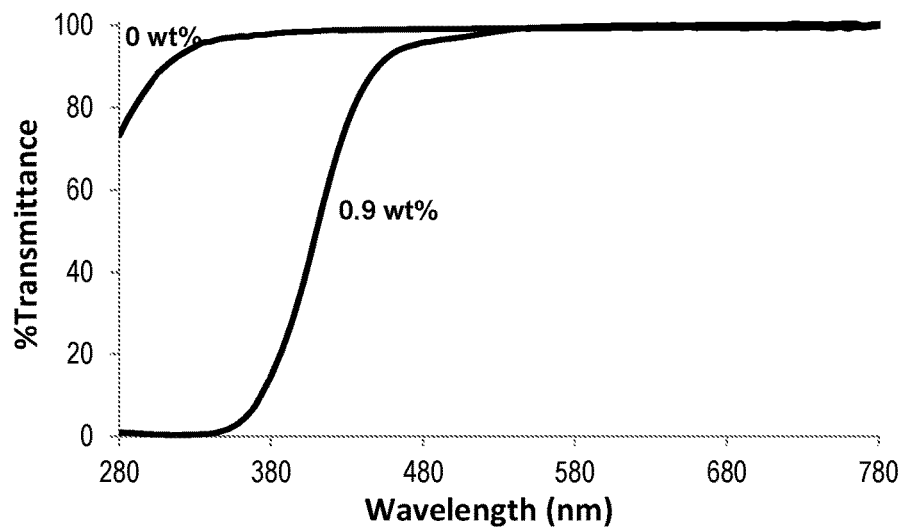

FIG. 5 shows the UV-visible transmission spectra of contact lenses: 0 wt %—control contact lens prepared from a lens formulation having 0 wt % of any UV-absorbing vinylic monomer; and 0.9 wt %—contact lens prepared from a lens formulation comprising about 0.9 wt % of a UV-absorbing vinylic monomer of the invention according to a preferred embodiment.

Figure 6:
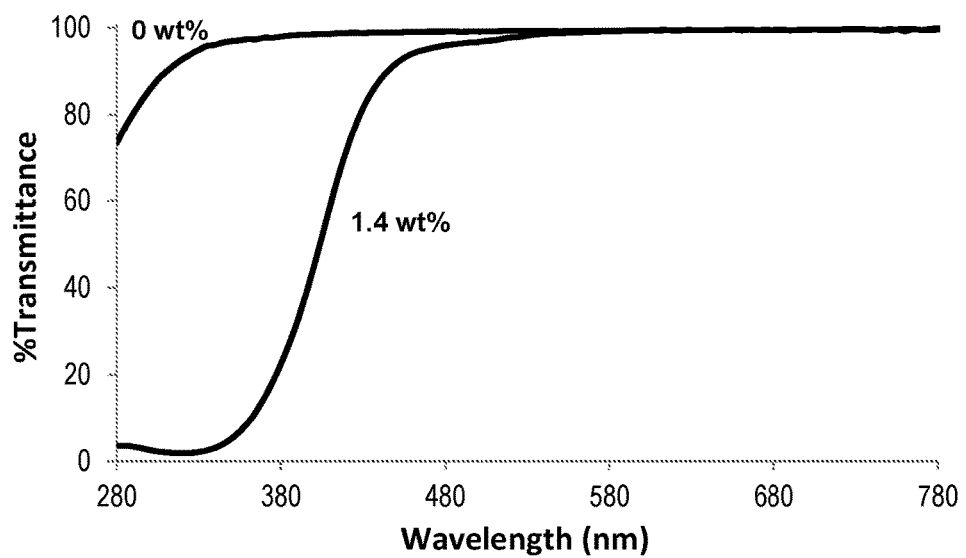

FIG. 6 shows the UV-visible transmission spectra of contact lenses: 0 wt %—control contact lens prepared from a lens formulation having 0 wt % of any UV-absorbing vinylic monomer; and 1.4 wt %—contact lens prepared from a lens formulation comprising about 1.4 wt % of a UV-absorbing vinylic monomer of the invention according to a preferred embodiment.

DETAILED DESCRIPTION

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term. The nomenclature used herein and the laboratory procedures described below are those well-known and commonly employed in the art.

"About" as used herein means that a number referred to as "about" comprises the recited number plus or minus 1-10% of that recited number.

"Optional" or "optionally" means that the subsequently described event or circumstance can or cannot occur, and that the description includes instances where the event or circumstance occurs and instances where it does not.

A "contact Lens" refers to a structure that can be placed on or within a wearer's eye. A contact lens can correct, improve, or alter a user's eyesight, but that need not be the case.

As used in this application, the term "hydrogel" or "hydrogel material" refers to a crosslinked polymeric material which is insoluble in water, but can hold at least 10 percent by weight of water in its three-dimensional polymer networks (i.e., polymer matrix) when it is fully hydrated.

A "vinylic monomer" refers to a compound that has one sole ethylenically-unsaturated group and is soluble in a solvent.

The term "soluble", in reference to a compound or material in a solvent, means that the compound or material can be dissolved in the solvent to give a solution with a concentration of at least about 0.1% by weight at room temperature (i.e., from about 20° C. to about 30° C.).

The term "insoluble", in reference to a compound or material in a solvent, means that the compound or material can be dissolved in the solvent to give a solution with a concentration of less than 0.005% by weight at room temperature (as defined above).

The term "ethylenically unsaturated group" is employed herein in a broad sense and is intended to encompass any groups containing at least one >C=C< group. Exemplary ethylenically unsaturated groups include without limitation (meth)acryloyl

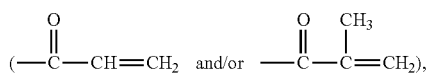

allyl, vinyl

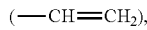

1-methylethenyl

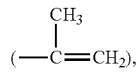

styrenyl, or the likes.

The term "(meth)acryloylamido group" refers to a radical of

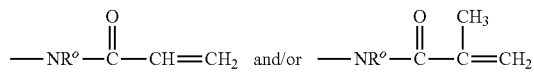

in which R° is hydrogen or a $C_1$-$C_6$ alkyl.

The term "(meth)acrylamide" refers to methacrylamide and/or acrylamide.

The term "(meth)acrylate" refers to methacrylate and/or acrylate.

A "hydrophilic vinylic monomer", as used herein, refers to a vinylic monomer which can be polymerized to form a homopolymer that is water-soluble or can absorb at least 10 percent by weight of water.

A "hydrophobic vinylic monomer" refers to a vinylic monomer which can be polymerized to form a homopolymer that is insoluble in water and can absorb less than 10 percent by weight of water.

"UVA" refers to radiation occurring at wavelengths between 315 and 380 nanometers; "UVB" refers to radiation occurring between 280 and 315 nanometers; "Violet" refers to radiation occurring at wavelengths between 380 and 440 nanometers.

"UVA transmittance" (or "UVA % T"), "UVB transmittance" or "UVB % T", and "violet-transmittance" or "Violet % T" are calculated by the following formula $$UVA\ \%\ T = \frac{\text{Average \% Transmission between 315 and 380 nm}}{\text{Luminescence \% }T} \times 100$$

$$UVB\ \%\ T = \frac{\text{Average \% Transmission between 280 and 315 nm}}{\text{Luminescence \% }T} \times 100$$

$$\text{Violet }\%\ T = \frac{\text{Average \% Transmission between 380 and 440 nm}}{\text{Luminescence \% }T} \times 100$$

in which Luminescence % T is the ratio of luminous flux transmitted by the lens to the incident luminous flux (ISO 13666:1998).

As used in this application, the term "macromer" or "prepolymer" refers to a medium and high molecular weight compound or polymer that contains two or more ethylenically unsaturated groups. Medium and high molecular weight typically means average molecular weights greater than 700 Daltons.

As used in this application, the term "vinylic crosslinker" refers to a compound having at least two ethylenically unsaturated groups. A "vinylic crosslinking agent" refers to a vinylic crosslinker having a molecular weight of about 700 Daltons or less.

As used in this application, the term "polymer" means a material formed by polymerizing/crosslinking one or more monomers or macromers or prepolymers.

As used in this application, the term "molecular weight" of a polymeric material (including monomeric or macromeric materials) refers to the weight-average molecular weight unless otherwise specifically noted or unless testing conditions indicate otherwise.

The term "alkyl" refers to a monovalent radical obtained by removing a hydrogen atom from a linear or branched alkane compound. An alkyl group (radical) forms one bond with one other group in an organic compound.

The term "alkylene divalent group" or "alkylene diradical" or "alkyl diradical" interchangeably refers to a divalent radical obtained by removing one hydrogen atom from an alkyl. An alkylene divalent group forms two bonds with other groups in an organic compound.

The term "alkyl triradical" refers to a trivalent radical obtained by removing two hydrogen atoms from an alkyl. A alkyl triradical forms three bonds with other groups in an organic compound.

The term "alkoxy" or "alkoxyl" refers to a monovalent radical obtained by removing the hydrogen atom from the hydroxyl group of a linear or branched alkyl alcohol. An alkoxy group (radical) forms one bond with one other group in an organic compound.

In this application, the term "substituted" in reference to an alkyl diradical or an alkyl radical means that the alkyl diradical or the alkyl radical comprises at least one substituent which replaces one hydrogen atom of the alkyl diradical or the alkyl radical and is selected from the group consisting of hydroxy (—OH), carboxy (—COOH), —NH$_2$, sulfhydryl (—SH), $C_1$-$C_4$ alkyl, $C_1$-$C_4$ alkoxy, $C_1$-$C_4$ alkylthio (alkyl sulfide), $C_1$-$C_4$ acylamino, $C_1$-$C_4$ alkylamino, di-$C_1$-$C_4$ alkylamino, halogen atom (Br or Cl), and combinations thereof.

A "photoinitiator" refers to a chemical that initiates free radical crosslinking/polymerizing reaction by the use of light.

In this application, a "UV-absorbing vinylic monomer" refers to a vinylic monomer comprising an ethylenically-unsaturated group and an UV-absorbing moiety (benzophenone or benzotriazole moiety) which can absorb or screen out UV radiation in the range from 200 nm to 400 nm as understood by a person skilled in the art.

A "spatial limitation of actinic radiation" refers to an act or process in which energy radiation in the form of rays is directed by, for example, a mask or screen or combinations thereof, to impinge, in a spatially restricted manner, onto an area having a well-defined peripheral boundary. A spatial limitation of UV/visible radiation is obtained by using a mask or screen having a radiation (e.g., UV and/or visible light) permeable region, a radiation (e.g., UV and/or visible light) impermeable region surrounding the radiation-permeable region, and a projection contour which is the boundary between the radiation-impermeable and radiation-permeable regions, as schematically illustrated in the drawings of U.S. Pat. No. 6,800,225 (FIGS. 1-11), and U.S. Pat. No. 6,627,124 (FIGS. 1-9), U.S. Pat. No. 7,384,590 (FIGS. 1-6), and U.S. Pat. No. 7,387,759 (FIGS. 1-6), all of which are incorporated by reference in their entireties. The mask or screen allows to spatially projects a beam of radiation (e.g., UV radiation and/or visible radiation) having a cross-sectional profile defined by the projection contour of the mask or screen. The projected beam of radiation (e.g., UV radiation and/or visible radiation) limits radiation impinging on a lens formulation located in the path of the projected beam from the first molding surface to the second molding surface of a mold. The resultant contact lens comprises an anterior surface defined by the first molding surface, an opposite posterior surface defined by the second molding surface, and a lens edge defined by the sectional profile of the projected UV and/or visible beam (i.e., a spatial limitation of radiation). The radiation used for the crosslinking is radiation energy, especially UV radiation (and/or visible radiation), gamma radiation, electron radiation or thermal radiation, the radiation energy preferably being in the form of a substantially parallel beam in order on the one hand to achieve good restriction and on the other hand efficient use of the energy.

The term "modulus" or "elastic modulus" in reference to a contact lens or a material means the tensile modulus or Young's modulus which is a measure of the stiffness of a contact lens or a material. The modulus can be measured using a method in accordance with ANSI Z80.20 standard. A person skilled in the art knows well how to determine the elastic modulus of a silicone hydrogel material or a contact lens. For example, all commercial contact lenses have reported values of elastic modulus.

In general, the invention is directed to a class of UV-absorbing vinylic monomers which are soluble in water due to the presence of one or more hydrophilic moieties, and can be used, in a water-based hydrogel lens formulation for making UV-absorbing hydrogel contact lenses, in particularly, according to the Lightstream Technology™. Any unreacted UV-absorbing vinylic monomer can be efficiently removed by water or an aqueous solution as extraction solvent, if necessary.

In one aspect, the present invention provides a UV-absorbing vinylic monomer of any one of formula (I) to (VII)

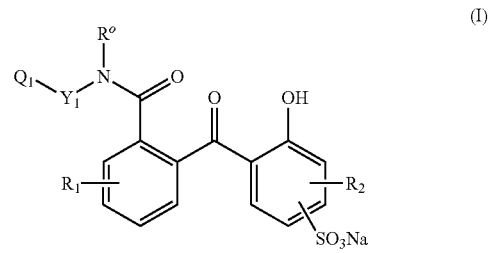

(I)

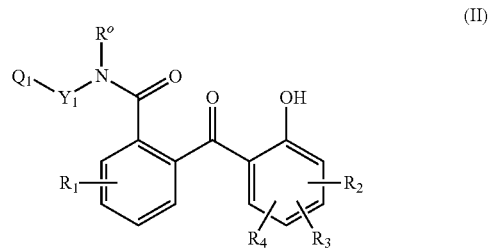

(II)

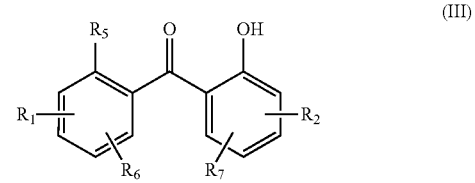

(III)

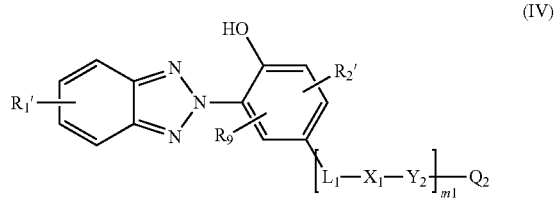

(IV)

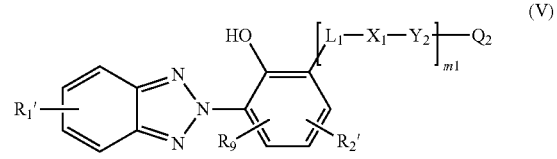

(V)

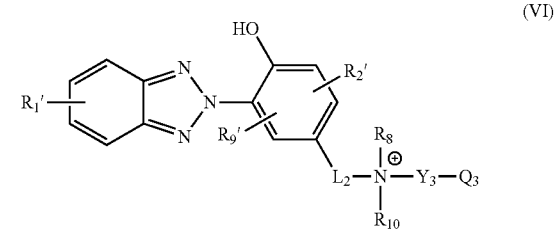

(VI)

-continued

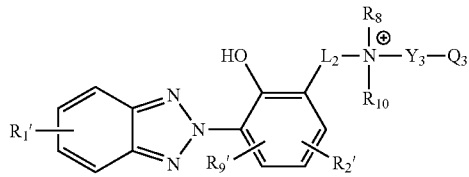
(VII)

in which:

R° is H, CH₃ or C₂H₅;

R₁, R₂ and R₂' independent of one other are H, CH₃, CCl₃, CF₃, Cl, Br, OH, OCH₃, or NR'R" in which R' and R" independent of each other are H or C₁-C₄ alkyl;

R₁' independent of each other are H, CH₃, CCl₃, CF₃, Cl, Br, OH, OCH₃, SO₃H, SO₃Na, or NR'R" in which R' and R" independent of each other are H or C₁-C₄ alkyl;

R₃ and R₄ independent of each other are H or a first hydrophilic group which is *—CH₂—(OC₂H₄)_{n1}—OCH₃, *—CH₂—(OC₂H₄)_{n1}—OH,

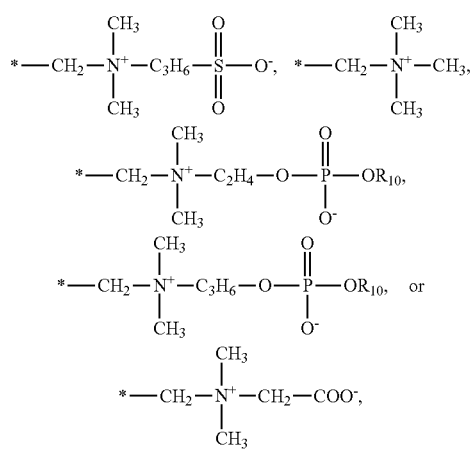

provided that at least one of R₃ and R₄ is the first hydrophilic group;

R₅ is H, *—COOH, *—CONH—C₂H₄—(OC₂H₄)_{n1}—OCH₃, or *—CONH—C₂H₄—(OC₂H₄)_{n1}—OH;

one of R₆ and R₇ is H or a second hydrophilic group which is *—CH₂—(OC₂H₄)_{n1}—OCH₃, *—CH₂—(OC₂H₄)_{n1}—OH,

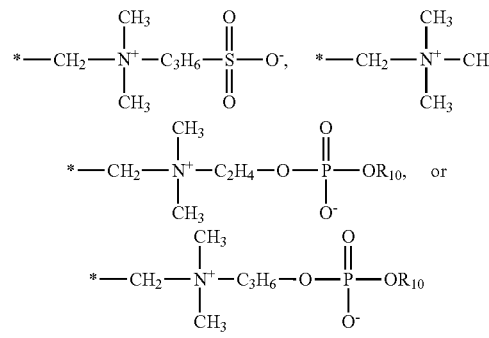

while the other of R₆ and R₇ is

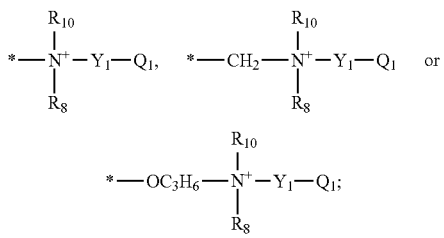

R₈ is CH₃, C₂H₅,

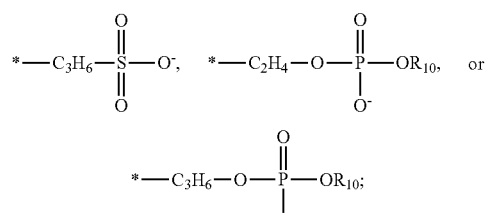

R₉ is SO₃Na,

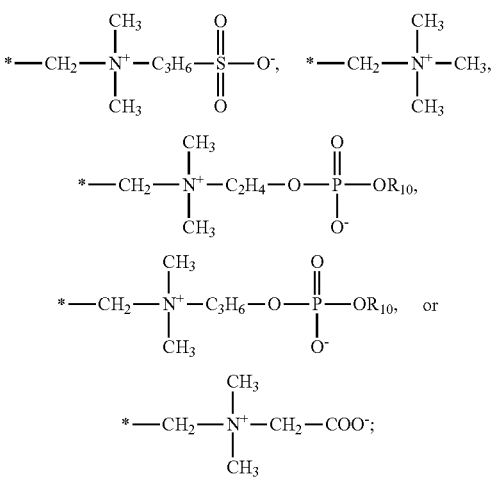

R₉' is H, SO₃Na,

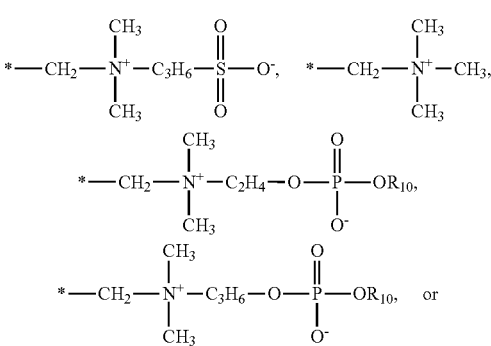

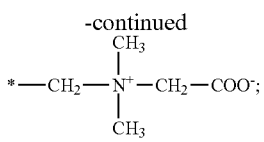

$R_{10}$ is methyl or ethyl;
L1 is a direct bond or a linkage of

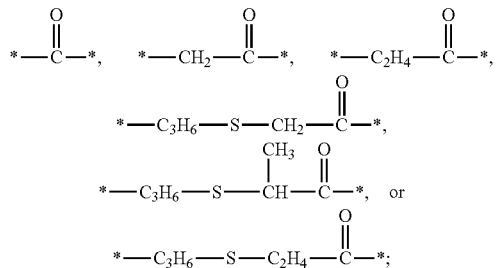

L2 is a linkage of *—CH$_2$—*, *—C$_2$H$_4$—*, *—C$_3$H$_6$—*, *—C$_3$H$_6$—S—C$_2$H$_4$—*, *—C$_3$H$_6$—S—C$_3$H$_6$—*, or

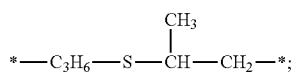

X1 is O or NR°; and
Y$_1$, Y$_2$, and Y$_3$ independent of one another are a C$_2$-C$_4$ alkylene divalent radical;
Q1, Q2, and Q3 independent of one another are a (meth) acryloylamido or (meth)acryloyloxy group;
m1 is zero or 1, provided that if m1 is zero, then Q$_2$ is a (meth)acryloylamido group; and
n1 is an integer of 2 to 20 (preferably 3 to 15, more preferably 4 to 10).

Preferred examples of a UV-absorbing vinylic monomer of formula (I) include without limitation:

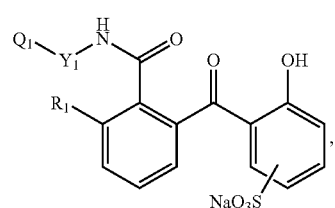

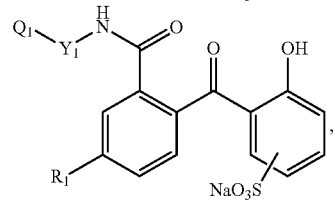

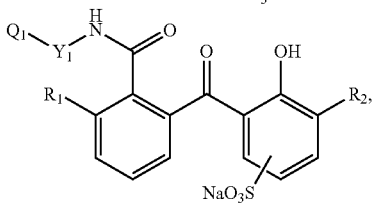

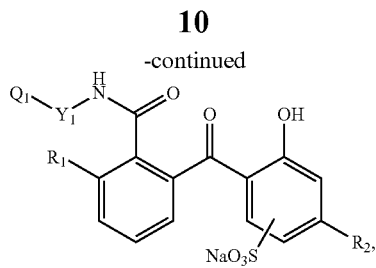

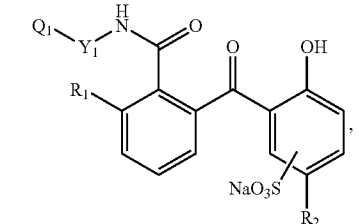

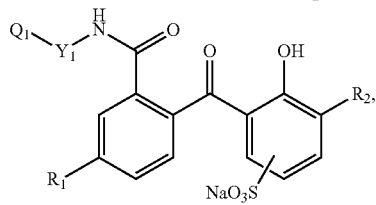

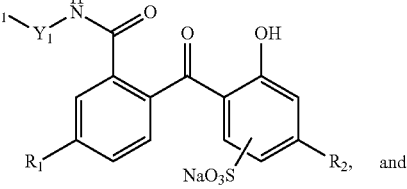, and

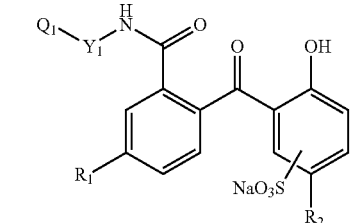

in which: Q$_1$ is (meth)acryloylamido or (meth)acryloyloxy group; Y$_1$ is an ethylene or propylene divalent radical; R$_1$ and R$_2$ independent of each other are H, CH$_3$, CCl$_3$, CF$_3$, Cl, Br, OH, OCH$_3$, or NR'R" in which R' and R" independent of each other are H, methyl or ethyl.

Preferred examples of a UV-absorbing vinylic monomer of formula (II) include without limitation:

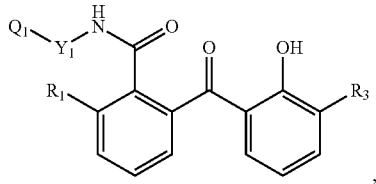

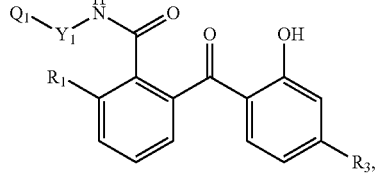

-continued
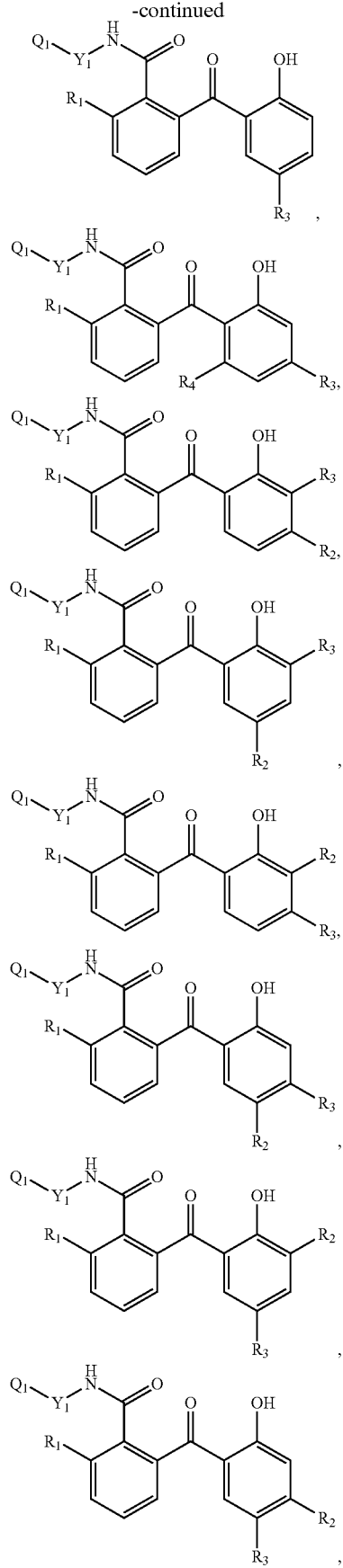
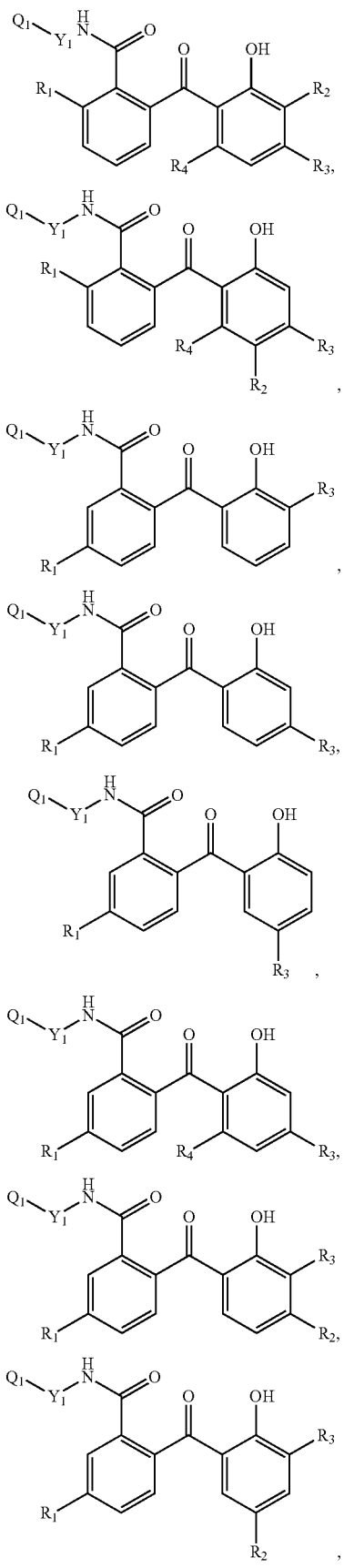

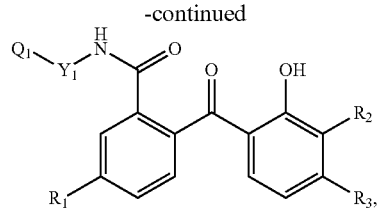

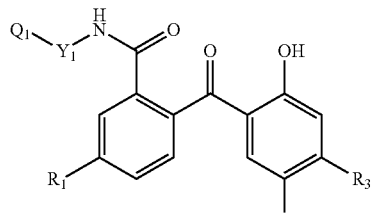

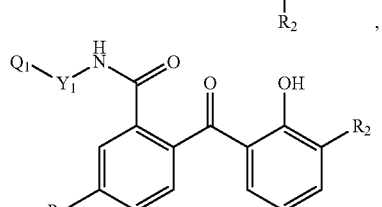

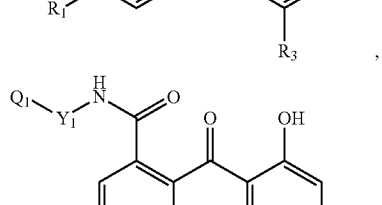

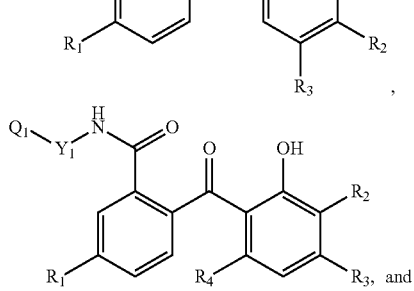

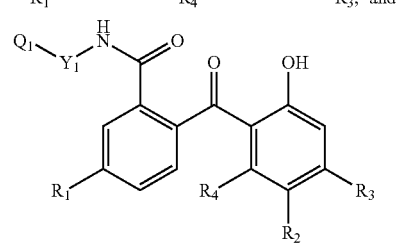

in which: $Q_1$ is (meth)acryloylamido or (meth)acryloyloxy group; $Y_1$ is an ethylene or propylene divalent radical; $R_1$ and $R_2$ independent of each other are $CH_3$, $CCl_3$, $CF_3$, Cl, Br, NR'R", OH, or $OCH_3$; R' and R" independent of each other are H, methyl or ethyl; $R_3$ and $R_4$ independent of each other are *—$CH_2$—$(OC_2H_4)_{n1}$—$OCH_3$, *—$CH_2$—$(OC_2H_4)_{n1}$—OH,

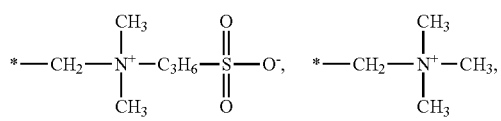

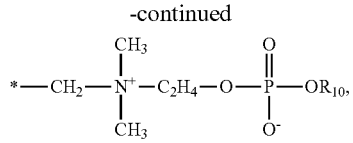

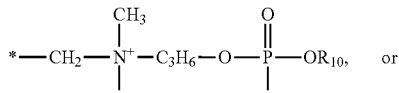

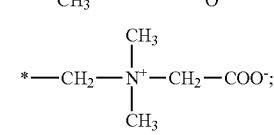 or $R_{10}$ is methyl or ethyl.

Preferred examples of a UV-absorbing vinylic monomer of formula (III) include without limitation:

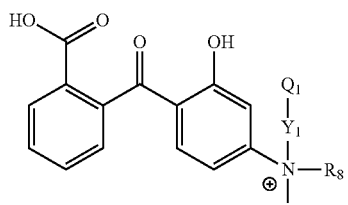

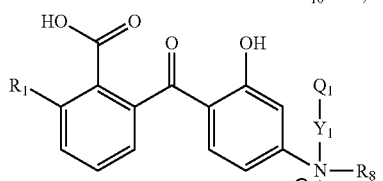

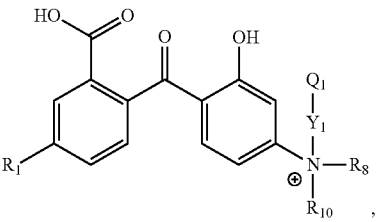

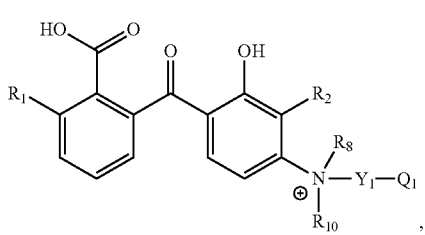

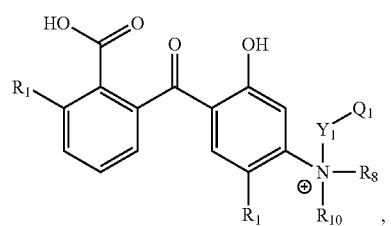

-continued
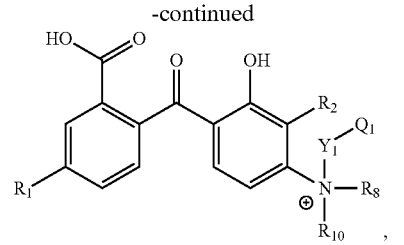
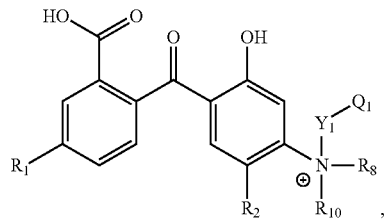
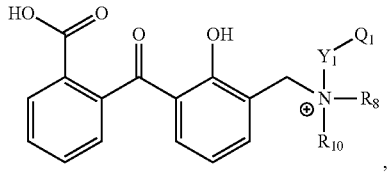
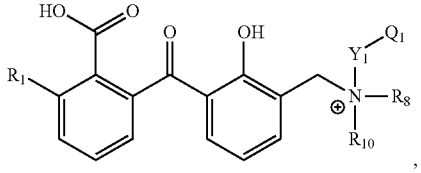
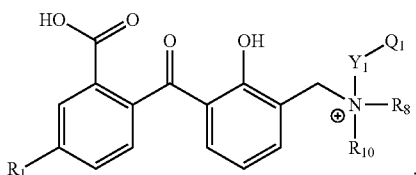
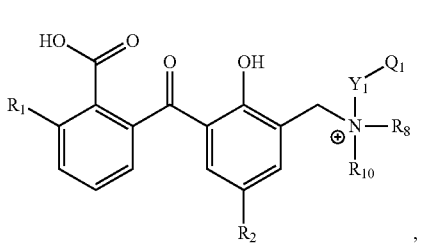
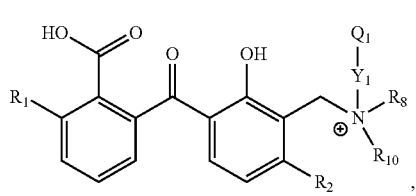
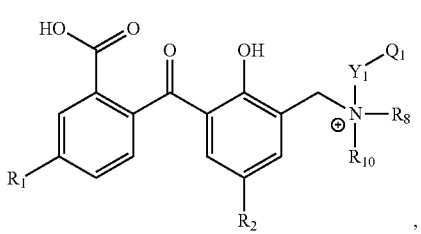
-continued
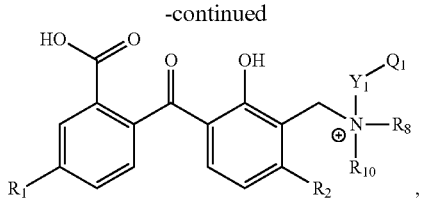
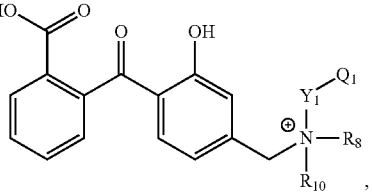
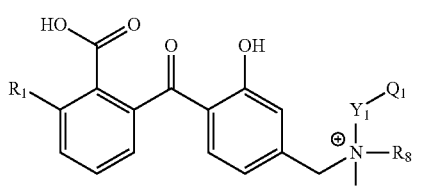
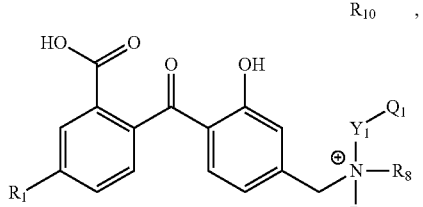
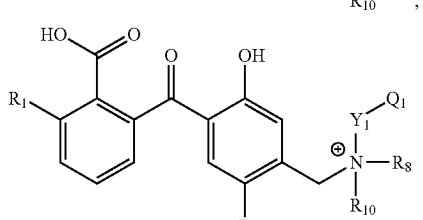
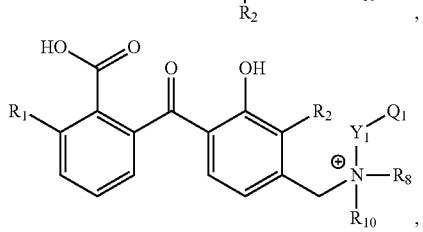
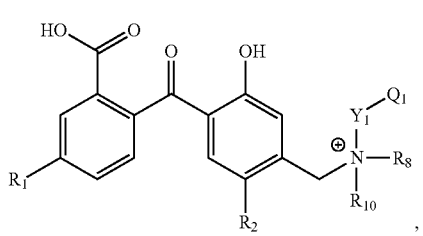
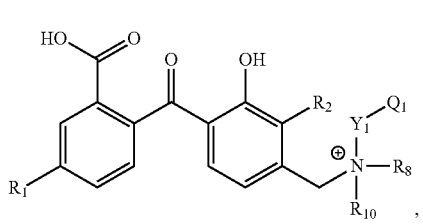

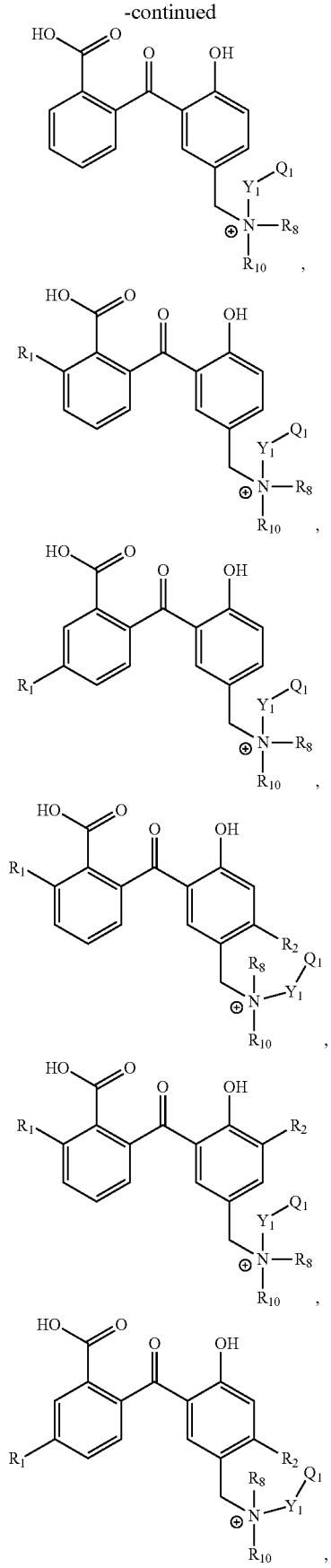
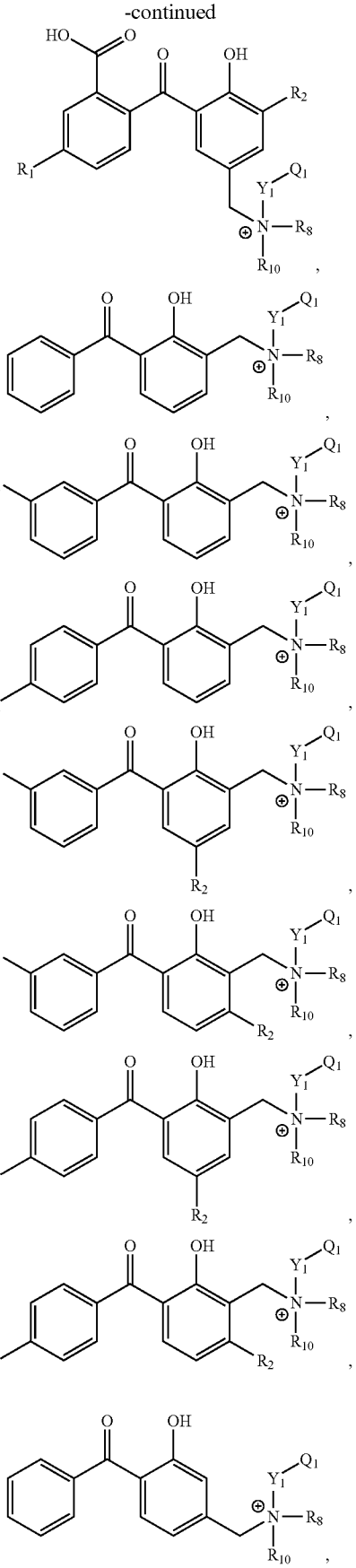

-continued
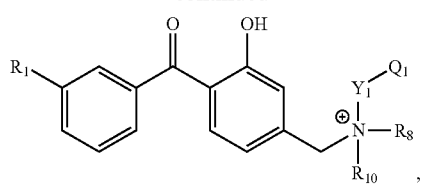
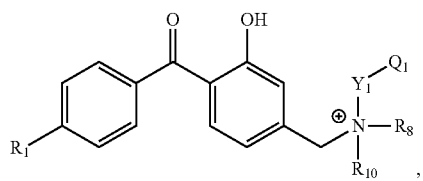
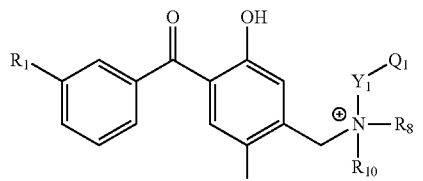
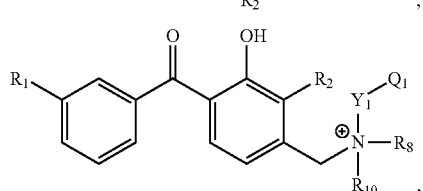
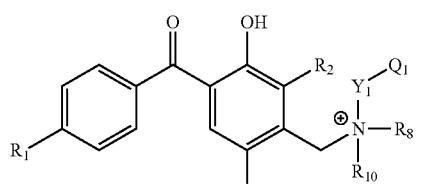
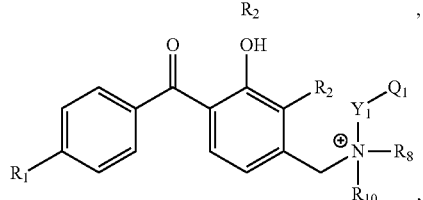
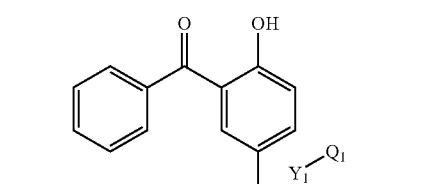
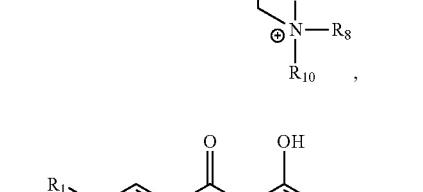
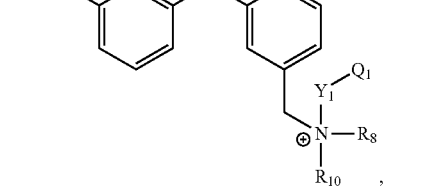
-continued
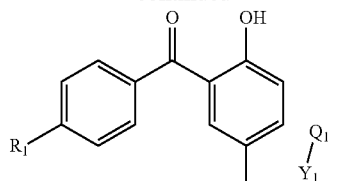
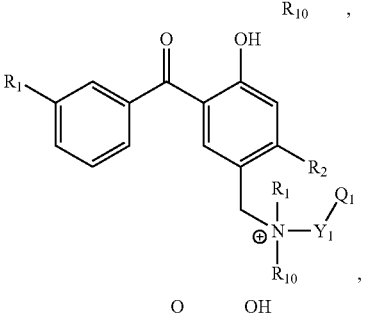
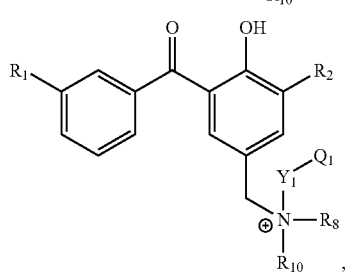
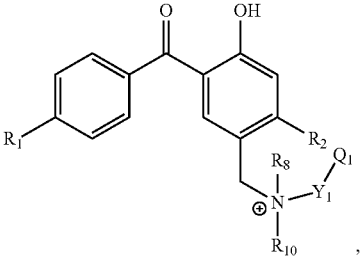
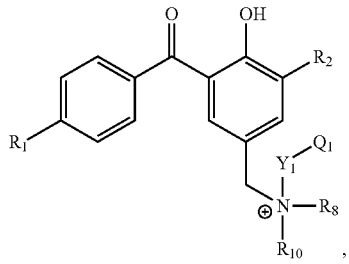
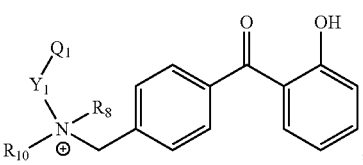
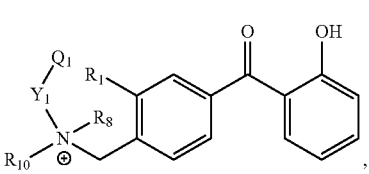

-continued

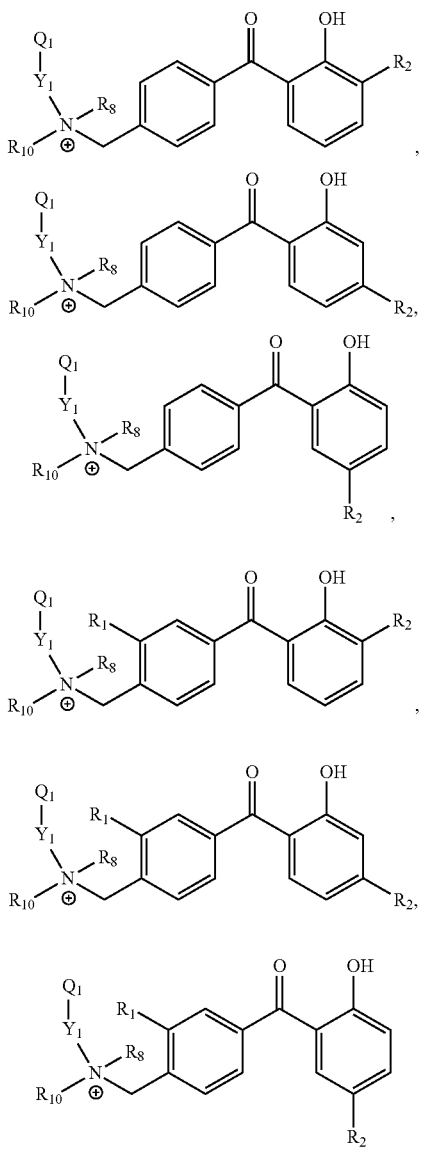

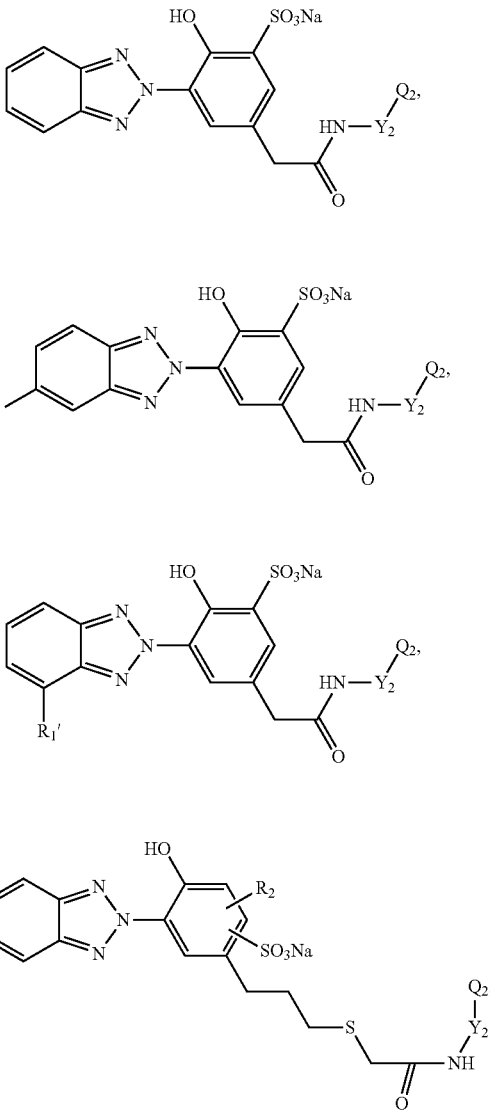

in which: $Q_1$ is (meth)acryloylamido or (meth)acryloyloxy group; $Y_1$ is an ethylene or propylene divalent radical; $R_1$ and $R_2$ independent of each other are $CH_3$, $CCl_3$, $CF_3$, Cl, Br, NR'R"OH, or $OCH_3$; in which R' and R" independent of each other are H or $C_1$-$C_4$ alkyl; $R_8$ is $CH_3$, $C_2H_5$,

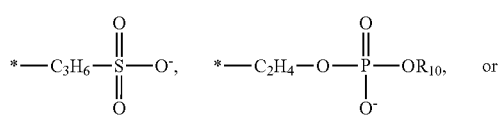

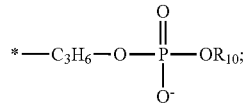

$R_{10}$ is methyl or ethyl.

Preferred examples of a UV-absorbing vinylic monomer of formula (IV) or (V) include without limitation:

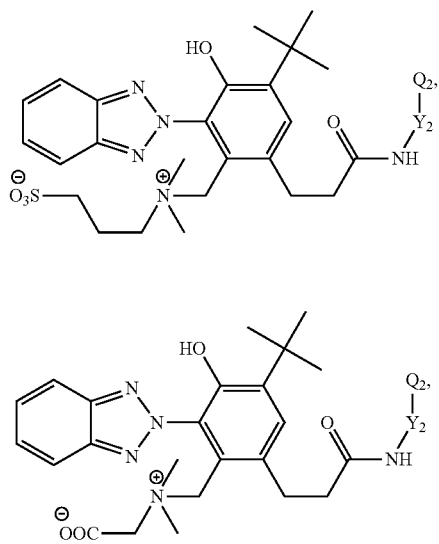

-continued

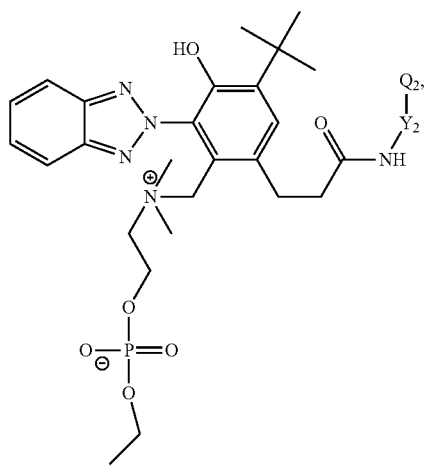

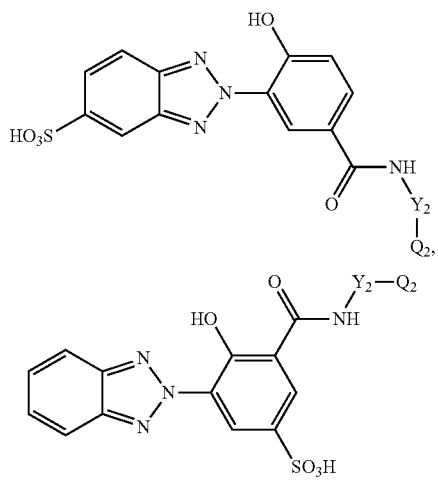

in which $R_1'$ is H, CH$_3$, CCl$_3$, CF$_3$, Cl, Br, NR'R" in which R' and R" independent of each other are H or C$_1$-C$_4$ alkyl, OH, or OCH$_3$; Q$_2$ is (meth)acryloylamido or (meth)acryloyloxy group; Y$_2$ is an ethylene or propylene divalent radical.

Preferred examples of a UV-absorbing vinylic monomer of formula (VI) or (VII) include without limitation:

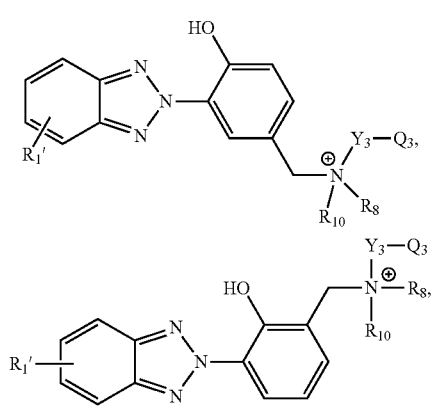

in which $R_1'$ is H, CH$_3$, CCl$_3$, CF$_3$, Cl, Br, F, OH, or OCH$_3$, NR'R" in which R' and R" independent of each other are H or C$_1$-C$_4$ alkyl, R$_8$ is CH$_3$, C$_2$H$_5$,

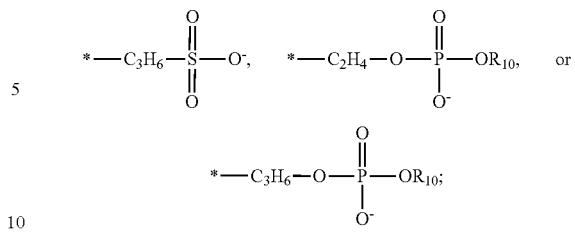

$R_{10}$ is methyl or ethyl; Q$_3$ is (meth)acryloylamido or (meth)acryloyloxy group; Y$_3$ is an ethylene or propylene divalent radical.

A UV-absorbing vinylic monomer of formula (I) defined above can be prepared according to procedures illustrated in Scheme 1:

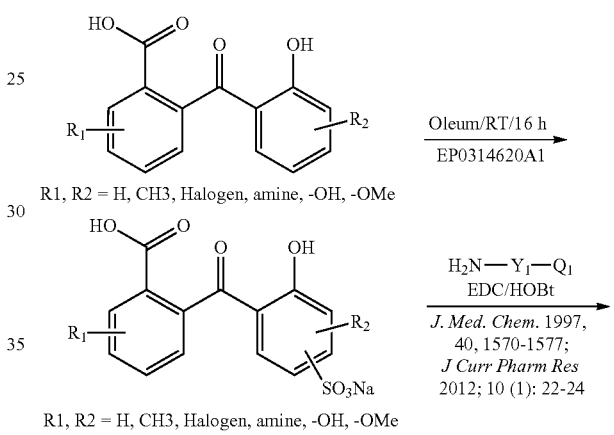

It is understood that in the 2$^{nd}$ step of Scheme 1 or 2 above, a vinylic monomer of H$_2$N—Y$_1$-Q$_1$ (as defined above) can be substituted with another vinylic monomer of HNR°—Y$_1$-Q$_1$ (as defined above) in which R° is CH$_3$ or C$_2$H$_5$ for making other UV-absorbing vinylic monomers of formula (I) or (II). Exemplary vinylic monomers of HNR°—Y$_1$-Q$_1$ (as defined above) include without limitation 2-(methylamino)ethyl (meth)acrylate, 2-(methylamino)ethyl (meth)acrylamide, N-Methyl-N-[2-(methylamino)ethyl] (meth)acrylamide, ethylaminoethyl (meth)acrylate, ethylaminoethyl (meth)acrylamide, methylaminopropyl (meth)acrylate, methylaminopropyl (meth)acrylamide, ethylaminopropyl (meth)acrylate, and ethylaminopropyl (meth)acrylamide.

A UV-absorbing vinylic monomer of formula (II) defined above can be prepared according to procedures illustrated in Scheme 2:

Scheme 2

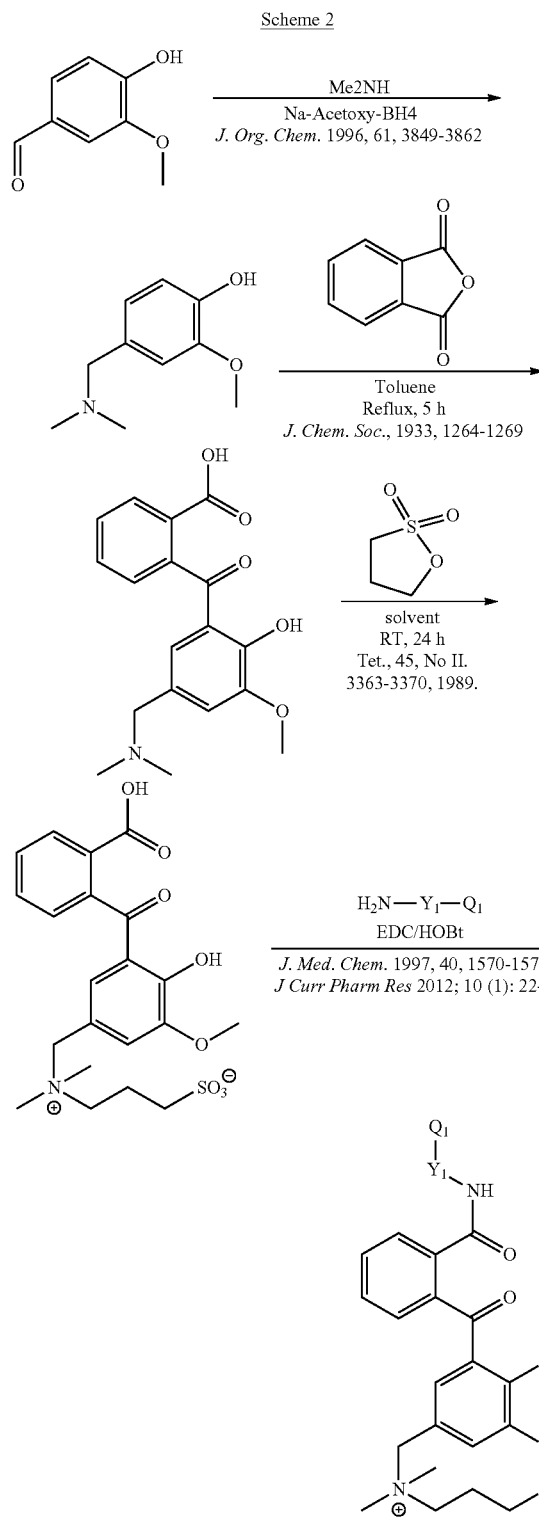

Scheme 3

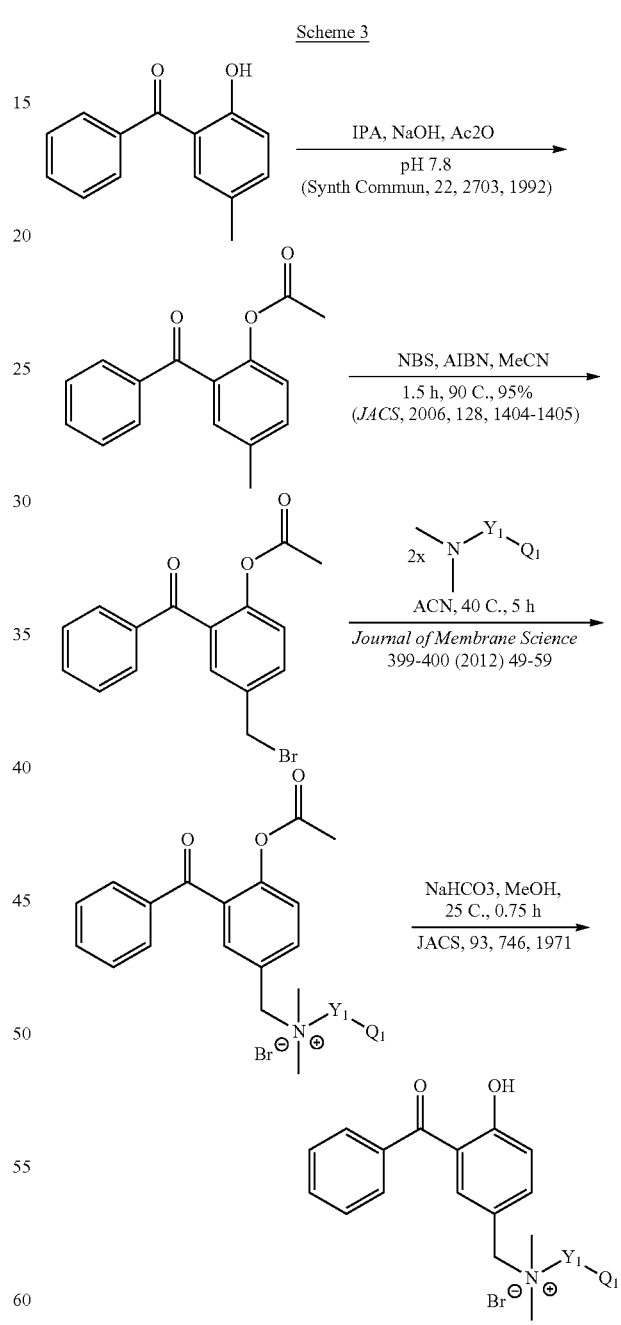

lene phosphate (e.g., methyl ethylene phosphate, ethyl ethylene phosphate, methyl propylene phosphate, or ethyl propylene phosphate), instead of 1,3-propane sultone, under conditions known to a person skilled in the art (Makromol. Chem., Rapid Commun. 3, 457-459 (1982), herein incorporated by reference in its entirety).

A UV-absorbing vinylic monomer of formula (III) defined above can be prepared according to procedures illustrated in Scheme 3:

It is understood that in the $2^{nd}$ step of Scheme 2 above, a vinylic monomer of $H_2N$—$Y_1$-$Q_1$ (as defined above) can be substituted with another vinylic monomer of $HNR°$—$Y_1$-$Q_1$ (as defined above) in which $R°$ is $CH_3$ or $C_2H_5$ for making other UV-absorbing vinylic monomers of formula (II). It is also understood that the $3^{rd}$ step of Scheme 2 can be altered to form a phosphocholine group by reacting an alkyl alky- It is also understood that Scheme 3 can be modified by replacing a vinylic monomer of $(CH_3)_2N$—$Y_1$-$Q_1$ can be substituted with another vinylic monomer of $HNR°$—$Y_1$-$Q_1$ in which $R°$ is $CH_3$ or $C_2H_5$ and then by adding one step of reacting the product of the $3^{rd}$ step with 1,3-propane sultone or an alkyl alkylene phosphate (e.g., methyl ethylene phosphate, ethyl ethylene phosphate, methyl propylene phosphate, or ethyl propylene phosphate) under conditions known to a person skilled in the art to form a UV-absorbing vinylic monomer of formula (III) with $R_8$ is a radical other than methyl.

Any 2-hydroxy-2'-carboxy benzophenones with substituents on either or both benzene rings can be used in the preparation of a UV-absorbing vinylic monomer of formula (I), (II) or (III). A person knows how to prepare a 2-hydroxy-2'-carboxy benzophenones with substituents from a substituted or unsubstituted phthalic anhydride and a substituted or unsubstituted phenol (see, e.g., U.S. Pat. No. 5,925,787, herein incorporated in reference in its entirety).

It is understood that in the $2^{nd}$ step of Scheme 2 any 3- and 4-substituted phthalic anhydride can be used to react with any mono- or di-substituted phenol to obtain a UV-absorbing vinylic monomer of formula (I), (II) or (III). Various 3- and 4-substituted phthalic anhydrides are commercially available or can be prepared according to the procedures described in *J. Chem. Soc., Perkin Trans.* (1977), 1: 2030-2036 (herein incorporated by reference in its entirety).

A UV-absorbing vinylic monomer of formula (IV) or (V) defined above can be prepared according to procedures illustrated in any one of Schemes 4 to 7:

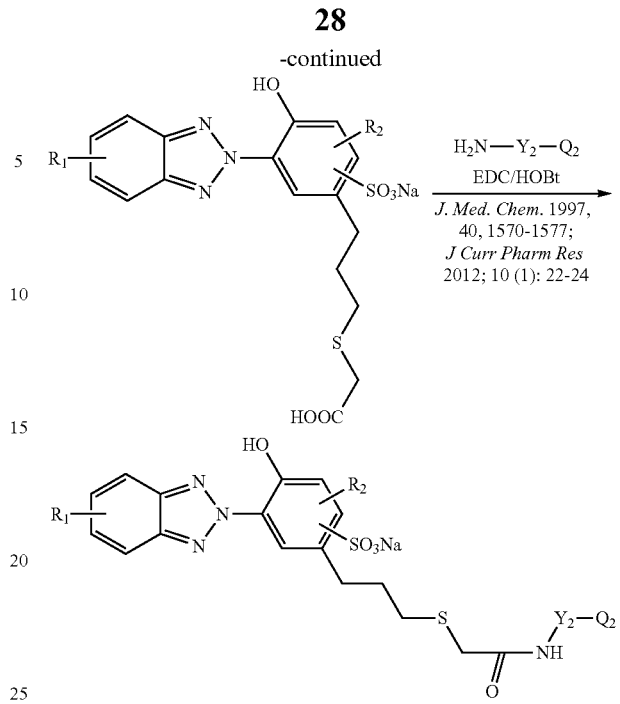

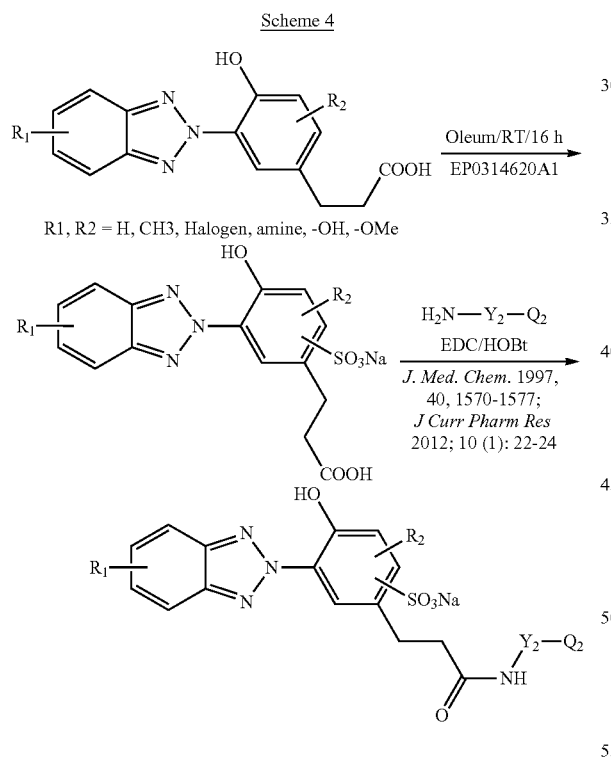

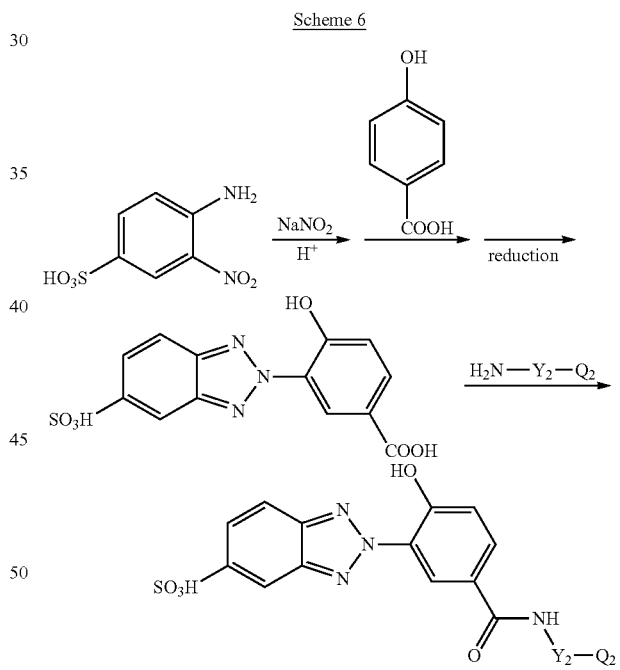

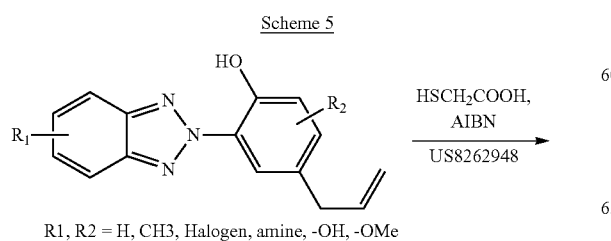

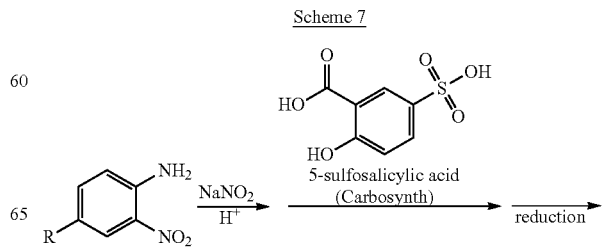

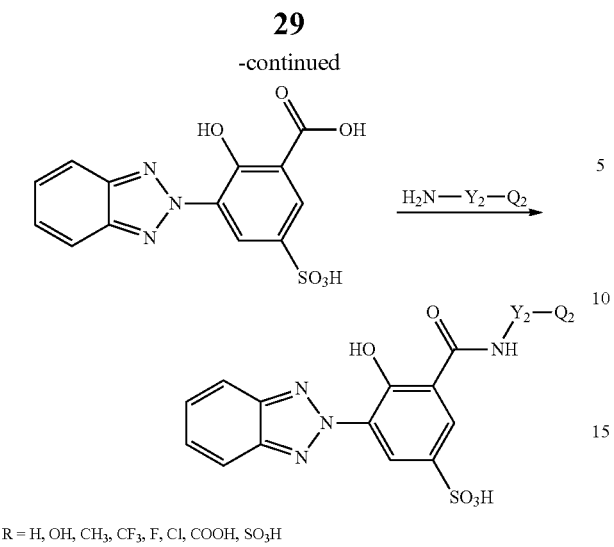
R = H, OH, CH₃, CF₃, F, Cl, COOH, SO₃H
A UV-absorbing vinylic monomer of formula (VI) or (VII) defined above can be prepared according to procedures illustrated in Scheme 8 or 9:
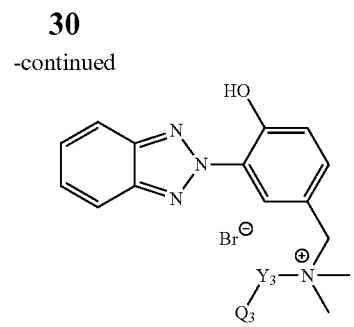
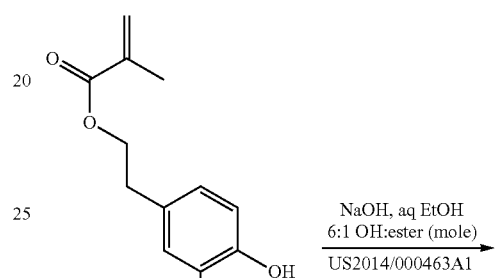
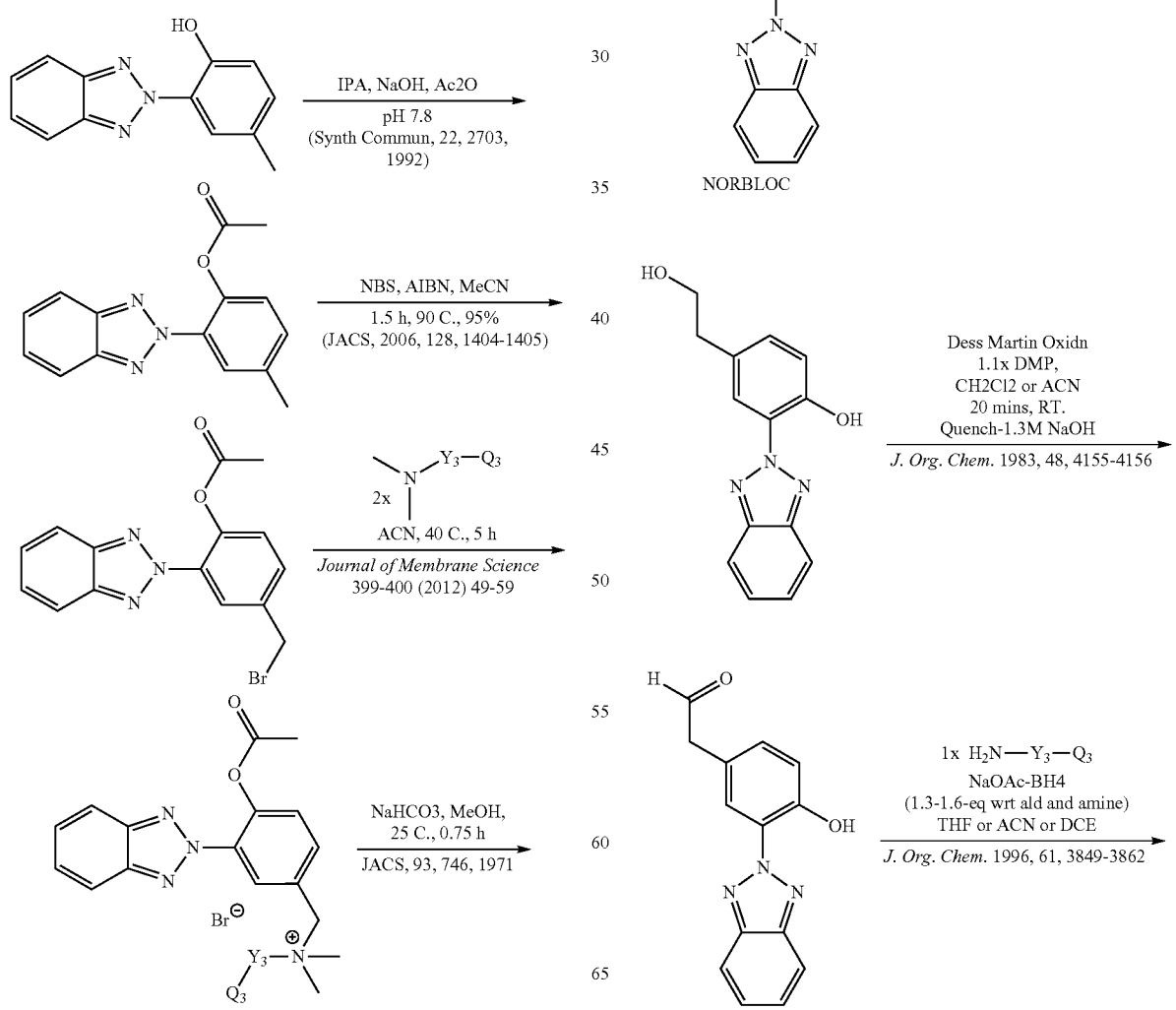

-continued

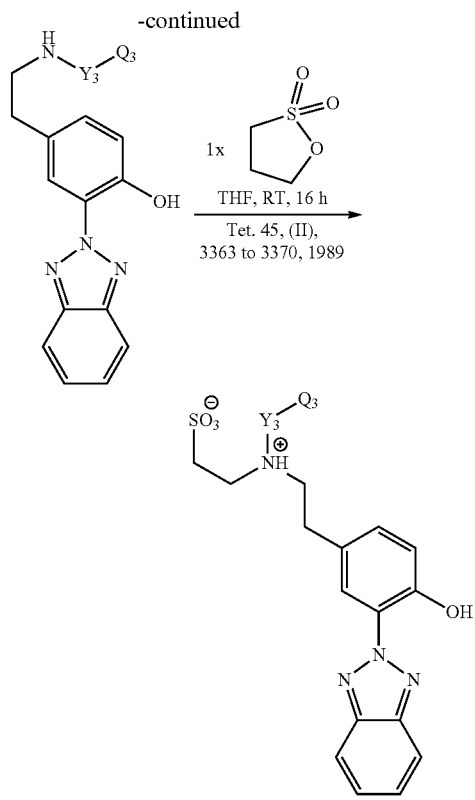

Any benzotriazoles with substituents can be used in the preparation of a vinylic monomer of any one of formula (IV) to (VII). A person knows how to prepare a benzotriazole with different substituents according to a known procedure (see, e.g., U.S. Pat. No. 8,262,948, herein incorporated in reference in its entirety).

A water-soluble UV-absorbing vinylic monomer of the invention described above can find particular uses in making UV-absorbing medical devices, preferably ophthalmic devices, more preferably intraocular lenses, even more preferably contact lenses.

In another aspect, the invention provides a method for producing UV-absorbing contact lenses, comprising the steps of: (1) obtaining a lens formulation comprising (a) (from about 0.1% to about 4% by weight of, preferably from about 0.2% to about 3.0% by weight of, more preferably from about 0.4% to about 2% by weight of, even more preferably from about 0.6% to about 1.5% by weight of) a UV-absorbing vinylic monomer of any one of formula (I) to (VII) (as defined above), (b) (from about 0.1% to about 2.0% by weight of, preferably from about 0.25% to about 1.75% by weight of, more preferably from about 0.5% to about 1.5% by weight of, even more preferably from about 0.75% to about 1.25% by weight of) at least free-radical initiator, and (c) at least one polymerizable components selected from the group consisting of a hydrophilic vinylic monomer, a water-soluble silicone-free prepolymer, a silicone-containing prepolymer, a non-silicone hydrophobic vinylic monomer, a siloxane-containing vinylic monomer, a siloxane-containing vinylic macromer, a vinylic crosslinking agent, and combinations thereof; (2) introducing the lens formulation into a mold for making a soft contact lens, wherein the mold has a first mold half with a first molding surface defining the anterior surface of a contact lens and a second mold half with a second molding surface defining the posterior surface of the contact lens, wherein said first and second mold halves are configured to receive each other such that a cavity is formed between said first and second molding surfaces; and (3) curing thermally or actinically the lens formulation in the mold to form the UV-absorbing contact lens, wherein the formed UV-absorbing contact lens is characterized by having the UVB transmittance of about 10% or less (preferably about 5% or less, more preferably about 2.5% or less, even more preferably about 1% or less) between 280 and 315 nanometers and a UVA transmittance of about 30% or less (preferably about 20% or less, more preferably about 10% or less, even more preferably about 5% or less) between 315 and 380 nanometers and and optionally (but preferably) a Violet transmittance of about 60% or less, preferably about 50% or less, more preferably about 40% or less, even more preferably about 30% or less) between 380 nm and 440 nm.

In accordance with the invention, a free-radical initiator can be a free-radical thermal initiator or a free-radical photoinitiator.

Any thermal free-radical initiators can be used in the invention. Examples of suitable thermal initiators include, but are not limited to, 2,2'-azobis (2,4-dimethylpentanenitrile), 2,2'-azobis (2-methylpropanenitrile), 2,2'-azobis (2-methylbutanenitrile), peroxides such as benzoyl peroxide, and the like. Preferably, the thermal initiator is 2,2'-azobis(isobutyronitrile) (AIBN).

Any free-radical photoinitiators, which can absorb radiation in the range from 380 nm to 500 nm, can be used in the invention. Suitable photoinitiators are benzoin methyl ether, diethoxyacetophenone, a benzoylphosphine oxide, 1-hydroxycyclohexyl phenyl ketone and Darocur and Irgacur types, preferably Darocur 1173® and Darocur 2959®, Germanium-based Norrish Type I photoinitiators. Examples of benzoylphosphine initiators include phenyl(2,4,6-trimethylbenzoyl)phosphinic acid and its salts, bis(2,4,6-trimethylbenzoyl)phosphinic acid and its salts, 2,4,6-trimethylbenzoyldiphenylophosphine oxide; bis-(2,6-dichlorobenzoyl)-4-N-propylphenylphosphine oxide; and bis-(2,6-dichlorobenzoyl)-4-N-butylphenylphosphine oxide. Reactive photoinitiators which can be incorporated, for example, into a macromer or can be used as a special monomer are also suitable. Examples of reactive photoinitiators are those disclosed in EP 632 329, herein incorporated by reference in its entirety. Most preferably, water-soluble Germanium-based Norrish Type I photoinitiators, which are disclosed in copending U.S. patent application No. 62/169,722 filed Jun. 2, 2015 (herein incorporated by reference in its entirety), are used in the invention. The polymerization can then be triggered off by actinic radiation, for example, UV and/or visible light of a suitable wavelength. The spectral requirements can be controlled accordingly, if appropriate, by addition of suitable photosensitizers.

Nearly any hydrophilic vinylic monomer can be used in the invention. Suitable hydrophilic vinylic monomers are, without this being an exhaustive list, N,N-dimethylacrylamide (DMA), N,N-dimethylmethacrylamide (DMMA), 2-acrylamidoglycolic acid, N-hydroxypropylacrylamide, N-hydroxyethyl acrylamide, N-[tris(hydroxymethyl) methyl]-acrylamide, N-vinylpyrrolidone (NVP), N-vinyl formamide, N-vinyl acetamide, N-vinyl isopropylamide, N-vinyl-N-methyl acetamide (VMA), N-methyl-3-methylene-2-pyrrolidone, 1-methyl-5-methylene-2-pyrrolidone, 5-methyl-3-methylene-2-pyrrolidone, 2-hydroxyethylmethacrylate (HEMA), 2-hydroxyethyl acrylate (HEA), hydroxypropyl acrylate, hydroxypropyl methacrylate, methoxyethylmethacrylate (i.e., ethylene glycol methyl ether methacrylate, EGMA), trimethylammonium 2-hydroxy propylmethacrylate hydrochloride, aminopropyl methacrylate hydrochloride, dimethylaminoethyl methacrylate (DMAEMA), glycerol methacrylate (GMA), a $C_1$-$C_4$-alkoxy polyethylene glycol (meth)acrylate having a weight average molecular weight of up to 1500, polyethylene glycol (meth)acrylate having a weight average molecular weight of up to 1500, methacrylic acid, acrylic acid, and mixtures thereof.

Examples of water-soluble prepolymers free of silicone include without limitation: a water-soluble crosslinkable poly(vinyl alcohol) prepolymer described in U.S. Pat. Nos. 5,583,163 and 6,303,687; a water-soluble vinyl group-terminated polyurethane prepolymer described in U.S. Pat. No. 6,995,192; derivatives of a polyvinyl alcohol, polyethyleneimine or polyvinylamine, which are disclosed in U.S. Pat. No. 5,849,841; a water-soluble crosslinkable polyurea prepolymer described in U.S. Pat. Nos. 6,479,587 and 7,977,430; crosslinkable polyacrylamide; crosslinkable statistical copolymers of vinyl lactam, MMA and a comonomer, which are disclosed in U.S. Pat. No. 5,712,356; crosslinkable copolymers of vinyl lactam, vinyl acetate and vinyl alcohol, which are disclosed in U.S. Pat. No. 5,665,840; polyether-polyester copolymers with crosslinkable side chains which are disclosed in U.S. Pat. No. 6,492,478; branched polyalkylene glycol-urethane prepolymers disclosed in U.S. Pat. No. 6,165,408; polyalkylene glycol-tetra (meth)acrylate prepolymers disclosed in U.S. Pat. No. 6,221,303; crosslinkable polyallylamine gluconolactone prepolymers disclosed in U.S. Pat. No. 6,472,489; all of which are incorporated herein by references in their entireties.

Any suitable of silicone-containing prepolymers with hydrophilic segments and hydrophobic segments can be used in the invention. Examples of such silicone-containing prepolymers include those described in commonly-owned U.S. Pat. Nos. 6,039,913, 7,091,283, 7,268,189 and 7,238,750, 7,521,519; commonly-owned US patent application publication Nos. US 2008-0015315 A1, US 2008-0143958 A1, US 2008-0143003 A1, US 2008-0234457 A1, US 2008-0231798 A1, US 2010-0296049 A1, and US 2010-0298446 A1; all of which are incorporated herein by references in their entireties.

A lens formulation of the invention can also comprise a non-silicone hydrophobic monomer (i.e., free of silicone). By incorporating a certain amount of non-silicone hydrophobic vinylic monomer in a lens formulation, the mechanical properties (e.g., modulus of elasticity) of the resultant polymer may be improved. Nearly any non-silicone hydrophobic vinylic monomer can be used in the actinically polymerizable composition for preparing the intermediary copolymer with pendant or terminal functional groups. Examples of preferred non-silicone hydrophobic vinylic monomers include methylacrylate, ethyl-acrylate, propylacrylate, isopropylacrylate, cyclohexylacrylate, 2-ethylhexylacrylate, methylmethacrylate, ethylmethacrylate, propylmethacrylate, vinyl acetate, vinyl propionate, vinyl butyrate, vinyl valerate, styrene, chloroprene, vinyl chloride, vinylidene chloride, acrylonitrile, 1-butene, butadiene, methacrylonitrile, vinyl toluene, vinyl ethyl ether, perfluorohexylethyl-thio-carbonyl-aminoethyl-methacrylate, isobornyl methacrylate, trifluoroethyl methacrylate, hexafluoro-isopropyl methacrylate, hexafluorobutyl methacrylate.

Any suitable siloxane-containing vinylic monomers can be used in the invention. Examples of preferred siloxane-containing vinylic monomers include without limitation N-[tris(trimethylsiloxy)silylpropyl]-(meth)acrylamide, N-[tris(dimethylpropylsiloxy)-silylpropyl]-(meth)acrylamide, N-[tris(dimethylphenylsiloxy)silylpropyl] (meth)acrylamide, N-[tris(dimethylethylsiloxy)silylpropyl] (meth)acrylamide, N-(2-hydroxy-3-(3-(bis(trimethylsilyloxy)-methylsilyl)propyloxy)propyl)-2-methyl acrylamide; N-(2-hydroxy-3-(3-(bis(trimethylsilyloxy)-methylsilyl)propyloxy)propyl) acrylamide; N,N-bis[2-hydroxy-3-(3-(bis(trimethylsilyloxy)-methylsilyl)propyloxy)propyl]-2-methyl acrylamide; N,N-bis[2-hydroxy-3-(3-(bis (trimethylsilyloxy)-methylsilyl)propyloxy)propyl] acrylamide; N-(2-hydroxy-3-(3-(tris(trimethylsilyloxy)silyl)-propyloxy)propyl)-2-methyl acrylamide; N-(2-hydroxy-3-(3-(tris(trimethylsilyloxy)silyl)propyloxy)-propyl) acrylamide; N,N-bis[2-hydroxy-3-(3-(tris (trimethylsilyloxy)silyl)propyloxy)propyl]-2-methyl acrylamide; N,N-bis[2-hydroxy-3-(3-(tris(trimethylsilyloxy)silyl)propyloxy)propyl]acrylamide; N-[2-hydroxy-3-(3-(t-butyldimethylsilyl)propyloxy)propyl]-2-methyl acrylamide; N-[2-hydroxy-3-(3-(t-butyldimethylsilyl)propyloxy) propyl]acrylamide; N,N-bis[2-hydroxy-3-(3-(t-butyldimethylsilyl)-propyloxy)propyl]-2-methyl acrylamide; N,N-bis[2-hydroxy-3-(3-(t-butyldimethylsilyl) propyloxy)-propyl]acrylamide; 3-methacryloxy propylpentamethyldisiloxane, tris(trimethylsilyloxy)silylpropyl methacrylate (TRIS), (3-methacryloxy-2-hydroxypropyloxy) propylbis(trimethylsiloxy)-methylsilane), (3-methacryloxy-2-hydroxypropyloxy)propyltris(trimethylsiloxy)silane, 3-methacryloxy-2-(2-hydroxyethoxy)-propyloxy)propylbis (trimethylsiloxy)methylsilane, N-2-methacryloxyethyl-O-(methyl-bis-trimethylsiloxy-3-propyl)silylcarbamate, 3-(trimethylsilyl)-propylvinyl carbonate, 3-(vinyloxycarbonylthio)propyl-tris(trimethyl-siloxy)silane, 3-[tris(trimethyl-siloxy)silyl]propylvinyl carbamate, 3-[tris(trimethylsiloxy)silyl] propyl allyl carbamate, 3-[tris(trimethylsiloxy) silyl]propyl vinyl carbonate, t-butyldimethyl-siloxyethyl vinyl carbonate; trimethylsilylethyl vinyl carbonate, and trimethylsilylmethyl vinyl carbonate); monomethacrylated or monoacrylated polydimethylsiloxanes of various molecular weight (e.g., mono-3-methacryloxypropyl terminated, mono-butyl terminated polydimethylsiloxane or mono-(3-methacryloxy-2-hydroxypropyloxy) propyl terminated, mono-butyl terminated polydimethylsiloxane); mono-vinyl carbonate-terminated polydimethylsiloxanes; mono-vinyl carbamate-terminated polydimethylsiloxane; mono-methacrylamide-terminated polydimethylsiloxanes; mono-acrylamide-terminated polydimethylsiloxanes; carbosiloxane vinylic monomers disclosed in U.S. Pat. Nos. 7,915,323 and 8,420,711, in US Patent Application Publication Nos. 2012/244088 and 2012/245249 (herein incorporated by references in their entireties); combinations thereof.

Any suitable siloxane-containing vinylic macromers (i.e., crosslinkers) can be used in the invention. Examples of preferred siloxane-containing vinylic macromers (crosslinkers) are dimethacrylated or diacrylated polydimethylsiloxanes of various molecular weight; di-vinyl carbonate-terminated polydimethylsiloxanes; di-vinyl carbamate-terminated polydimethylsiloxane; di-methacrylamide-terminated polydimethylsiloxanes; di-acrylamide-terminated polydimethylsiloxanes; bis-3-methacryloxy-2-hydroxypropyloxypropyl polydimethylsiloxane; N,N,N',N'-tetrakis(3-methacryloxy-2-hydroxypropyl)-alpha,omega-bis-3-aminopropyl-polydimethylsiloxane; polysiloxanylalkyl (meth)acrylic monomers; siloxane-containing macromer selected from the group consisting of Macromer A, Macromer B, Macromer C, and Macromer D described in U.S. Pat. No. 5,760,100 (herein incorporated by reference in its entirety); chain-extended polysiloxabe vinylic crosslinkers disclosed in US201008843A1 and US20120088844A1 (herein incorporated by references in their entireties); the reaction products of glycidyl methacrylate with amino-functional polydimethylsiloxanes; hydroxyl-functionalized siloxane-containing vinylic monomers or macromers; polysiloxane-containing macromers disclosed in U.S. Pat. Nos. 4,136,250, 4,153,641, 4,182,822, 4,189,546, 4,343,927, 4,254,248, 4,355,147, 4,276,402, 4,327,203, 4,341,889, 4,486,577, 4,543,398, 4,605,712, 4,661,575, 4,684,538, 4,703,097, 4,833,218, 4,837,289, 4,954,586, 4,954,587, 5,010,141, 5,034,461, 5,070,170, 5,079,319, 5,039,761, 5,346,946, 5,358,995, 5,387,632, 5,416,132, 5,451,617, 5,486,579, 5,962,548, 5,981,675, 6,039,913, and 6,762,264 (here incorporated by reference in their entireties); polysiloxane-containing macromers disclosed in U.S. Pat. Nos. 4,259,467, 4,260,725, and 4,261,875 (herein incorporated by reference in their entireties).

Examples of preferred vinylic cross-linking agents include without limitation tetraethyleneglycol diacrylate, triethyleneglycol diacrylate, diethyleneglycol diacrylate, ethyleneglycol diacrylate, tetraethyleneglycol dimethacrylate, triethyleneglycol dimethacrylate, diethyleneglycol dimethacrylate, ethyleneglycol dimethacrylate, tetraethyleneglycol divinyl ether, triethyleneglycol divinyl ether, diethyleneglycol divinyl ether, ethyleneglycol divinyl ether, trimethylopropane trimethacrylate, pentaerythritol tetramethacrylate, bisphenol A dimethacrylate, vinyl methacrylate, ethylenediamine dimethyacrylamide, ethylenediamine diacrylamide, glycerol dimethacrylate, triallyl isocyanurate, triallyl cyanurate, allylmethacrylate, allylacrylate, N-allylmethacrylamide, N-allyl-acrylamide, 1,3-bis(methacrylamidopropyl)-1,1,3,3-tetrakis(trimethyl-siloxy)disiloxane, N,N'-methylenebisacrylamide, N,N'-methylenebismethacrylamide, N,N'-ethylenebisacrylamide, N,N'-ethylenebismethacrylamide, 1,3-bis(N-methacrylamidopropyl)-1,1,3,3-tetrakis-(trimethylsiloxy)disiloxane, 1,3-bis(methacrylamidobutyl)-1,1,3,3-tetrakis(trimethylsiloxy) disiloxane, 1,3-bis(acrylamidopropyl)-1,1,3,3-tetrakis (trimethylsiloxy)-disiloxane, 1,3-bis (methacryloxyethylureidopropyl)-1,1,3,3-tetrakis (trimethylsiloxy)disiloxane, and combinations thereof. A preferred cross-linking agent is tetra(ethyleneglycol) diacrylate, tri(ethyleneglycol) diacrylate, ethyleneglycol diacrylate, di(ethyleneglycol) diacrylate, methylenebisacrylamide, triallyl isocyanurate, or triallyl cyanurate. The amount of a cross-linking agent used is expressed in the weight content with respect to the total polymer and is preferably in the range from about 0.05% to about 3% (more preferably from about 0.1% to about 2%).

A lens formulation of the invention can further comprise visibility tinting agents (e.g., D&C Blue No. 6, D&C Green No. 6, D&C Violet No. 2, carbazole violet, certain copper complexes, certain chromium oxides, various iron oxides, phthalocyanine green, phthalocyanine blue, titanium dioxides, or mixtures thereof), antimicrobial agents (e.g., silver nanoparticles), a bioactive agent (e.g., a drug, an amino acid, a polypeptide, a protein, a nucleic acid, 2-pyrrolidone-5-carboxylic acid (PCA), an alpha hydroxyl acid, linoleic and gamma linoleic acids, vitamins, or any combination thereof), leachable lubricants (e.g., a non-crosslinkable hydrophilic polymer having an average molecular weight from 5,000 to 500,000, preferably from 10,000 to 300,000, more preferably from 20,000 to 100,000 Daltons), leachable tear-stabilizing agents (e.g., a phospholipid, a monoglyceride, a diglyceride, a triglyceride, a glycolipid, a glyceroglycolipid, a sphingolipid, a sphingo-glycolipid, a fatty acid having 8 to 36 carbon atoms, a fatty alcohol having 8 to 36 carbon atoms, or a mixture thereof), and the like, as known to a person skilled in the art.

In a preferred embodiment, the lens formulation is a water-based lens formulation which comprises one or more water-soluble actinically-crosslinkable poly(vinyl alcohol) prepolymer. Preferably, a water-soluble, actinically-crosslinkable polyvinyl alcohol prepolymer comprises repeating units of vinyl alcohol

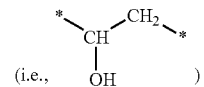

(i.e., )

and repeating units of formula (VIII)

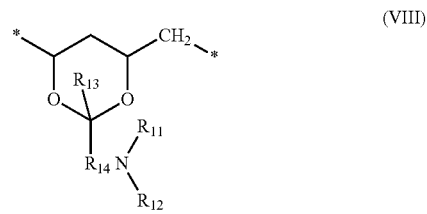

in which:
$R_{11}$ is hydrogen or $C_1$-$C_6$ alkyl (preferably hydrogen or $C_1$-$C_4$ alkyl, more preferably hydrogen or methyl or ethyl, even more preferably hydrogen or methyl);
$R_{12}$ is an ethylenically unsaturated group of

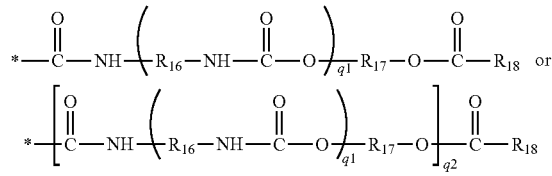

in which q1 and q2 independently of each another are zero or one, and $R_{16}$ and $R_{17}$ independently of each another are a $C_2$-$C_8$ alkylene divalent radical, $R_{18}$ is $C_2$-$C_8$ alkenyl;
$R_{13}$ can be hydrogen or a $C_1$-$C_6$ alkyl group (preferably hydrogen); and
$R_{14}$ is a $C_1$-$C_6$ alkylene divalent radical (preferably a $C_1$-$C_4$ alkylene divalent radical, more preferably methylene or butylene divalent radical, even more preferably methylene divalent radical).

In another preferred embodiment, a lens formulation comprises a water-soluble silicone-containing prepolymer. Examples of water-soluble silicone-containing prepolymers include without limitation those disclosed in U.S. Pat. No. 9,187,601 (herein incorporated by reference in its entirety).

A "water-based lens formulation" refers to a polymerizable composition which comprises water as solvent or a solvent mixture comprising at least about 60% (preferably at least about 80%, more preferably at least about 90%, even more preferably at least about 95%, most preferably at least about 98%) by weight of water relative to the total amount of the solvent mixture and polymerizable/crosslinkable components, and which can be cured (i.e., polymerized and/or crosslinked) thermally or actinically to obtain a crosslinked/polymerized polymeric material.

It is understood that the amount of the UV-absorbing vinylic monomer present in the lens formulation is sufficient to render a resultant contact lens, which is obtained from the curing of the lens formulation, ability of blocking or absorbing (i.e., the inverse of transmittance) at least 90% (preferably at least about 95%, more preferably at least about 97.5%, even more preferably at least about 99%) of UVB (between 280 and 315 nanometers), at least 70% (preferably at least about 80%, more preferably at least about 90%, even more preferably at least about 95%) of UVA transmittance (between 315 and 380 nanometers), and optionally (but preferably) at least 30% (preferably at least about 40%, more preferably at least about 50%, even more preferably at least about 60%) of violet light between 380 nm and 440 nm, which impinge on the lens.

In accordance with the invention, a lens formulation can be a water-based lens formulation, an organic solvent-based lens formulation, or a solventless formulation.

A lens formulation can be prepared by dissolving all of the desirable components in water, a mixture of water and an organic solvent, an organic solvent, or a mixture of two or more organic solvent, or by blending all polymerizable components without any solvent, as known to a person skilled in the art.

In another preferred embodiment, the lens formulation comprises an UV-absorbing vinylic monomer of any one of formula (I) to (VII) in which Q1, Q2, and Q3 are a (meth)acryloylamido group (preferably an acryloylamido group). By having a (meth)acryloylamido group (preferably an acryloylamido group), a relatively-short curing time (e.g., less than 100 seconds, preferably less than 75 seconds, more preferably less than 50 second, even more preferably about 30 seconds or less) can be achieved.

Lens molds for making contact lenses are well known to a person skilled in the art. Methods of manufacturing mold sections for cast-molding a contact lens are generally well known to those of ordinary skill in the art. The process of the present invention is not limited to any particular method of forming a mold. In fact, any method of forming a mold can be used in the present invention. The first and second mold halves can be formed through various techniques, such as injection molding or lathing. Examples of suitable processes for forming the mold halves are disclosed in U.S. Pat. No. 4,444,711 to Schad; U.S. Pat. No. 4,460,534 to Boehm et al.; U.S. Pat. No. 5,843,346 to Morrill; and U.S. Pat. No. 5,894,002 to Boneberger et al., which are also incorporated herein by reference. Virtually all materials known in the art for making molds can be used to make molds for making contact lenses. For example, polymeric materials, such as polyethylene, polypropylene, polystyrene, PMMA, Topas® COC grade 8007-S10 (clear amorphous copolymer of ethylene and norbornene, from Ticona GmbH of Frankfurt, Germany and Summit, N.J.), or the like can be used. Other materials that allow UV light transmission could be used, such as quartz glass and sapphire.

Preferably, a reusable mold suitable for spatial limitation of radiation is used in the invention, the projected beam of radiation (e.g., radiation from the light source including the light in the region of 360 nm to 550 nm) limits radiation (e.g., UV radiation) impinging on the mixture of the lens-forming materials located in the path of the projected beam from the first molding surface to the second molding surface of the reusable mold. The resultant contact lens comprises an anterior surface defined by the first molding surface, an opposite posterior surface defined by the second molding surface, and a lens edge (with sharp edge and high quality) defined by the sectional profile of the projected radiation beam (i.e., a spatial limitation of radiation). Examples of reusable molds suitable for spatial limitation of radiation include without limitation those disclosed in U.S. Pat. Nos. 6,627,124, 6,800,225, 7,384,590, and 7,387,759, which are incorporated by reference in their entireties.

For example, a preferred reusable mold comprises a first mold half having a first molding surface and a second mold half having a second molding surface. The two mold halves of the preferred reusable mold are not touching each other, but there is a thin gap of annular design arranged between the two mold halves. The gap is connected to the mold cavity formed between the first and second molding surfaces, so that excess mixture can flow into the gap. It is understood that gaps with any design can be used in the invention.

In a preferred embodiment, at least one of the first and second molding surfaces is permeable to a crosslinking radiation. More preferably, one of the first and second molding surfaces is permeable to a crosslinking radiation while the other molding surface is poorly permeable to the crosslinking radiation.

The reusable mold preferably comprises a mask which is fixed, constructed or arranged in, at or on the mold half having the radiation-permeable molding surface. The mask is impermeable or at least of poor permeability compared with the permeability of the radiation-permeable molding surface. The mask extends inwardly right up to the mold cavity and surrounds the mold cavity so as to screen all areas behind the mask with the exception of the mold cavity.

The mask may preferably be a thin chromium layer, which can be produced according to processes as known, for example, in photo and UV lithography. Other metals or metal oxides may also be suitable mask materials. The mask can also be coated with a protective layer, for example of silicon dioxide if the material used for the mold or mold half is quartz.

Alternatively, the mask can be a masking collar made of a material comprising a UV/visible light-absorber and substantially blocks curing energy therethrough as described in U.S. Pat. No. 7,387,759 (incorporated by reference in its entirety). In this preferred embodiment, the mold half with the mask comprises a generally circular disc-shaped transmissive portion and a masking collar having an inner diameter adapted to fit in close engagement with the transmissive portion, wherein said transmissive portion is made from an optically clear material and allows passage of curing energy therethrough, and wherein the masking collar is made from a material comprising a light-blocker and substantially blocks passage of curing energy therethrough, wherein the masking collar generally resembles a washer or a doughnut, with a center hole for receiving the transmissive portion, wherein the transmissive portion is pressed into the center opening of the masking collar and the masking collar is mounted within a bushing sleeve.

Reusable molds can be made of quartz, glass, sapphire, $CaF_2$, a cyclic olefin copolymer (such as for example, Topas® COC grade 8007-S10 (clear amorphous copolymer of ethylene and norbornene) from Ticona GmbH of Frankfurt, Germany and Summit, N.J., Zeonex® and Zeonor® from Zeon Chemicals LP, Louisville, Ky.), polymethylmethacrylate (PMMA), polyoxymethylene from DuPont (Delrin), Ultem® (polyetherimide) from G.E. Plastics, PrimoSpire®, etc. Because of the reusability of the mold halves, a relatively high outlay can be expended at the time of their production in order to obtain molds of extremely high precision and reproducibility. Since the mold halves do not touch each other in the region of the lens to be produced, i.e. the cavity or actual molding surfaces, damage as a result of contact is ruled out. This ensures a high service life of the molds, which, in particular, also ensures high reproducibility of the contact lenses to be produced and high fidelity to the lens design.

In accordance with the invention, the lens formulation can be introduced (dispensed) into a cavity formed by a mold according to any known methods.

After the lens formulation is dispensed into the mold, it is polymerized to produce a contact lens. Crosslinking may be initiated thermally or upon exposure to a light source including a light in a region between 380 nm to 500 nm, preferably under a spatial limitation of actinic radiation, to crosslink the polymerizable components in the mixture.

In accordance with the invention, light source can be any ones emitting light in the 380-500 nm range sufficient to activate Germane-based Norrish Type I photoinitiators. Blue-light sources are commercially available and include: the Palatray CU blue-light unit (available from Heraeus Kulzer, Inc., Irvine, Calif.), the Fusion F450 blue light system (available from TEAMCO, Richardson, Tex.), Dymax Blue Wave 200, LED light sources from Opsytec (385 nm, 395 nm, 405 nm, 435 nm, 445 nm, 460 nm), LED light sources from Hamamatsu (385 nm), and the GE 24" blue fluorescent lamp (available from General Electric Company, U.S.). A preferred blue-light source is the UV LED from Opsytec (those described above).

The intensity of the light source is preferably from about 2 to about 40 mW/cm$^2$, preferably from about 4 to about 20 mW/cm$^2$ in the 400 nm to 550 nm region is more preferred. These intensity values are determined by weighting the lamp output using the photoinitiator master spectrum.

The photocrosslinking according to the invention may be effected in a very short time, e.g. in ≤about 120 seconds, preferably in ≤about 80 seconds, more preferably in ≤50 about seconds, even more preferably in ≤about 30 seconds, and most preferably in 4 to 30 seconds.

Opening of the mold so that the molded lens can be removed from the mold may take place in a manner known per se.

The molded contact lens can be subject to lens extraction to remove unpolymerized vinylic monomers and macromers. The extraction solvent is preferably water or an aqueous solution. After extraction, lenses can be hydrated in water or an aqueous solution of a wetting agent (e.g., a hydrophilic polymer); packaged in lens packages with a packaging solution which can contain about 0.005% to about 5% by weight of a wetting agent (e.g., a hydrophilic polymer), a viscosity-enhancing agent (e.g., methyl cellulose (MC), ethyl cellulose, hydroxymethylcellulose, hydroxyethyl cellulose (HEC), hydroxypropylcellulose (HPC), hydroxypropylmethyl cellulose (HPMC), or a mixture thereof); sterilization such as autoclave at from 118 to 124° C. for at least about 30 minutes; and the like.

In a further aspect, the invention provides a hydrogel contact lens comprising a crosslinked polymeric material which comprises repeating units of an UV-absorbing vinylic monomer of any one of formula (I) to (VII).

A contact lens of the invention preferably is characterized by having an UVB transmittance of about 10% or less (preferably about 5% or less, more preferably about 2.5% or less, even more preferably about 1% or less) between 280 and 315 nanometers and a UVA transmittance of about 30% or less (preferably about 20% or less, more preferably about 10% or less, even more preferably about 5% or less) between 315 and 380 nanometers and optionally (but preferably) a Violet transmittance of about 60% or less, preferably about 50% or less, more preferably about 40% or less, even more preferably about 30% or less) between 380 nm and 440 nm.

A contact lens of the invention further has a water content of preferably from about 15% to about 80%, more preferably from about 30% to about 70% by weight (at room temperature, about 22° C. to 28° C.) when fully hydrated.

Although various embodiments of the invention have been described using specific terms, devices, and methods, such description is for illustrative purposes only. The words used are words of description rather than of limitation. It is to be understood that changes and variations may be made by those skilled in the art without departing from the spirit or scope of the present invention, which is set forth in the following claims. In addition, it should be understood that aspects of the various embodiments may be interchanged either in whole or in part or can be combined in any manner and/or used together, as illustrated below:

1. A UV-absorbing vinylic monomer of any one of formula (I) to (VII)

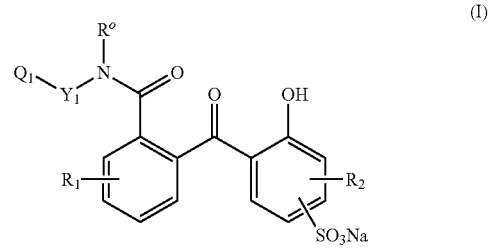

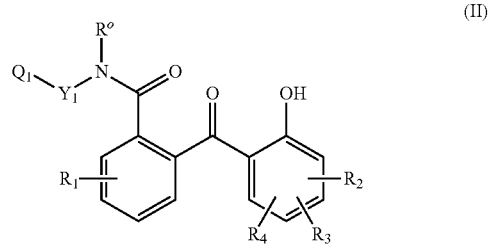

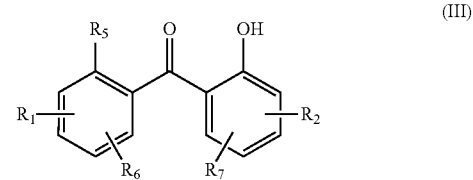

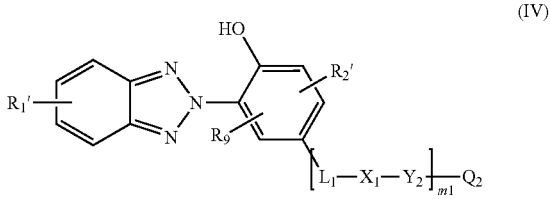

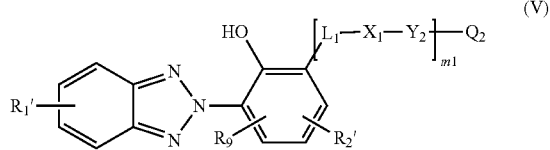

-continued

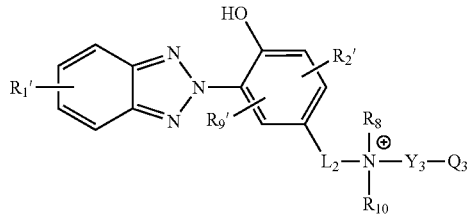
(VI)

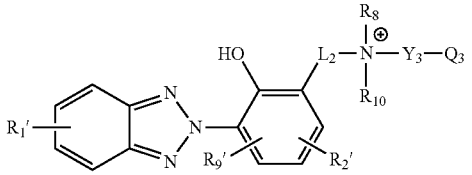
(VII)

in which:

R° is H or CH₃;

R₁, R₂ and R₂' independent of one other are H, CH₃, CCl₃, CF₃, Cl, Br, OH, OCH₃, or NR'R" in which R' and R" independent of each other are H or C₁-C₄ alkyl;

R₁' independent of each other are H, CH₃, CCl₃, CF₃, Cl, Br, OH, OCH₃, SO₃H, SO₃Na, or NR'R" in which R' and R" independent of each other are H or C₁-C₄ alkyl;

R₃ and R₄ independent of each other are H or a first hydrophilic group which is *—CH₂—(OC₂H₄)ₙ₁—OCH₃, *—CH₂—(OC₂H₄)ₙ₁—OH,

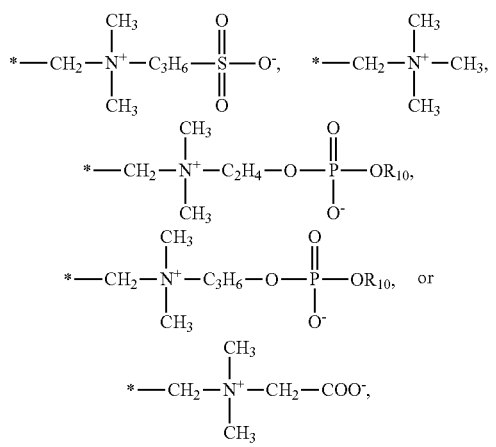

provided that at least one of R₃ and R₄ is the first hydrophilic group;

R₅ is H, *—COOH, *—CONH—C₂H₄—(OC₂H₄)ₙ₁—OCH₃, or *—CONH—C₂H₄—(OC₂H₄)ₙ₁—OH;

one of R₆ and R₇ is H or a second hydrophilic group which is *—CH₂—(OC₂H₄)ₙ₁—OCH₃, *—CH₂—(OC₂Hₙ₁—OH,

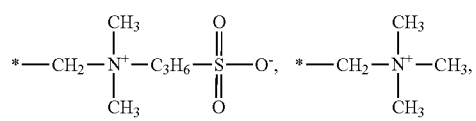

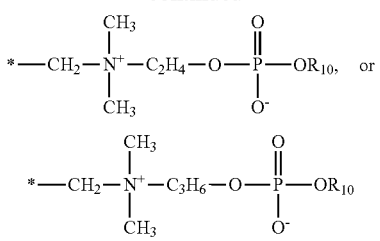

while the other of R₆ and R₇ is

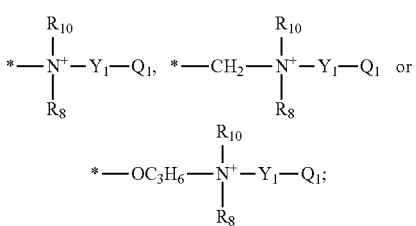

R₈ is CH₃, C₂H₅,

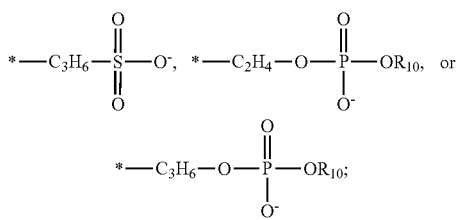

R₉ is SO₃Na,

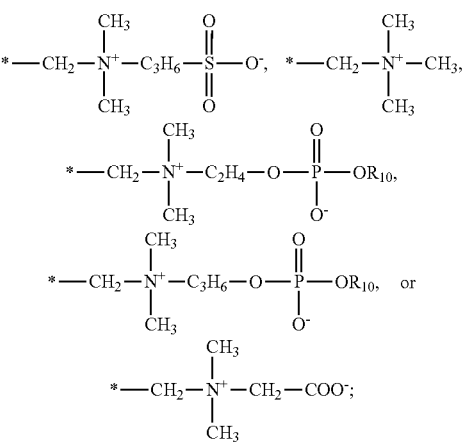

R₉' is H, SO₃Na,

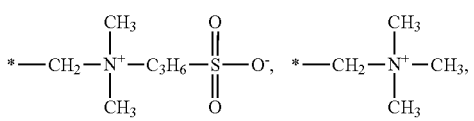

-continued

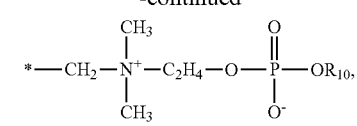

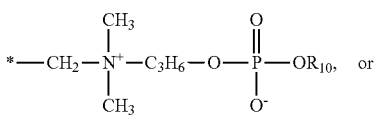

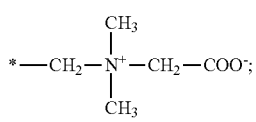

$R_{10}$ is methyl or ethyl;

L1 is a direct bond or a linkage of

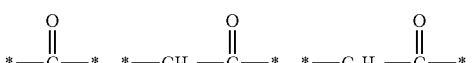

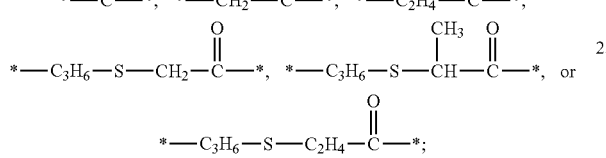

L2 is a linkage of *—$CH_2$—*, *—$C_2H_4$—*, *—$C_3H_6$—*, *—$C_3H_6$—S—$C_2H_4$—*, *—$C_3H_6$—S—$C_3H_6$—*, or

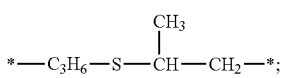

X1 is O or NR°; and $Y_1$, $Y_2$, and $Y_3$ independent of one another are a $C_2$-$C_4$ alkylene divalent radical;

Q1, Q2, and Q3 independent of one another are a (meth)acryloylamido or (meth)acryloyloxy group;

m1 is zero or 1, provided that if m1 is zero, then $Q_2$ is a (meth)acryloylamido group; and n1 is an integer of 2 to 20 (preferably 3 to 15, more preferably 4 to 10).

2. The UV-absorbing vinylic monomer of invention 1, being a vinylic monomer of formula (I).

3. The UV-absorbing vinylic monomer of invention 2, being selected from a vinylic monomer of any one of the following formula:

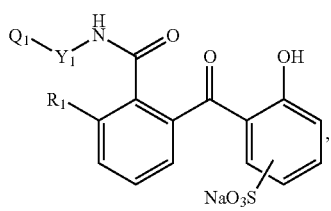

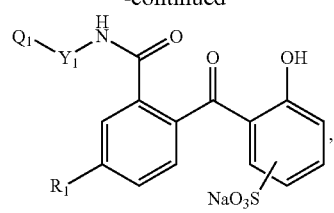

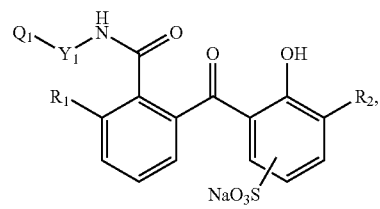

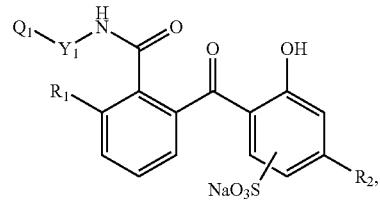

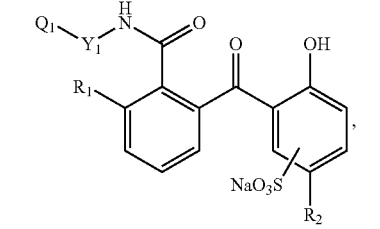

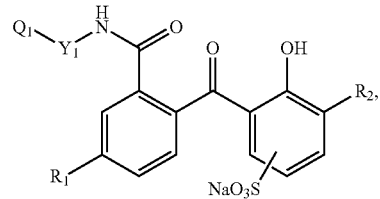

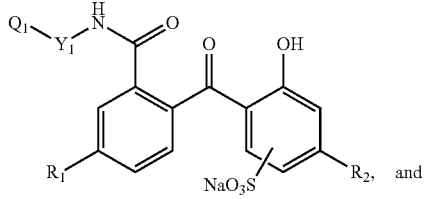
and

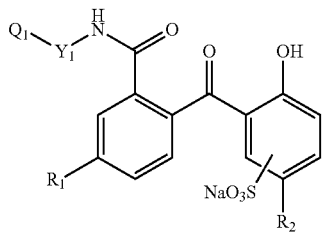

in which: $Q_1$ is (meth)acryloylamido or (meth)acryloyloxy group; $Y_1$ is an ethylene or propylene divalent radical; $R_1$ and $R_2$ independent of each other are H, $CH_3$, $CCl_3$, $CF_3$, Cl, Br, OH, $OCH_3$, or NR'R" in which R' and R" independent of each other are H, methyl or ethyl.

4. The UV-absorbing vinylic monomer of invention 1, being a vinylic monomer of formula (II).
5. The UV-absorbing vinylic monomer of invention 4, being selected from a vinylic monomer of any one of the following formula:
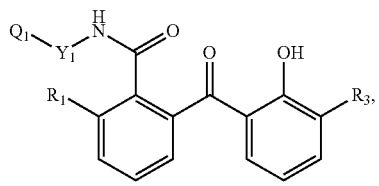
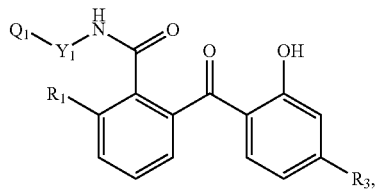
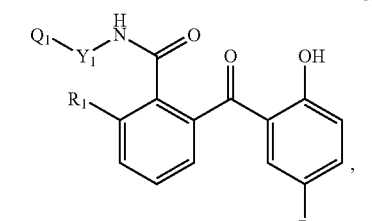
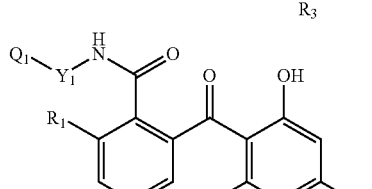
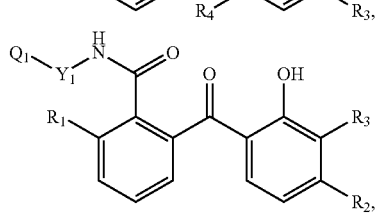
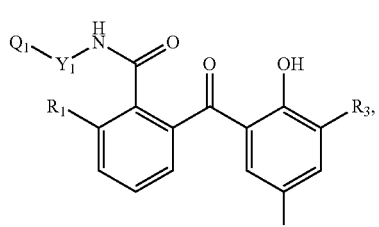
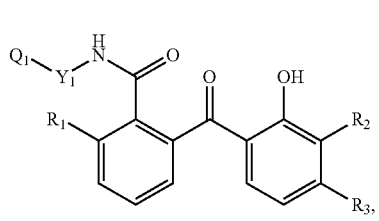
-continued
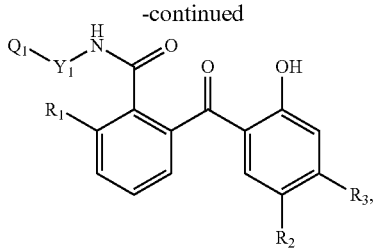
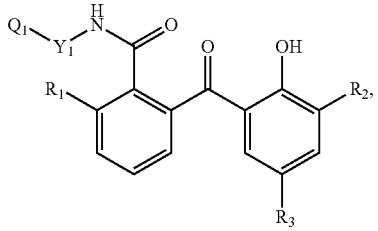
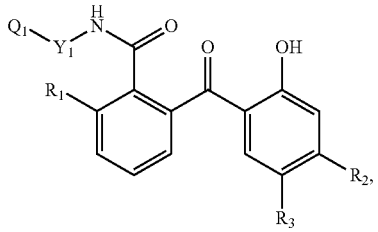
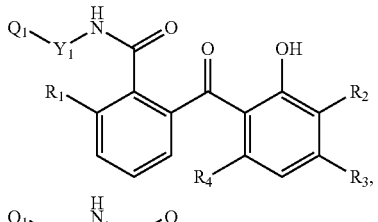
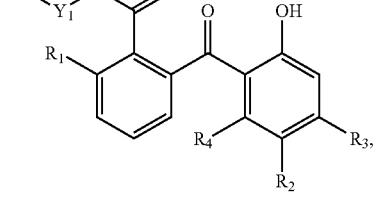
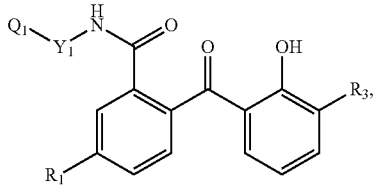
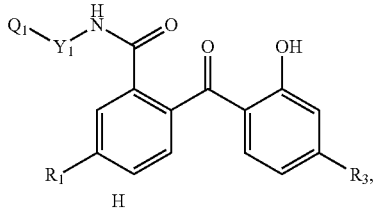
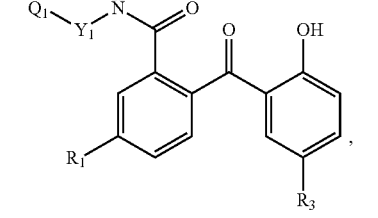

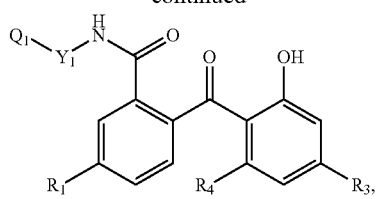
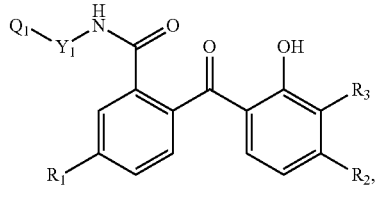
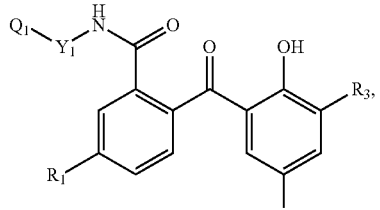
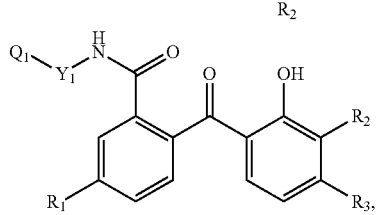
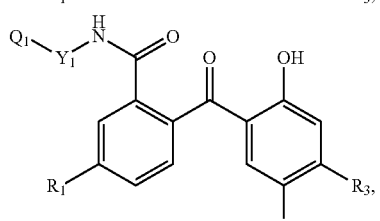
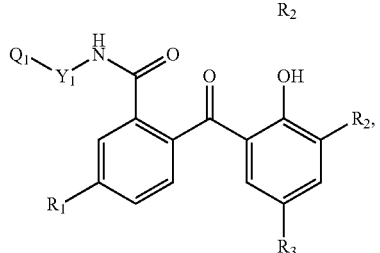
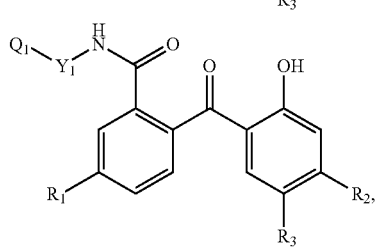
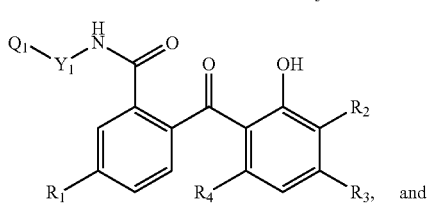 and

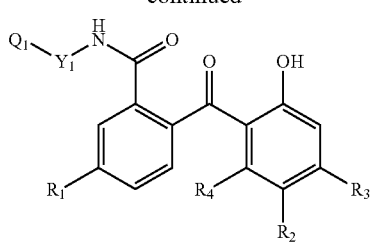

in which: $Q_1$ is (meth)acryloylamido or (meth)acryloyloxy group; $Y_1$ is an ethylene or propylene divalent radical; $R_1$ and $R_2$ independent of each other are $CH_3$, $CCl_3$, $CF_3$, Cl, Br, NR'R", OH, or $OCH_3$; R' and R" independent of each other are H, methyl or ethyl; $R_3$ and $R_4$ independent of each other are *—$CH_2$—$(OC_2H_4)_{n1}$—$OCH_3$, *—$CH_2$—$(OC_2H_4)_{n1}$—OH,

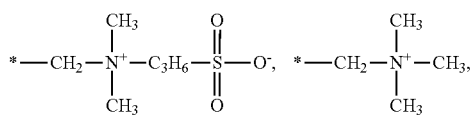
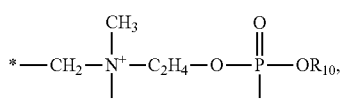
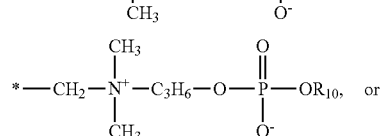 or
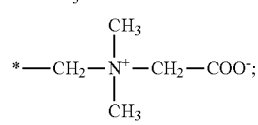

$R_{10}$ is methyl or ethyl.

6. The UV-absorbing vinylic monomer of invention 1, being a vinylic monomer of formula (III).

7. The UV-absorbing vinylic monomer of invention 6, being selected from a vinylic monomer of any one of the following formula:

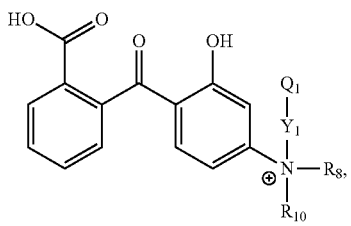
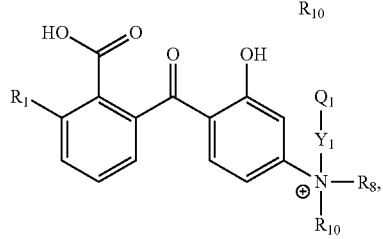

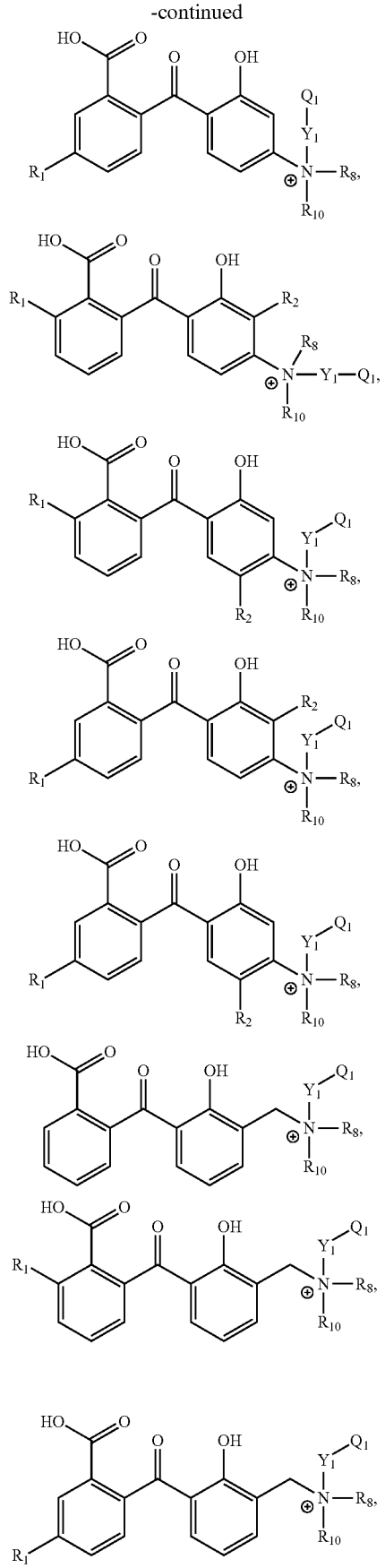
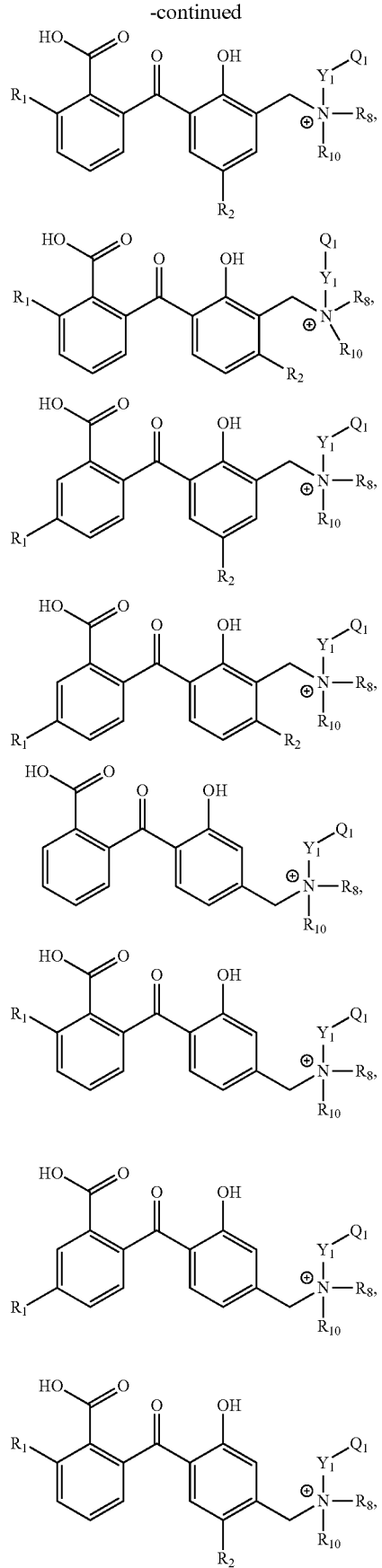

-continued
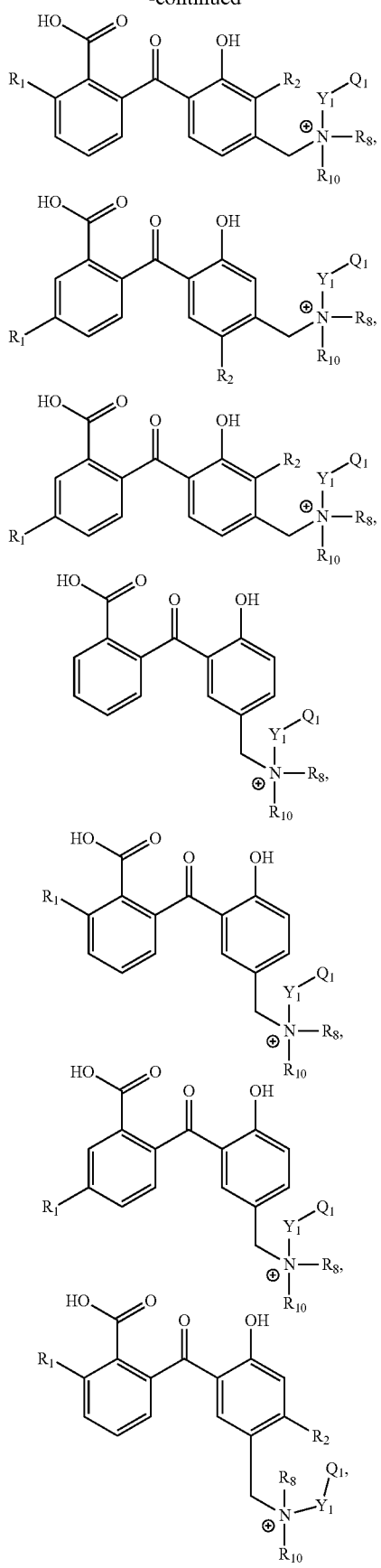
-continued
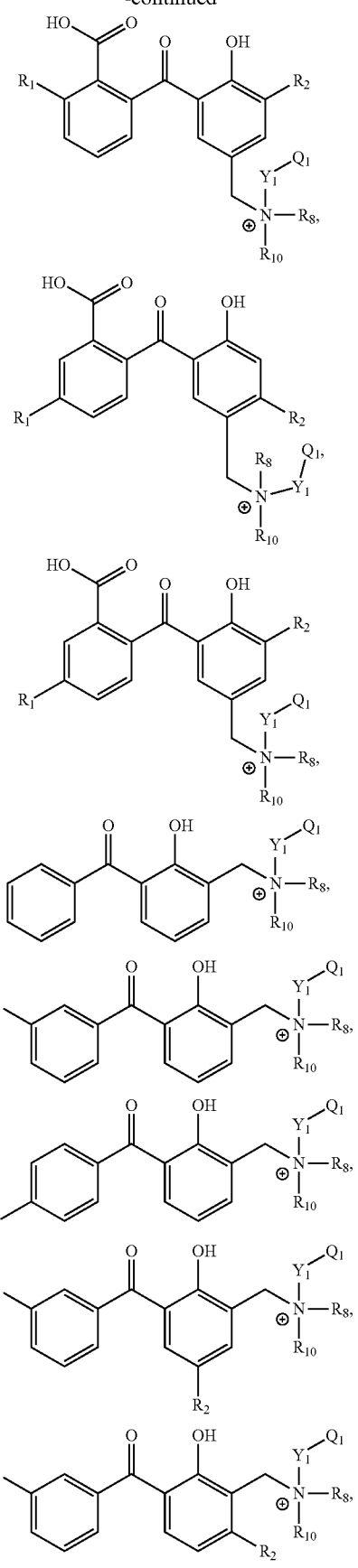

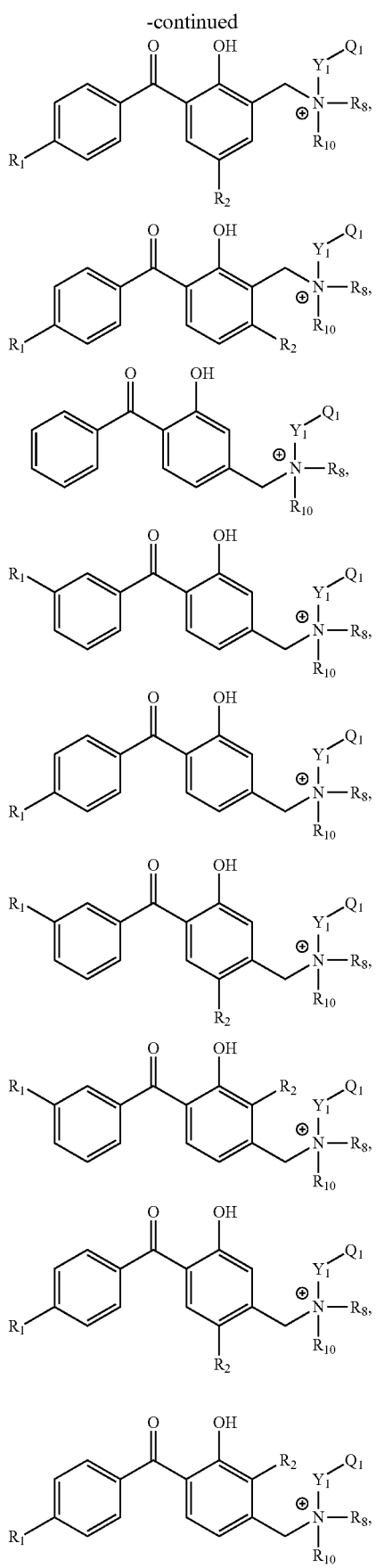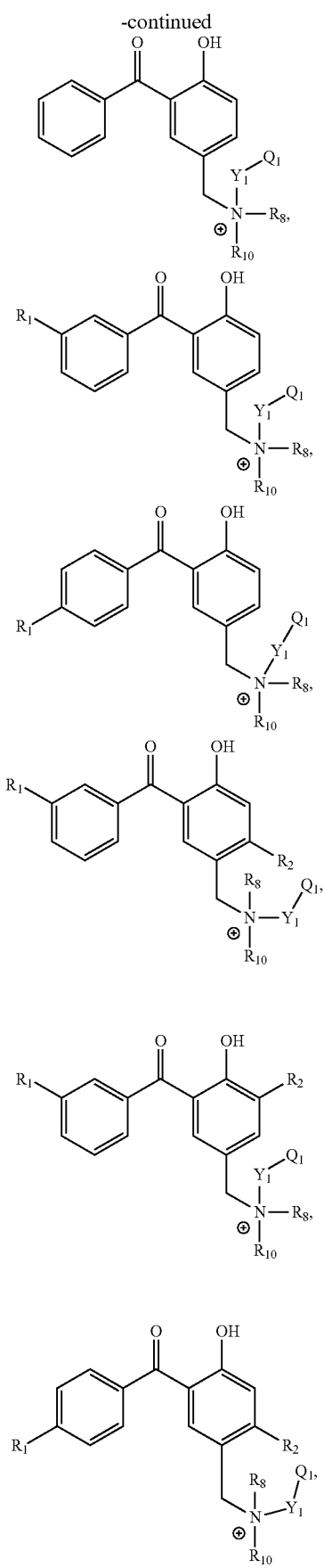

-continued

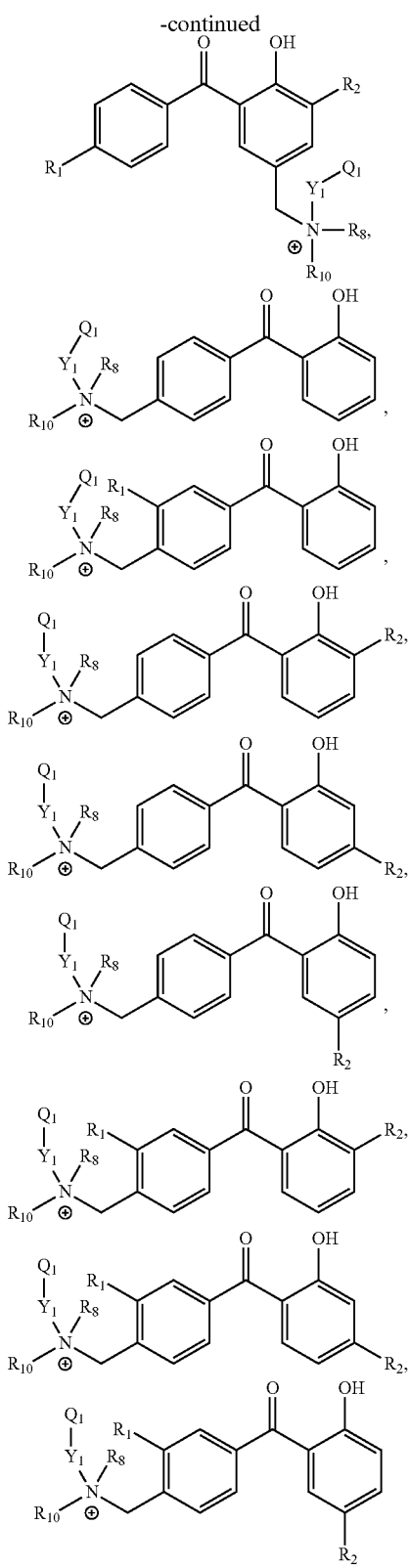

in which: $Q_1$ is (meth)acryloylamido or (meth)acryloyloxy group; $Y_1$ is an ethylene or propylene divalent radical; $R_1$ and $R_2$ independent of each other are $CH_3$, $CCl_3$, $CF_3$, Cl, Br, NR'R'' OH, or $OCH_3$; in which R' and R'' independent of each other are H or $C_1$-$C_4$ alkyl; $R_8$ is $CH_3$, $C_2H_5$,

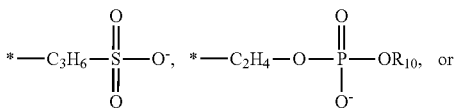

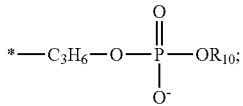

$R_{10}$ is methyl or ethyl.

8. The UV-absorbing vinylic monomer of invention 1, being a vinylic monomer of formula (IV) or (V).

9. The UV-absorbing vinylic monomer of invention 8, being selected from a vinylic monomer of any one of the following formula:

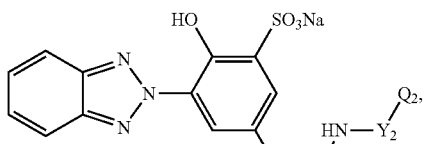

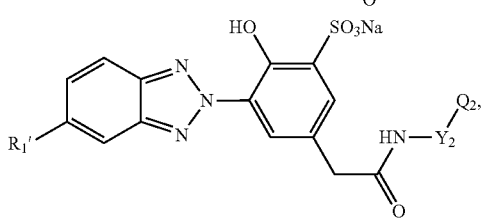

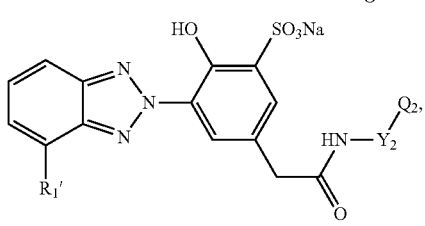

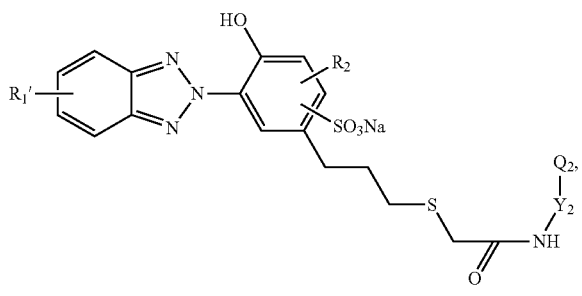

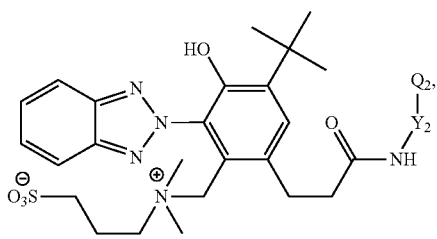

-continued

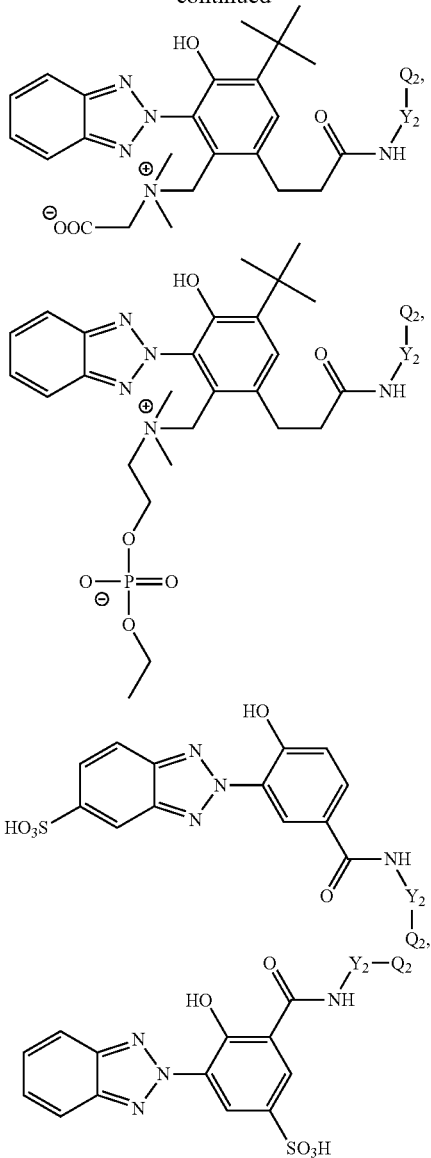

in which $R_1'$ is H, $CH_3$, $CCl_3$, $CF_3$, Cl, Br, NR'R" in which R' and R" independent of each other are H or $C_1$-$C_4$ alkyl, OH, or $OCH_3$; $Q_2$ is (meth)acryloylamido or (meth)acryloyloxy group; $Y_2$ is an ethylene or propylene divalent radical.

10. The UV-absorbing vinylic monomer of invention 1, being a vinylic monomer of formula (VI) or (VII).

11. The UV-absorbing vinylic monomer of invention 10, being selected from a vinylic monomer of any one of the following formula:

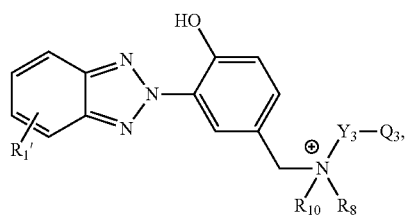

-continued

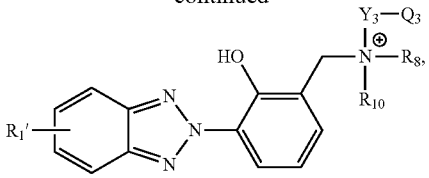

in which $R_1'$ is H, $CH_3$, $CCl_3$, $CF_3$, Cl, Br, OH, or $OCH_3$, NR'R" in which R' and R" independent of each other are H or $C_1$-$C_4$ alkyl, $R_8$ is $CH_3$, $C_2H_5$,

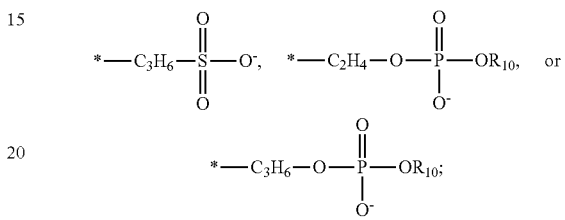

$R_{10}$ is methyl or ethyl; $Q_3$ is (meth)acryloylamido or (meth)acryloyloxy group; $Y_3$ is an ethylene or propylene divalent radical.

12. A hydrogel contact lens, comprising a crosslinked polymeric material which comprises repeating units of a UV-absorbing vinylic monomer of any one of inventions 1 to 11, wherein the hydrogel contact lens has: an UVB transmittance (designated as UVB % T) of about 10% or less between 280 and 315 nanometers; a UVA transmittance (designated as UVA % T) of about 30% or less between 315 and 380 nanometers; and a water content of from about 15% to about 80% by weight (at room temperature, about 22° C. to 28° C.) when being fully hydrated.

13. The hydrogel contact lens of invention 12, wherein the hydrogel contact lens has an UVB % T of about 5% or less (preferably about 2.5% or less, more preferably about 1% or less) between 280 and 315 nanometers.

14. The hydrogel contact lens of invention 12 or 13, wherein the hydrogel contact lens has an UVA % T of about 20% or less (preferably about 10% or less, more preferably about 5% or less) between 315 and 380 nanometers.

15. The hydrogel contact lens of any one of inventions 12 to 14, wherein the hydrogel contact lens further has a Violet transmittance (designated as Violet % T) of about 60% or less (preferably about 50% or less, more preferably about 40% or less, even more preferably about 30% or less) between 380 nm and 440 nm.

16. The hydrogel contact lens of any one of inventions 12 to 15, wherein the hydrogel contact lens has a water content of from about 30% to about 75% by weight (at room temperature, about 22° C. to 28° C.) when being fully hydrated.

17. The hydrogel contact lens of any one of inventions 12 to 16, wherein the hydrogel contact lens is a silicone hydrogel contact lens, wherein the crosslinked polymeric material which comprises repeating units of at least one hydrophilic vinylic monomer and repeating units of at least one siloxane-containing vinylic monomer and/or macromer.

18. The hydrogel contact lens of any one of inventions 12 to 16, wherein the crosslinked polymeric material which comprises repeating units of an actinically-crosslinkable polyvinyl alcohol prepolymer.

19. The hydrogel contact lens of invention 18, wherein the actinically-crosslinkable polyvinyl alcohol prepolymer comprises repeating units of vinyl alcohol

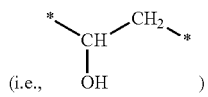

(i.e., OH )

and repeating units of formula (VIII)

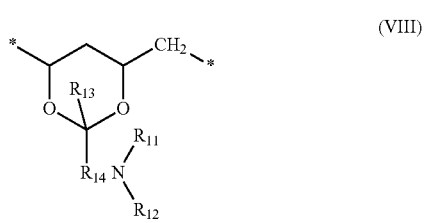

in which:
$R_{11}$ is hydrogen or $C_1$-$C_6$ alkyl;
$R_{12}$ is an ethylenically unsaturated group of

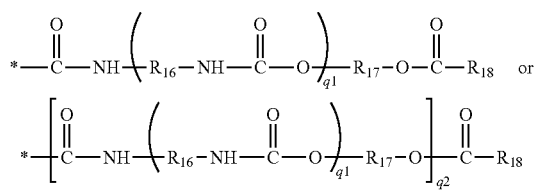

in which q1 and q2 independently of each another are zero or one, and $R_{16}$ and $R_{17}$ independently of each another are a $C_2$-$C_8$ alkylene divalent radical, $R_{18}$ is $C_2$-$C_8$ alkenyl;
$R_{13}$ can be hydrogen or a $C_1$-$C_6$ alkyl group; and
$R_{14}$ is a $C_1$-$C_6$ alkylene divalent radical.

20. The hydrogel contact lens of invention 19, wherein in formula (VIII) $R_{11}$ is hydrogen or $C_1$-$C_4$ alkyl (preferably hydrogen or methyl or ethyl, more preferably hydrogen or methyl).
21. The hydrogel contact lens of invention 19 or 20, wherein in formula (VIII) $R_{13}$ is hydrogen.
22. The hydrogel contact lens of any one of inventions 19 to 21, wherein in formula (VIII) $R_{14}$ is a $C_1$-$C_4$ alkylene divalent radical (preferably methylene or butylene divalent radical, more preferably methylene divalent radical).
23. A method for producing UV-absorbing contact lenses, comprising the steps of:
   (1) obtaining a lens formulation comprising
      (a) a UV-absorbing vinylic monomer of any one of inventions 1 to 11,
      (b) at least one free-radical initiator, and
      (c) at least one polymerizable components selected from the group consisting of a hydrophilic vinylic monomer, a water-soluble silicone-free prepolymer, a silicone-containing prepolymer, a non-silicone hydrophobic vinylic monomer, a siloxane-containing vinylic monomer, a siloxane-containing vinylic macromer, a vinylic crosslinking agent, and combinations thereof;
   (2) introducing the lens formulation into a mold for making a soft contact lens, wherein the mold has a first mold half with a first molding surface defining the anterior surface of a contact lens and a second mold half with a second molding surface defining the posterior surface of the contact lens, wherein said first and second mold halves are configured to receive each other such that a cavity is formed between said first and second molding surfaces; and
   (3) curing thermally or actinically the lens formulation in the mold to form the UV-absorbing contact lens, wherein the formed UV-absorbing contact lens is characterized by having the UVB % T of about 10% or less between 280 and 315 nanometers and a UVA % T of about 30% or less between 315 and 380 nanometers.
24. The method of invention 23, wherein the lens formulation comprises from about 0.1% to about 4% by weight of, preferably from about 0.2% to about 3.0% by weight of, more preferably from about 0.4% to about 2% by weight of, even more preferably from about 0.6% to about 1.5% by weight of a UV-absorbing vinylic monomer of any one of inventions 1 to 11.
25. The method of invention 23 or 24, wherein the lens formulation comprises from about 0.1% to about 2.0% by weight of, preferably from about 0.25% to about 1.75% by weight of, more preferably from about 0.5% to about 1.5% by weight of, even more preferably from about 0.75% to about 1.25% by weight of, at least one free-radical initiator.
26. The method of any one of inventions 23 to 25, wherein the free-radical initiator is a thermal initiator, wherein the step of curing is carried out thermally.
27. The method of any one of inventions 23 to 25, wherein the free-radical initiator is a photoinitiator, wherein the step of curing is carried out by irradiation with a light having a wavelength within the range from 380 nm to 500 nm.
28. The method of invention 27, wherein the photoinitiator is a benzoylphosphine oxide.
29. The method of invention 27, wherein the photoinitiator is a Germanium-based Norrish Type I photoinitiator.
30. The method of any one of inventions 23 to 27, wherein the lens formulation comprises at least one hydrophilic vinylic monomer, at least one siloxane-containing vinylic monomer, at least one siloxane-containing vinylic macromer.
31. The method of any one of inventions 27 to 30, wherein the mold is a reusable mold, wherein the step of curing is carried out by using a spatial limitation of actinic radiation.
32. The method of any one of inventions 27 to 31, wherein the step of curing lasts for a time period of about 120 seconds or less (preferably about 80 seconds or less, more preferably about 50 seconds or less, even more preferably about 30 second or less, most preferably from about 5 to about 30 seconds).
33. The method of any one of inventions 23 to 32, wherein the lens formulation is a water-based lens formulation comprising at least one actinically-crosslinkable polyvinyl alcohol prepolymer, wherein the actinically-crosslinkable polyvinyl alcohol prepolymer comprises repeating units of vinyl alcohol

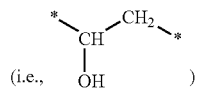

(i.e., OH )

and repeating units of formula (VIII)

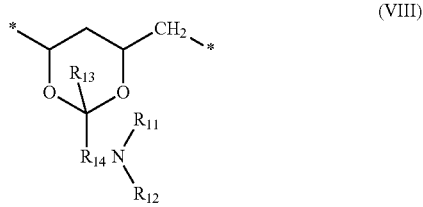

in which:
R$_{11}$ is hydrogen or C$_1$-C$_6$ alkyl;
R$_{12}$ is an ethylenically unsaturated group of

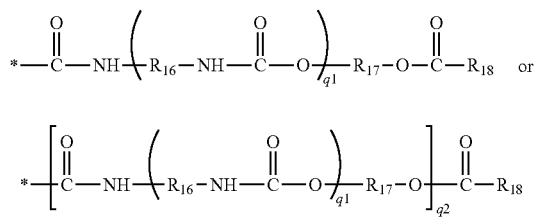

in which q1 and q2 independently of each another are zero or one, and R$_{16}$ and R$_{17}$ independently of each another are a C$_2$-C$_8$ alkylene divalent radical, R$_{18}$ is C$_2$-C$_8$ alkenyl;
R$_{13}$ can be hydrogen or a C$_1$-C$_6$ alkyl group; and
R$_{14}$ is a C$_1$-C$_6$ alkylene divalent radical.

34. The method of invention 33, wherein in formula (VIII) R$_{11}$ is hydrogen or C$_1$-C$_4$ alkyl (preferably hydrogen or methyl or ethyl, more preferably hydrogen or methyl).

35. The method of invention 33 or 34, wherein in formula (VIII) R$_{13}$ is hydrogen.

36. The method of any one of inventions 33 to 35, wherein in formula (VIII) R$_{14}$ is a C$_1$-C$_4$ alkylene divalent radical (preferably methylene or butylene divalent radical, more preferably methylene divalent radical).

37. The method of any one of inventions 33 to 36, wherein in formula (VIII) R$_{11}$ is hydrogen or methyl, R$_{13}$ is hydrogen, and R$_{14}$ is methylene divalent radical.

38. The method of any one of inventions 23 to 37, wherein the formed UV-absorbing contact lens has an UVB % T of about 5% or less (preferably about 2.5% or less, more preferably about 1% or less) between 280 and 315 nanometers.

39. The hydrogel contact lens of any one of inventions 23 to 38, wherein the formed UV-absorbing contact lens has an UVA % T of about 20% or less (preferably about 10% or less, more preferably about 5% or less) between 315 and 380 nanometers.

40. The hydrogel contact lens of any one of inventions 23 to 39, wherein the hydrogel contact lens further has a Violet % T of about 60% or less (preferably about 50% or less, more preferably about 40% or less, even more preferably about 30% or less) between 380 nm and 440 nm.

The previous disclosure will enable one having ordinary skill in the art to practice the invention. Various modifications, variations, and combinations can be made to the various embodiment described herein. In order to better enable the reader to understand specific embodiments and the advantages thereof, reference to the following examples is suggested. It is intended that the specification and examples be considered as exemplary.

Example 1

Transmittance.

Contact lenses are manually placed into a specially fabricated sample holder or the like which can maintain the shape of the lens as it would be when placing onto eye. This holder is then submerged into a 1 cm path-length quartz cell containing phosphate buffered saline (PBS, pH~7.0-7.4) as the reference. A UV/visible spectrophotometer, such as, Varian Cary 3E UV-Visible Spectrophotometer with a LabSphere DRA-CA-302 beam splitter or the like, can be used in this measurement. Percent transmission spectra are collected at a wavelength range of 250-800 nm with % T values collected at 0.5 nm intervals. This data is transposed onto an Excel spreadsheet and used to determine if the lenses conform to Class 1 UV absorbance. Transmittance is calculated using the following equations:

$$UVA \% T = \frac{\text{Average } \% T \text{ between 380-316 nm}}{\text{Luminescence } \% T} \times 100$$

$$UVB \% T = \frac{\text{Average } \% T \text{ between 280-315 nm}}{\text{Luminescence } \% T} \times 100$$

$$\text{Violet } \% T = \frac{\text{Average } \% T \text{ between 440-380 nm}}{\text{Luminescence } \% T} \times 100$$

in which Luminescence % T is the average % transmission between 380 and 780.

Photo-Rheology:

The photo-rheology experiment measures the elastic (G') and viscous modulus (G") as a function of time during curing. The experiment is conducted by using an appropriate light source, optionally cutoff filters to select wavelengths of interest, and a rheometer. The light source is a LED of appropriate wavelength (i.e. 385, 405, 435, 445, or 460 nm), or Mercury bulb in a Hamamatsu light source. The intensity of light source is set by adjusting either the light source output or the shutter opening to get an appropriate intensity measured by a radiometer. The sample is placed between a quartz plate that allows UV light to pass through and the rheometer. The cure time is determined when the elastic modulus (G') reaches a plateau.

Example 2

This example illustrates how to prepare a preferred UV-absorbing vinylic monomer of the invention according to the procedures shown in the following scheme.

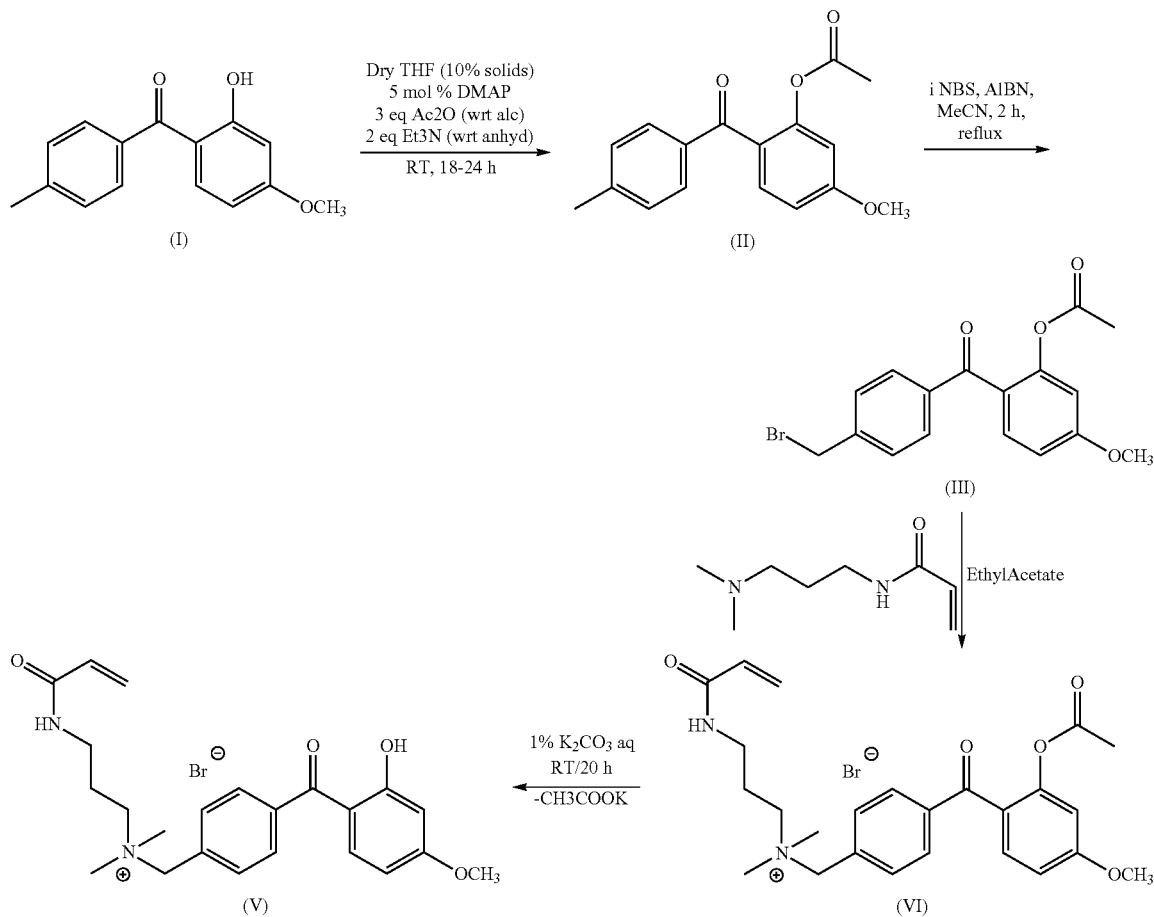

Step 1—Synthesis of 2-acetyloxy-4-methoxy-4'-methyl-benzophenone

In a round bottom (rb) flask fitted with a stir bar and purged with dry nitrogen (dN$_2$) was taken 80 g anhydrous tetrahydrofuran (THF, from Aldrich), 10 g (41.29 mmol/1.0 eq) of 2-hydroxy-4-methoxy-4'-methylbenzophenone (HO-MeO-Me-Bzp) (from Alfa Aesar) (compound I) and 0.25 g of N,N-dimethyamino pyridine (DMAP) (5 mol % with respect to [wrt] to compound I from Alfa Aesar). About 5 mL dry THF was used to rinse the DMAP vial and then this was added to the reaction flask. The mixture was stirred at room temperature (RT) to dissolve over 15 mins. Then, 26 g (6 eq) of triethylamine (TEA, from Aldrich) was added via a syringe. The solution was stirred at RT for 15 minutes. Then, 13.17 g (3.1 eq) Acetic anhydride (Ac2O) was added slowly to the reaction mixture over 5 minutes. 15 mL of anhydrous THF was added to the flask. The reaction solution was stirred under nitrogen (N$_2$) at RT, overnight and then was concentrated under reduced pressure to remove about 80% of the volatiles. THF was added to make a total solution mass having a concentration of about 30 wt % wrt starting benzophenone. The solution was stirred at RT for 5 mins. The product was precipitated by slow addition of a 150 g mixture of 1:1 ice:water (5× by weight [wt] of reaction solution) with stirring. The flask was place in ice water bath and stirred for 3 hours. After 3 hours, the pH of the solution phase was measured as 3.86 (pH meter) and the mixture was filtered through a Whatman#4 (25 μm) filter paper under vacuum of 940 mbar. The precipitate was washed with about 1500 g of ice cold water until the washings were clear colorless and the conductivity of the filtrate was <10 μS/cm and pH neutral. The precipitate was collected and was suspended in 100 mL cold DI Water and swirled for 15 mins. The obtained product was then frozen in IPA-dry ice and then lyophilized. A white powder was obtained that was weighed (Net: 11.45 g; Th Yield: 11.77 g; Yield: 97.36%) and was confirmed by 1H-NMR in THF-d8 to be 2-acetyloxy-4-methoxy-4'-methylbenzophenone (AcO-MeO-Me-Bzp) (compound II).

Step 2—Synthesis of 2-acetyloxy-4-methoxy-4'-bromomethyl-benzophenone

Acetonitrile, N-Bromosuccinimide (NBS) and AIBN were purchased from Sigma Aldrich and acetate protected benzophenone derivative (II) was used as obtained from the previous step. In a 500 mL 3-neck flask fitted with condenser, a N$_2$ purge set up, a thermocouple, an oil-bubbler air trap and a stir bar was added 8.85 g (0.031 mol/1.0 eq) of AcO-MeO-Me-Bzp (II) obtained in Step 1 and was stirred under N$_2$ for 30 mins. The condenser was set to 9° C. and 220 mL of anhydrous acetonitrile was added to the reaction flask. The mixture was stirred at RT. Once the condenser had reached around 9° C., the reaction flask was gently purged with dry N$_2$ for 30 mins and the condenser was set to 4° C. After condenser had reached 4° C. or 30 mins of N$_2$ purge (whichever is later), the reaction mixture was quickly raised to reflux at 400 rpm stirring and with a mildly positive $N_2$ flow. The reaction solution came to reflux at ~80-82° C. Then 6.11 g (1.1 eq.) of N-Bromosuccinimide (NBS) (from Sigma-Aldrich) and 0.52 g (0.1 eq.) of Aza-bis-isobutyronitrile (from Sigma-Aldrich) were weighed out and added to the reaction flask under positive $N_2$ flow. The reaction was continued, at reflux for 2 h with mildly positive nitrogen flow. After two hours the reaction was stopped by being allowed to cool to RT under very mild flow of dry $N_2$. The cooled reaction solution was filtered through a cotton plug. The solution was then concentrated to about 50 wt % under reduced pressure. The product was precipitated form the reaction solution by addition of about 200 g of 1:1 ice-water mixture (about 3× the reaction solution wt.).

The mixture was stirred in an ice bath for 3 hours. After three hours the precipitate was filtered through a Whatman #4 (25 μm) filter paper under 950 mbar pressure. The precipitate was washed 5× with 200 mL cold DI Water, (~5× volume of ice-water used for pptn) until the conductivity of the filtrate was less than 10 uS/cm and neutral pH. The solid sample was mixed with 100 mL cold DI Water and the mixture was then frozen in dry-ice/IPA bath and then lyophilized. A powdery off white solid was obtained (Net: 10.986 g; Th Y: 11.307 g; % Y; 97.17%) and confirmed by NMR to be product III, 2-acetyloxy-4-methoxy-4'-bromomethyl-benzophenone (AcO-MeO—BrCH$_2$-Bzp). The % purity of product III was estimated from NMR to be 85 mol % with about 7% likely to be unreacted starting material and about 8% other unidentified impurities.

Step 3—Synthesis of 2-acetyloxy-4'-methoxy-4'-(acrylamido-N,N-dimethypropylaminomethyl)-benzophenone In a weighed 20 mL amber glass vial with stir bar was taken 1.5 g (0.004 mol/1 eq) of product (III) from Step 2, AcO-MeO—BrCH$_2$-Bzp. To this was added 8 mL ethyl acetate with stirring for 10 mins at room temperature (RT). To the obtained solution was added 1.94 g (0.0123 mol/3. eq) of N,N-dimethylaminopropyl acrylamide (NN-DMAPrAAm) at RT with stirring. A precipitate slowly formed and the reaction was stirred at RT overnight. To the reaction mixture was added 1 mL of hexane and the reaction mixture stirred for an hour at RT. The clear supernatant was discarded. The residue was dissolved in 0.50 mL acetonitrile and stirred for 30 mins to dissolve. The product in the solution was precipitated using excess 1:1 Ethyl acetate: hexane mixture. The process is repeated 4 times. To the solid residue obtained was added 5 mL DI Water and the mixture allowed to dissolve. MEHQ was added to make a concentration of ~150 mg/Kg (ppm) based on estimated final product weight. The residual organics from the cloudy solution were removed under reduced pressure to give a clear solution having neutral pH. The solution was frozen and lyophilized overnight. Net: 1.4829 g; Th.Y: 2.05 g; % Y; 72.19%. The bulk sample was deliquescent and was flushed with dry air and stored in a dessicator in the amber flask. The product IV was obtained and estimated from NMR to have a purity of >90%.

Step 4—Synthesis of 2-hydroxy-4-methoxy-4'-(acrylamido-N,N-dimethypropylaminomethyl)-benzophenone A 5.0 mL solution of acetate protected UV-blocker (IV) in DI Water at 1000 mg/L was prepared. This solution was diluted to 20 mg/L with pH7 buffer (12.5 mM phosphate in DI Water:n-propanol). The UV-Vis spectrum of this solution was collected (FIG. 1, Curve 1).

Solid Potassium Carbonate ($K_2CO_3$) was added to the 1000 mg/L solution to have a $K_2CO_3$ concentration of 1 w/v %. The solution was mixed to dissolve the $K_2CO_3$ and the solution was allowed to stand overnight at RT to obtain the desired product (UV-absorbing vinylic monomer, i.e., compound V in the scheme). The resultant solution was diluted to have a concentration of 20 mg/L for the UV-absorbing vinylic monomer with pH7 buffer (12.5 mM phosphate in DI Water:n-propanol). The UV-Vis spectrum of this solution of the UV-absorbing vinylic monomer was collected and is shown in FIG. 1 (curve 2).

Example 3

The UV-absorbing vinylic monomer prepared in Example 2 was directly added to an aqueous lens formulation, which is described in Example 8-8d of WO2002071106 (herein incorporated by reference in its entirety), at a concentration of 0, 0.7 and 1.5 wt % and each having 1.0 wt % Lithium salt of 2,4,6-trimethylbenzoyl-diphenylphosphine oxide (Li-TPO) (from TCI-America,

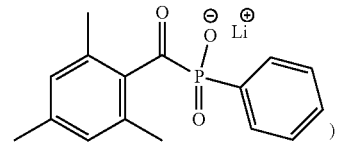 [SMILES: Cc1cc(C)c(C(=O)P(=O)([O-])c2ccccc2)c(C)c1 ; [Li+]]

as the photoinitiator. Those three formulations are determined by photo rheology studies (405 nm LED source at 30 mW/cm$^2$) to have a curing time of about 21 seconds, about 23 seconds, or about 21 seconds respectively.

Lenses were fabricated from those aqueous formulations according to an automated lens manufacturing process described in Example 8 of WO2002071106 except that a lens formulation in a mold is irradiated with 405 nm LED at an intensity of 30 mW/cm$^2$ for about 25 seconds. The resultant lenses were packaged in blister packages containing Saline 61, sealed and autoclaved at 121° C. for 45 mins. The % T (percentage transmittance) of the autoclaved lenses was determined. Where the concentration of the UV-absorbing vinylic monomer is 0 (i.e., control lenses), the control lenses have a % T-UVA~96.30% and a % T-UVB~84.61%. Where the concentration of the UV-absorbing vinylic monomer is 0.70% by weight, the resultant lenses have a % T-UVA~23.6% and a % T-UVB~3.79%. Where the concentration of the UV-absorbing vinylic monomer is 1.50% by weight, the resultant lenses have a % T-UVA~8.80% and a % T-UVB~0.13%.

FIGS. 2 and 3 show the % T of the lenses having 0.7 wt % and 1.5 wt % of the UV-absorbing vinylic monomer after autoclave along with control lenses (0 wt % of the UV-absorbing vinylic monomer) after autoclave.

Example 4

This example illustrates how to prepare a preferred UV-absorbing vinylic monomer of the invention according to the following scheme.

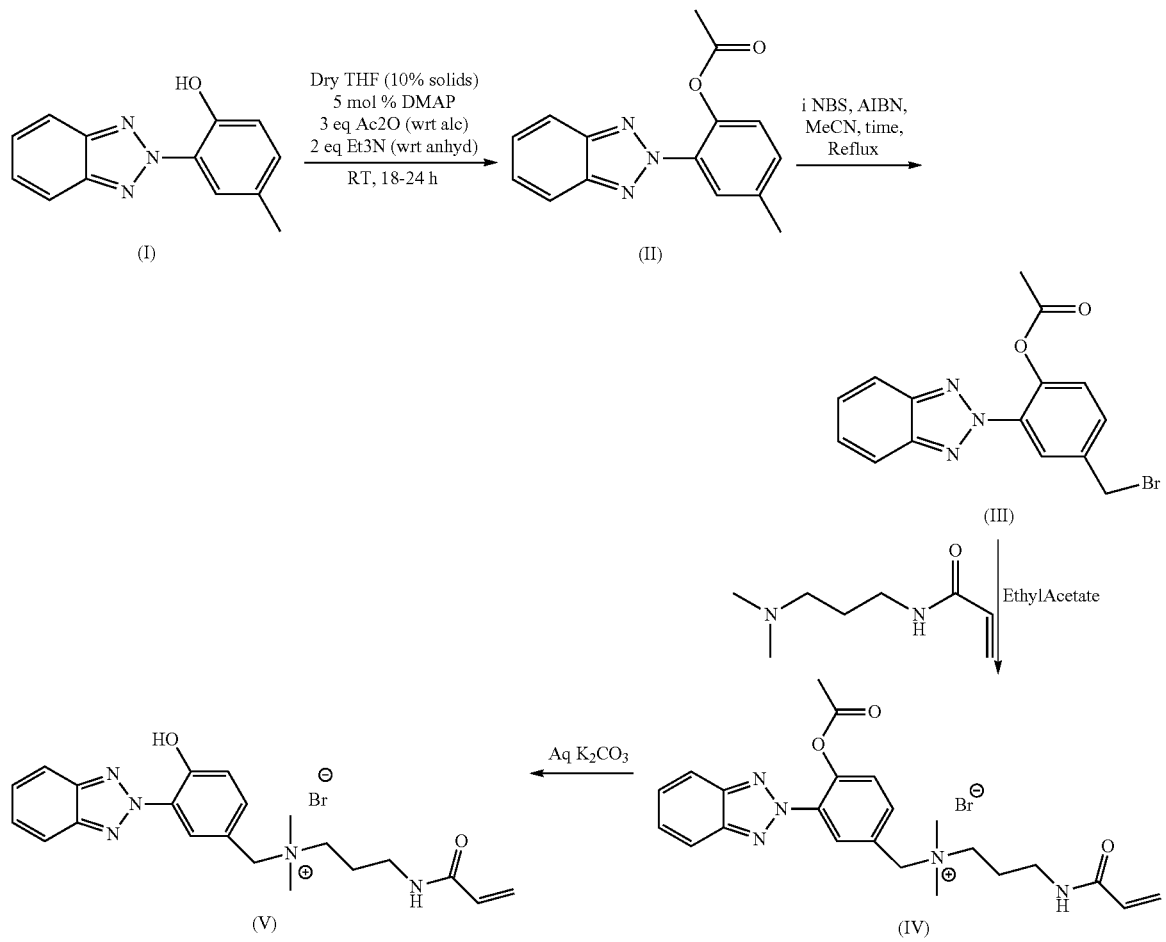

Step 1—Synthesis of 2-(2-acetyloxy-5-methylphenyl)benzotriazole (AcO-Me-Bzt)

In a weighed 2 L rb flask fitted with a magnetic stir bar and purged with $N_2$ is added 340 g anhydrous THF. The flask is purged with $N_2$ for a minute while stirring and then capped. 40 g (177.4 mmol, 1.0 eq) of 2-(2-Hydroxy-5-methylphenyl) benzotriazole (Me-Bzt-OH, from TCI-America) is weighed and added to the flask. The reaction flask is quickly purged with $N_2$ and then capped and stirred to allow the solid to dissolve. To this solution is added 1.09 g (8.87 mmol) of 4-dimethylaminopyridine (4-DMAP) (5 mol % wrt benotriazole). The flask is quickly purged with $N_2$, capped and the reaction mixture is allowed to stir to allow the solid to dissolve. 108.96 g (6 eq) of Triethyl amine ($Et_3N$) is weighed out and slowly added to the reaction flask with stirring. 54.58 g (3 eq) of $Ac_2O$ is weighed out and then slowly added to the reaction solution. 20 g of THF is added to the reaction. The flask is purged with $N_2$, capped tightly and the reaction solution is allowed stir under $N_2$ overnight.

The reaction solution is concentrated under reduced pressure, to remove ~65-70% of the volatiles or until precipitation is observed, whichever is earlier. If precipitation is seen, just enough THF is added to just dissolve the precipitate. The solution is stirred at RT for 30 mins. The product is precipitated by addition of a mixture of 250 g ice and 250 g DI Water with stirring. The obtained mixture had a pH of 4.75. The flask is place in an ice bath and stirred for 3 hours. The mixture is filtered through a Whatman #4 (25 um) filter paper under vacuum of 950 mbar. The precipitate is washed five times with 1 Kg of ice-water until the washings are clear colorless and the conductivity of the filtrate is <10 uS/cm. The precipitate is collected and mixed with 500 mL cold DI water. The mixture is frozen and then lyophilized to give a white powder (47.22 g) whose structure is confirmed by NMR to be AcO-Me-Bzt. Net: 47.22 g; Th Yield: 47.29 g; Yield: 99.85%; Purity: >90%.

Step 2—Synthesis of 2-(2-acetyloxy-5-bromomethylphenyl)benzotriazole (AcO—$BrCH_2$-Bzt)

In a 1 L 3-neck flask fitted with condenser, a $N_2$ purge set up, a thermocouple and an oil-bubbler air trap was added 20 g (0.074 mmol/1.0 eq) of AcO-Me-Bzt (II) from Step 2. This solid was stirred under $N_2$ for at least 45 mins. To this was added 480 mL of anhydrous acetonitrile and the mixture was stirred at RT under $N_2$ to effect a solution. The condenser was set to 9° C. and the reaction solution was gently bubbled with dry $N_2$ for 30 mins. After condenser had reached 4° C.

or 30 mins of $N_2$ purge (whichever is later), the reaction mixture was quickly raised to reflux, stirred at 400 rpm with a slightly positive $N_2$ flow. The reaction solution came to reflux at ~81-82° C. 14.71 g (1.1 eq) of NBS and 1.25 g (0.1 eq) of AIBN were added to the reaction flask under positive $N_2$ flow and the reaction were allowed to continue at reflux under a slightly positive $N_2$ flow. After 2 h 15 m the reaction was stopped by being allowed to cool to RT under $N_2$. The reaction solution was filtered through a cotton plug into a 1 L rb flask. The solution was then concentrated under reduced pressure to yield a solid material. To the sample was added 75 mL of 6.67% ACN in THF to dissolve the solid. About 250 g of 1:1 ice-water by weight was prepared (~2.5× the total solution volume). The product was precipitated by slow addition of the ice-water mixture with stirring. The flask was then placed in an ice bath and stirred for 3 hours. The precipitate was filtered through a Whatman #4 (25 um) filter paper under mild vacuum. The precipitate was washed 5× with 500 mL cold DI Water. (~10× volume of ice-water used for precipitation) until the conductivity of the filtrate was <10 uS/cm and neutral pH. The solid sample obtained was transferred to a 1 L rb flask and mixed 100 mL cold DI Water. The mixture was then frozen and then lyophilized to give a solid product (Net: 26.08 g; Th. yield: 25.83 g; % Yield: >100%; purity: 75% with 10% likely to be unreacted starting material and 15% unidentified material).

Step 3—Synthesis of Compound IV

In weighed amber 1 L flask with stir bar was taken 22 g (0.058 mol/1 eq) of product (III) (AcO—$BrCH_2$-Bzt), assuming 92% purity based on NMR. To this was added 350 mL ethyl acetate (EtAc) to dissolve. The solution was stirred at RT for an hour. During this time 27.592 g/0.176 mol/3 eq of NN-DMAPrAAm was measured out in a 50 mL dropping funnel. The NN-DMAPrAAm was slowly added to the reaction solution dropwise over 15 minutes at RT with stirring. A precipitate slowly began to form and the reaction was stirred at RT overnight, covered in foil. The stirring was stopped and the precipitate was allowed to settle. The supernatant was decanted from the reaction solution to give 70.4 g of a solid. To this was added 70 mL acetonitrile and the mixture swirled for an hour in a foil covered flask at RT, to dissolve. The resulting solution was concentrated under reduced pressure to remove 80% of the volatiles. To the solution was slowly added 120 mL of 16.7% hexane in EtAc with stirring, to give a 2-phase mixture. The clear supernatant was decanted to give about 30 g of a viscous semi-solid. To the viscous residue was added 60 mL of acetonitrile and swirled for 15 mins to dissolve the residue and then concentrated under reduced pressure to remove 90-95% of the volatiles. A clear viscous liquid was obtained. To this was added 120 mL of 16.67% hexane in Ethyl acetate solution using a dropping funnel with stirring. Two phases were observed a lower viscous paste-like solid and upper hazy supernatant phase. The mixture was stirred gently at RT for 15 mins and then allowed to stand for 45 mins. The clear colorless supernatant was decanted to yield about 32 g of a viscous semi-solid. This process was repeated twice more to yield a viscous semi-solid reside. The volatiles from the crude residue were removed under reduced pressure to give about 25 g of solid material. MEHQ, 3.7 mg, was dissolved in Acetonitrile and added to the residue (~150 mg/Kg (ppm) MEHQ based on estimated product weight). About 50 mL of acetonitrile was added to the residue and the mixture swirled to dissolve over 15 minutes. The solution was concentrated in an amber flask under reduced pressure to remove as much of the volatiles as possible to give 21.21 g of a solid mass. To the residue was added 200 g DI Water and the mixture were stirred for 10 minutes. The sample was gravity filtered, in the dark, through a Whatman#5 (2.5 um) filter paper, to give a clear solution having neutral pH. This clear solution was frozen and lyophilized to give an off-white solid. Total Yield 18 g % Yield: 77%.

Step 4—Synthesis of Compound V (UV-Absorbing Vinylic Monomer Having a Benzotriazole Moiety)

A 5.0 mL solution of product IV in DI Water at a concentration of 1000 mg/L was prepared. This aqueous solution was diluted to 20 mg/L with pH7 buffer (12.5 mM phosphate in DI Water:n-propanol). The UV-Vis spectrum of this solution was collected (FIG. 4, Curve 1).

Solid potassium carbonate ($K_2CO_3$) was added to the 1000 mg/L solution to have a $K_2CO_3$ concentration of 1 w/v %. The solution was mixed to dissolve the $K_2CO_3$ and the solution was allowed to stand overnight at RT to obtain the desired product—UV-absorbing vinylic monomer (i.e., compound V in the scheme). The resultant solution was diluted to 20 mg/L of the UV-absorbing vinylic monomer with pH7 buffer (12.5 mM phosphate in DI Water:n-propanol). The UV-Vis spectrum of this solution of the UV-absorbing vinylic monomer was collected and is shown in FIG. 4 (Curve 2).

Example 5

The UV-absorbing vinylic monomer prepared in Example 4 was directly added to an aqueous lens formulation, which is described in Example 8-8d of WO2002071106 (herein incorporated by reference in its entirety), at a concentration of 0, 0.91 wt % and 1.4 wt % and each having 1.0 wt % Li-TPO as the photoinitiator. Those three formulations are determined by photo rheology studies (405 nm LED source at 30 mW/$cm^2$) to have a curing time of about 25 seconds, about 60 seconds, or about 82 seconds respectively.

Lenses were fabricated from those aqueous formulations according to an automated lens manufacturing process described in Example 8 of WO2002071106 except that a lens formulation in a mold is irradiated with 405 nm LED at an intensity of 30 mW/$cm^2$ for about 25 seconds. The resultant lenses were packaged in blister packages containing Saline 61, sealed and autoclaved at 121° C. for 45 mins. The % T of the autoclaved lenses was determined. Where the concentration of the UV-absorbing vinylic monomer is 0 (i.e., control lenses), the control lenses have a % T-UVA~95.57% and a % T-UVB~81.64%. Where the concentration of the UV-absorbing vinylic monomer is 0.91% by weight, the resultant lenses have a % T-UVA~7.39% and a % T-UVB~2.74%. Where the concentration of the UV-absorbing vinylic monomer is 1.40% by weight, the resultant lenses have a % T-UVA~3.45% and a % T-UVB~0.59%.

FIGS. 5 and 6 show the % T of the lenses having 0.91 wt % and 1.4 wt % of the UV-absorbing vinylic monomer after autoclave along with control lenses (free of the UV-absorbing vinylic monomer) after autoclave.

What is claimed is:

1. A UV-absorbing vinylic monomer of any one of formula (I) to (VII)

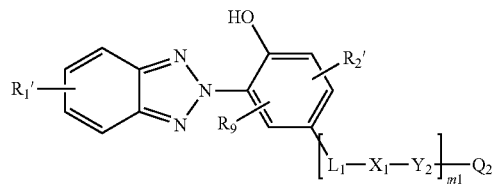
(IV)

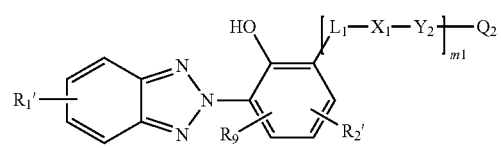
(V)

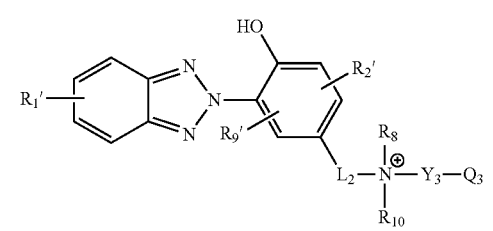
(VI)

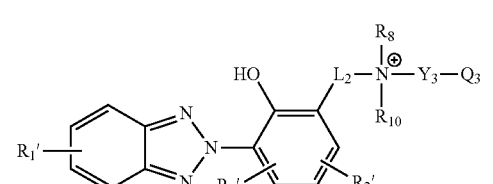
(VII)

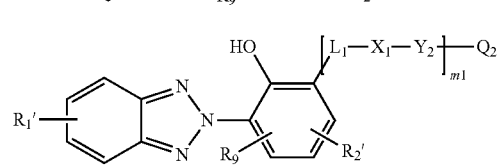
(V)

in which:

R$_2$ and R$_2$' independent of one other are H, CH$_3$, CCl$_3$, CF$_3$, Cl, Br, OH, OCH$_3$, or NR'R" in which R' and R" independent of each other are H or C$_1$-C$_4$ alkyl;

R$_1$' independent of each other are H, CH$_3$, CCl$_3$, CF$_3$, Cl, Br, OH, OCH$_3$, SO$_3$H, SO$_3$Na, or NR'R" in which R' and R" independent of each other are H or C$_1$-C$_4$ alkyl;

R$_9$ is SO$_3$Na,

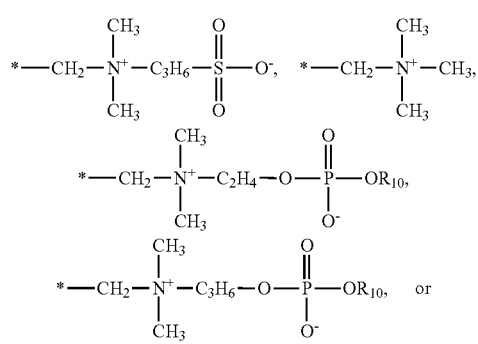

-continued

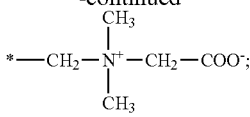

R$_9$' is H, SO$_3$Na,

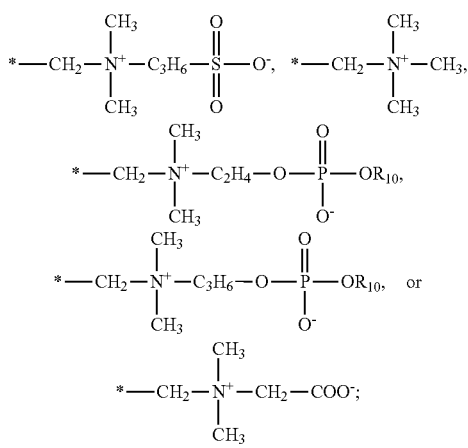

R$_{10}$ is methyl or ethyl;

L1 is a direct bond or a linkage of

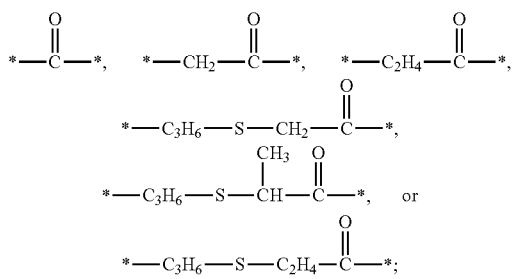

L2 is a linkage of

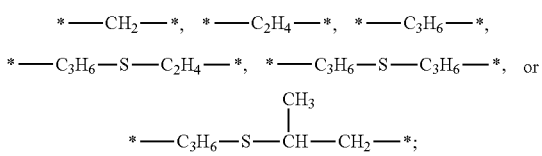

X1 is O or NR°; and

Y$_2$, and Y$_3$ independent of one another are a C$_2$-C$_4$ alkylene divalent radical;

Q2, and Q3 independent of one another are a (meth)acryloylamido or (meth)acryloyloxy group;

m1 is zero or 1, provided that if m1 is zero, then Q$_2$ is a (meth)acryloylamido group.

2. The UV-absorbing vinylic monomer of claim 1, being a vinylic monomer of formula (IV) or (V).

3. The UV-absorbing vinylic monomer of claim 2, being selected from a vinylic monomer of any one of the following formula:

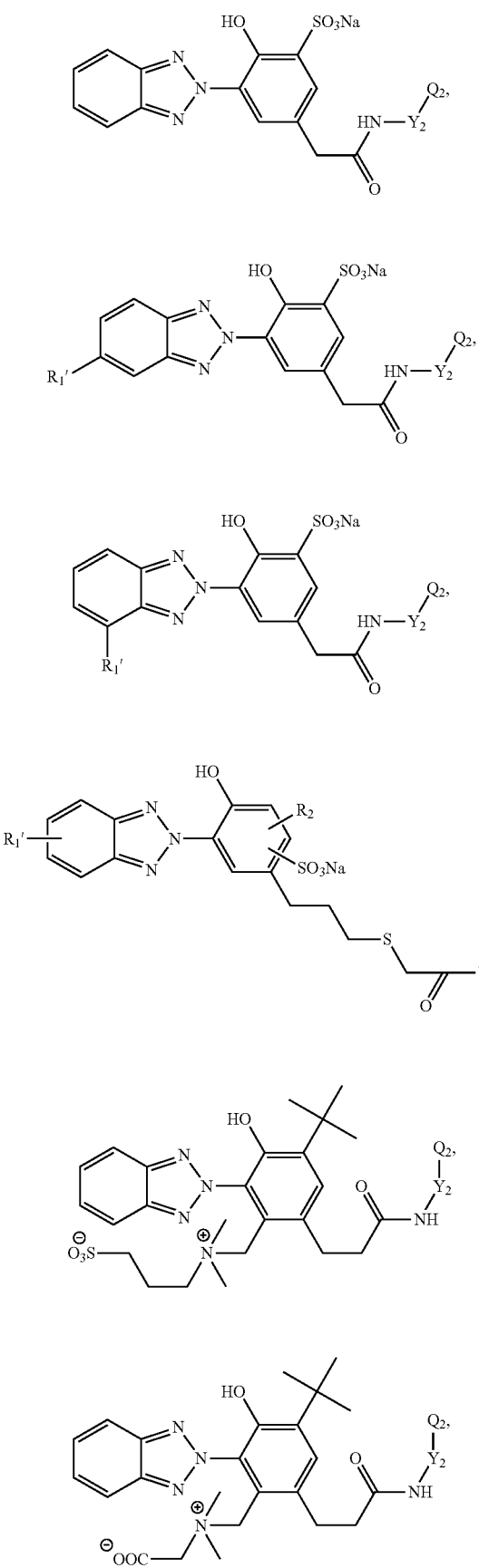

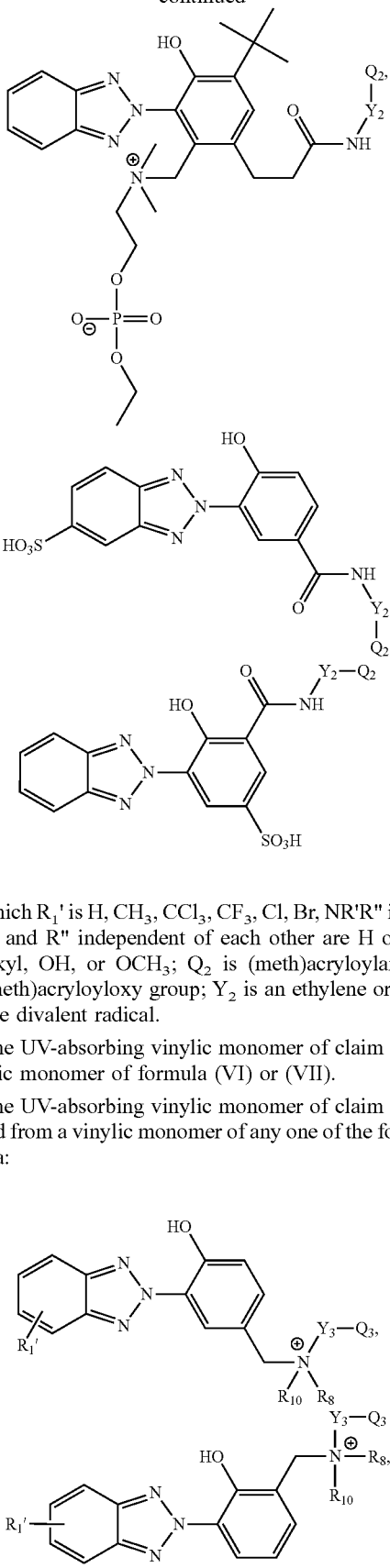

in which $R_1'$ is H, $CH_3$, $CCl_3$, $CF_3$, Cl, Br, NR'R" in which R' and R" independent of each other are H or $C_1$-$C_4$ alkyl, OH, or $OCH_3$; $Q_2$ is (meth)acryloylamido or (meth)acryloyloxy group; $Y_2$ is an ethylene or propylene divalent radical.

4. The UV-absorbing vinylic monomer of claim 1, being a vinylic monomer of formula (VI) or (VII).

5. The UV-absorbing vinylic monomer of claim 4, being selected from a vinylic monomer of any one of the following formula:

in which $R_1'$ is H, $CH_3$, $CCl_3$, $CF_3$, Cl, Br, OH, or $OCH_3$, NR'R" in which R' and R" independent of each other are H or $C_1$-$C_4$ alkyl, $R_8$ is $CH_3$, $C_2H_5$,
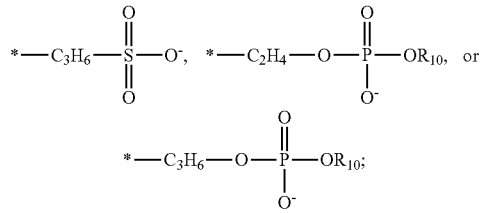
$R_{10}$ is methyl or ethyl; $Q_3$ is (meth)acryloylamido or (meth)acryloyloxy group; $Y_3$ is an ethylene or propylene divalent radical.
* * * * *